(12) United States Patent
Dormitzer

(10) Patent No.: US 10,342,862 B2
(45) Date of Patent: Jul. 9, 2019

(54) RSV IMMUNIZATION REGIMEN

(75) Inventor: Phillip Dormitzer, Weston, MA (US)

(73) Assignee: GlaxoSmithKline Biologicals, SA, Rixensart (BE)

(*) Notice: Subject to any disclaimer, the term of this patent is extended or adjusted under 35 U.S.C. 154(b) by 0 days.

(21) Appl. No.: 13/982,206

(22) PCT Filed: Jan. 26, 2012

(86) PCT No.: PCT/US2012/022762
§ 371 (c)(1),
(2), (4) Date: Oct. 22, 2013

(87) PCT Pub. No.: WO2012/103361
PCT Pub. Date: Aug. 2, 2012

(65) Prior Publication Data
US 2014/0044751 A1 Feb. 13, 2014

Related U.S. Application Data

(60) Provisional application No. 61/436,355, filed on Jan. 26, 2011.

(51) Int. Cl.
| | | |
|---|---|---|
| *A61K 39/155* | (2006.01) | |
| *C12N 15/86* | (2006.01) | |
| *A61K 39/12* | (2006.01) | |
| *A61K 39/00* | (2006.01) | |

(52) U.S. Cl.
CPC .......... *A61K 39/155* (2013.01); *A61K 39/12* (2013.01); *A61K 2039/545* (2013.01); *A61K 2039/55* (2013.01); *C12N 2760/18634* (2013.01)

(58) Field of Classification Search
None
See application file for complete search history.

(56) References Cited

U.S. PATENT DOCUMENTS

| | | | |
|---|---|---|---|
| 5,149,650 A * | 9/1992 | Wertz | A61K 39/155 435/243 |
| 8,563,002 B2 | 10/2013 | Baudoux et al. | |
| 8,715,692 B2 | 5/2014 | Pushko et al. | |
| 8,772,256 B2 | 7/2014 | Graham et al. | |
| 8,846,051 B2 | 9/2014 | Kew et al. | |
| 8,889,146 B2 | 11/2014 | Vassilev et al. | |
| 2011/0305727 A1 | 12/2011 | Swanson et al. | |

FOREIGN PATENT DOCUMENTS

| | | | |
|---|---|---|---|
| AU | 2012211278 | 5/2013 | |
| WO | WO 2008/133663 A2 * | 11/2008 | ............. A61K 39/00 |
| WO | WO 2009/042794 | 4/2009 | |
| WO | 2011/008974 | 1/2011 | |

OTHER PUBLICATIONS

Munoz et al. (Vaccine, 2003, p. 3465-3467).*
Fleeton et al. (Journal of Infectious Diseases, 2001, vol. 183, p. 1395-1398).*
Karron et al. (Journal of Infectious Diseases, 2005, vol. 191, p. 1093-1104).*
Storey (Nature Reviews, 2010, vol. 9, p. 15-16).*
Crowe, J. E., et al., Cold-passaged, temperature-sensitive mutants of human respiratory syncytial virus (RSV) are highly attenuated, immunogenic, and protective in seronegative chimpanzees, even when RSV antibodies are infused dhortly before immunization, Vaccine, vol. 13, No. 9, Jun. 1, 1995, pp. 847-855.
Englund, J., et al., Maternal immunization against viral disease, Vaccine, vol. 16, No. 14-15, Aug. 9, 1998, pp. 1456-1463.
Sales, V., et al., Respiratory syncytial virus vaccine: Is it coming?, Paediatrics & Child Heatlh : The Journal of the Canadian Paediatric Society, vol. 8, No. 20, Dec. 1, 2003, pp. 605-608.
Glezen, et al., "Risk of Respiratory syncytial virus infection for infants from low-income families in relationship to age, sex, ethnic group and maternal antibody level." J Pediatr., 1981 May;98(5):708-15.
Marchant, "T Cell-Mediated Immune Responses in Human Newborns: Ready to Learn?" 2005 Clinical and Exp. Immunol. 141:10-18.
Brandenberg, et al., "Respiratory Syncytial Virus Specific Serum Antibodies in Infants Under Six Months of Age: Limited Serological Response Upon Infection." (1997) J Medical Virology 52:97-104.
Calder et al., "Electron Microscopy of the Human Respiratory Syncytial Virus Fusion Protein and Complexes That if Forms with Monoclonal Antibodies" (2000) Virol 271 :122-131.
Crowe, et al., "Passively Acquired Antibodies Suppress Humoral But Not Cell-Mediated Immunity in Mice Immunized with Live Attenuated Respiratory Syncytial Virus Vaccines" (2001) J Immunol 167:3910-3918.
Crowe, "Influence of Maternal Antibodies on Neonatal Immunization against Respiratory Viruses." (2001) Vaccines; 33: 1720-1727.
Demirjian, et al., "Safety and Efficacy of Neonatal Vaccination." (2009) Eur J Immunol 39(1):36-46.
Gonzalez-Reyes, et al., "Cleavage of the Human Respiratory Syncytial Virus Fusion Protein at Two Distinct Sites is Required for Activation of Membrane Fusion." (2001) PNAS 98:9859-9864.
Halsey et al., "The efficacy of DPT and oral poliomyelitis immunization schedules initiated from birth to 12 weeks of age." Bulletin of the World Health Organisation (1985) 63(6):1151-1169.
Higgins, et al., "Advances in RSV Vaccine Research and Development—A Global Agenda." (2016) Vaccine 34:2870-2875.
Kim et al., " Respiratory Syncytial Virus Disease in Infants Despite Prior Administration of Antigenic Inactivated Vaccine." Am J Epidemiol (1969) 89:422-434.
Martin et al., "Sequence Elements of the Fusion Peptide of Human Respiratory Syncytial Virus Fusion Protein Required for Activity." (2006) J Gen Virol 87:1649-1658.

(Continued)

*Primary Examiner* — Agnieszka Boesen
(74) *Attorney, Agent, or Firm* — Eric J. Kron

(57) ABSTRACT

The invention relates to an immunization regimen whereby an infant is protected against respiratory syncytial virus (RSV) through administration of a first anti-RSV immune response inducing composition to his or her mother during pregnancy, followed by administration of a second anti-RSV immune response inducing composition to the infant after birth.

20 Claims, 1 Drawing Sheet

Figure 1A:
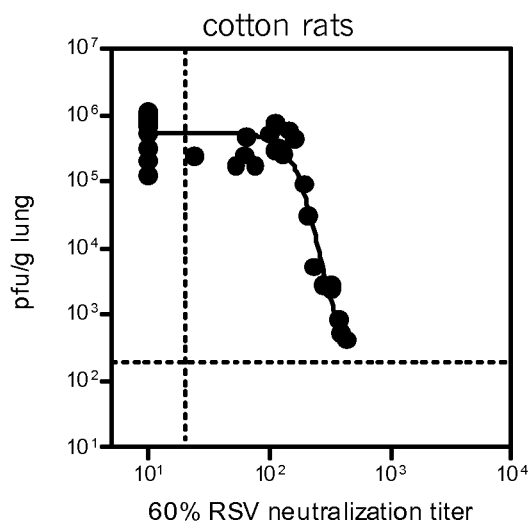

Specification includes a Sequence Listing.

(56) References Cited

OTHER PUBLICATIONS

Martinez et al., "Combining DNA and Protein Vaccines for Early Life Immunization Against Respiratory Syncytial Virus in Mice." (1999) Eur J Immunol 29:3390-3400.
Munoz et al., "Safety and Immunogenicity of Respiratory Syncytial Virus Purified Fusion Protein-2 Vaccine in Pregnant Women." (2003) Vaccine 21:3465-3467.
Murphy et al., "Effect of Age and Preexisting Antibody on Serum Antibody Response of Infants and Children to the F and G Glycoproteins during Respiratory Syncytial Virus Infection." (1986) J Clin Microbiol 24:894-898.
Murphy et al., "Passive Transfer of Respiratory Syncytial Virus (RSV) Antiserum Suppresses the Immune Response to the RSV Fusion (F) and Large (G) Glycoproteins Expressed by Recombinant Vaccinia Viruses" (1988) J Virol 62:3907-3910.
Murphy et al., "Effect of Passive Antibody on the Immune Response of Cotton Rats to Purified F and G Glycoproteins of Respiratory Syncytial Virus (RSV)." (1991) Vaccine 9:185-189.
Ruiz-Arguello et al., "Effect of Proteolytic Processing at Two Distinct Sites on Shape and Aggregation of an Anchorless Fusion Protein of Human Respiratory Syncytial Virus and Fate of the Intervening Segment." (2002) Virol; 298:317-326.
Siegrist et al., "Protective Efficacy against Respiratory Syncytial Virus following Murine Neonatal Immunization with BBG2Na Vaccine: Influence of Adjuvants and Maternal Antibodies." (1999) J Infect Dis 179:1326-1333.
Siegrist et al., "Mechanisms by which Maternal Antibodies Influence Infant Vaccine Responses: Review of Hypotheses and Definition of Main Determinants."(2003) Vaccine 21:3406-3412.
The Australian Immunisation Handbook (2008) 9th edition Australian Government Health and Ageing; NHMRC).
National Immunisation Program Schedule (2007) Australian Government (Dep Health and Ageing).
Opposition Statement of Grounds and Particulars in relation to Australian application No. 2012211278, May 10, 2017.
Opposition Statement of Grounds and Particulars in relation to Australian application No. 2012211278, Aug. 11, 2017.

* cited by examiner

RSV IMMUNIZATION REGIMEN

RELATED APPLICATIONS

This application is a U.S. National Phase patent application of PCT/US2012/022762, filed Jan. 26, 2012, which claims the benefit of U.S. patent application No. 61/436,355, which was filed on Jan. 26, 2011. The entire contents of both foregoing applications are incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 25, 2012, is named 85448116.txt and is 15,682 bytes in size.

BACKGROUND

Respiratory syncytial virus (RSV) is an enveloped non-segmented negative-strand RNA virus in the family Paramyxoviridae, genus *Pneumovirus*. It is the most common cause of bronchiolitis and pneumonia among children in their first year of life. RSV also causes repeated infections including severe lower respiratory tract disease, which may occur at any age, especially among those with compromised cardiac, pulmonary, or immune systems.

To infect a host cell, paramyxoviruses such as RSV, like other enveloped viruses such as influenza virus and HIV, require fusion of the viral membrane with a host cell's membrane. For RSV the conserved fusion protein (RSV F) fuses the viral and cellular membranes by coupling irreversible protein refolding with juxtaposition of the membranes. In current models based on paramyxovirus studies, the RSV F protein initially folds into a metastable "pre-fusion" conformation. During cell entry, the pre-fusion conformation undergoes refolding and conformational changes to its stable "post-fusion" conformation.

The RSV F protein is translated from mRNA into an approximately 574 amino acid protein designated $F_0$. Post-translational processing of $F_0$ includes removal of an N-terminal signal peptide by a signal peptidase in the endoplasmic reticulum. $F_0$ is also cleaved at two sites (approximately 109/110 and approximately 136/137) by cellular proteases (in particular furin) in the trans-Golgi. This cleavage results in the removal of a short intervening sequence and generates two subunits designated $F_1$ (~50 kDa; C-terminal; approximately residues 137-574) and $F_2$ (~20 kDa; N-terminal; approximately residues 1-109) that remain associated with each other. $F_1$ contains a hydrophobic fusion peptide at its N-terminus and also two amphipathic heptad-repeat regions (HRA and HRB). HRA is near the fusion peptide and HRB is near the transmembrane domain. Three $F_1$-$F_2$ heterodimers are assembled as homotrimers of $F_1$-$F_2$ in the virion. A suitable vaccine for infants against RSV infection is not currently available, but is desired.

Previous attempts at RSV vaccines have led to failed clinical trials wherein the vaccine did not protect against infection and in fact was associated with increased risk of severe RSV disease when the vaccinated children became infected. Kim, H. W., et al., Am. J. Epidemiol., 89:422-434 (1969). Traditional immunization methods for vaccinating infants from RSV are not available.

Thus, there is a need for improved RSV immunization regimens.

SUMMARY

The invention relates to methods for providing protective immunity against RSV in an infant, comprising (a) administering a first anti-RSV immune response inducing composition to a female during pregnancy; and (b) administering a second anti-RSV immune response inducing composition to the infant that is born from the pregnancy.

The invention also relates to methods for protecting an infant from disease caused by RSV, comprising administering to an infant an anti-RSV immune response inducing composition, wherein the infant was born to a female to whom an anti-RSV immune response inducing composition was administered during the time when the female was pregnant with the infant.

In some aspects the anti-RSV immune response inducing composition administered to a female during pregnancy boosts a neutralizing antibody response in the female. The neutralizing antibody response may be characterized by a 2-fold or greater increase in neutralizing titer. The neutralizing antibody response can be characterized by neutralizing antibodies. In some embodiments the neutralizing antibodies are complement independent. In some embodiments, the administering to a female during pregnancy is done during the second or third trimester of pregnancy. In some embodiments, the administering to the infant born from the pregnancy occurs immediately after birth, about 2 weeks after birth, about 4 weeks after birth, about 6 weeks after birth, about 2 months after birth, about 3 months after birth, about 4 months after birth, about 6 months after birth, about 9 months after birth, or about 12 months after birth.

In some embodiments, the first anti-RSV immune response inducing composition and the second anti-RSV immune response inducing composition are the same. The anti-RSV immune response inducing compositions can each comprise an RSV subunit composition, a nucleic acid, a viral replicon particle, a live attenuated virus, an inactivated virus particle, a recombinant viral vector, or a virus-like particle. The anti-RSV immune response inducing compositions can each comprise one or more peptides or a virosomal composition.

In some embodiments, the first anti-RSV immune response inducing composition is not the same as the second anti-RSV immune response inducing composition. The first anti-RSV immune response inducing composition can comprise an RSV subunit composition, a nucleic acid or a viral replicon particle; and the second anti-RSV immune response inducing composition can comprise an RSV subunit composition, a nucleic acid or a viral replicon particle; with the proviso that the first and second anti-RSV immune response inducing compositions are not both an RSV subunit composition, a nucleic acid or a viral replicon particle. The first anti-RSV immune response inducing composition can comprise an RSV subunit composition, a nucleic acid, a recombinant viral vector, or a viral replicon particle; and the second anti-RSV immune response inducing composition can comprise an RSV subunit composition, a nucleic acid, a recombinant viral vector, or a viral replicon particle; with the proviso that the first and second anti-RSV immune response inducing compositions are not both an RSV subunit composition, a nucleic acid or a viral replicon particle. In some embodiments the first anti-RSV immune response inducing composition comprises an RSV subunit composition. In some embodiments, the second anti-RSV immune response inducing composition comprises a nucleic acid or viral replicon particle. In some embodiments, the second anti- RSV immune response inducing composition comprises a nucleic acid, a recombinant viral vector, or viral replicon particle.

In a preferred aspect, the first anti-RSV immune response inducing composition that is administered to a female during pregnancy does not replicate in the female after administration, and the second anti-RSV immune response inducing composition that is administered to the infant that is born from the pregnancy does replicate itself or its genome in the infant. For example, the first anti-RSV immune response inducing composition can be, for example, an RSV subunit composition, an RSV virus-like particle (VLP), one or more RSV peptides, an epitope mimitec composition, a virosomal composition, or a killed RSV virion composition, and the second anti-RSV immune response inducing composition can be, for example, a self-replicating nucleic acid (e.g., a self replicating (self-amplifying) RNA), a live attenuated virus, a heterologous live virus (e.g. an RSV-related virus with a non-human primary host), a live viral vector, a chimeric live virus, or a viral replicon particle.

BRIEF DESCRIPTION OF THE DRAWING

FIGS. 1A and 1B are graphs showing the correlation between serum neutralization titers and protection for RSV challenge in cotton rat (FIG. 1A) or BALB/c mice (FIG. 1B). Cotton rats and mice were injected i.p. with donor serum containing different levels of RSV-specific antibody (see Example 3 methods and Tables 3 and 4 for more details) and challenged i.n. with RSV 2 days later. Each circle represents the serum neutralization titer one day after transfer and the lung viral load after challenge (5 days post challenge for cotton rats, 4 days post challenge for mice) for an individual animal. Dotted lines indicate assay limits of detection, and solid line the 4-parameter best fit curve for the data used to calculate the neutralization titer correlated with no detectable virus after challenge.

DETAILED DESCRIPTION

As described herein, the inventors have discovered an immunization regimen whereby an infant is protected against respiratory syncytial virus (RSV) through administration of a first anti-RSV immune response inducing composition to his or her mother (i.e., a pregnant female) during pregnancy, followed by administration of a second anti-RSV immune response inducing composition to the infant after birth. The immunization of the pregnant female provides antibody-mediated immunity to the infant through passive maternal immunity. The passive immunity occurs naturally when maternal antibodies are transferred to the fetus through the placenta.

Passive immunity is especially important to infants because they are born without any actively acquired immunity. Administration of an anti-RSV immune response inducing composition to a pregnant female enhances immunity to RSV in the female, and anti-RSV antibodies are passed to the newborn through the placenta, conferring passive maternal immunity on the infant. However, passive immunity in infants is only temporary and starts to decrease after the first few weeks, or months of life. As passive immunity is only temporary, it is important for the infant to receive administration of an anti-RSV immune response inducing composition, to induce active immunity in the infant, before the passive immunity diminishes. Administration of a second immunogenic composition to the infant after birth induces active immunity against RSV in the infant, and extends the immunity passed on from the mother during pregnancy.

The immunization regimen described herein provides several advantages. For example, this approach provides protection from RSV infection to the infant from birth. An additional advantage is that administering an anti-RSV immune response inducing composition to the infant according to the regimen described herein can result in greater induction of neutralizing RSV immunity than prior approaches to infant immunization. The peak of severe illness due to RSV occurs at approximately two to three months of age. Immunization of pregnant women, increasing their antibody titers and the passive antibody titers in their infants, could delay the onset of RSV-caused disease in infants until a time when their respiratory systems are more mature and they are less likely to become severely ill. The newborn immune system is immature, making active immunization of newborns less effective than immunization of older infants. The delay in RSV illness in infants due to enhanced passive immunity from immunization of pregnant women will allow more time for active infant immunization before the age of highest risk for severe disease. This added time for effective immunization could allow multiple doses of vaccine to be given to an infant and/or doses to be given later in infancy, when the immune system is more mature but still before the infant's first RSV infection or RSV-caused illness.

As used herein, an infant is an individual under one year of age (e.g., less than one day old, 1 week old, 2 weeks old, 3 weeks old, 4 weeks old, 2 months old, 3 months, 4 months, 5 months, 6 months, 7 months, 8 months old, 9 months old, 10 months old, 11 months old, less than 12 months old).

As used herein, an anti-RSV immune response inducing composition is any composition that is suitable for administration to a mammal and is effective to induce active immunity or boost an immune response, preferably a protective immune response, against RSV. The anti-RSV immune response inducing composition will provide one or more RSV antigens, and can be in the form of, for example, a subunit composition comprising an RSV protein antigen, a nucleic acid that encodes an RSV protein antigen, a viral replicon particle (VRP) that contains a nucleic acid that encodes an RSV protein antigen, live attenuated viruses, inactivated viruses, virus-like particles (VLP), or recombinant viral vectors. The RSV antigen can be any desired RSV antigen. For example, the anti-RSV immune response inducing composition may comprise an RSV glycoprotein or a portion thereof (e.g., the ectodomain), preferably an RSV F glycoprotein. The RSV glycoprotein may be in any conformation (e.g., pre-fusion conformation, post-fusion conformation) or a mixture of conformations. The RSV antigen administered to the pregnant female and the infant may be from different serogroups, different serotypes, different immunotypes, different serovars, different biovars, different strains, different clades, or different species and/or may contain mutations (e.g., deletions). The RSV antigen administered to the pregnant female and the infant may be from different subtypes.

The anti-RSV immune response inducing compositions used in the immunization regimen may be the same or different. For example, the female may be administered a RSV subunit composition, a nucleic acid, a viral replication particle (VRP) or an attenuated virus during pregnancy and the infant is administered the same or different RSV subunit composition, nucleic acid, viral replication particle (VRP) or attenuated virus after birth. In another example, the female may be administered an attenuated virus during pregnancy and the infant is administered a RSV subunit composition, a nucleic acid or a VRP after birth. In some instances, both the infant and the pregnant female are administered attenuated vaccines. In other instances, both the infant and the pregnant female are administered the same or different anti-RSV immune response inducing composition selected from the group consisting of RSV subunit compositions, nucleic acids, and VRPs. In still other instances, the infant is administered a prime with one anti-RSV immune response inducing composition and administered a boost with another anti-RSV immune response inducing composition. For example, the infant may be primed with a nucleic acid and boosted with a subunit composition. In some instances, either the infant or the pregnant female or both the infant and the pregnant female are each administered more than one anti-RSV immune response inducing compositions simultaneously. For example, the infant, the pregnant female, or the infant and the pregnant female may each be administered a nucleic acid and a subunit composition simultaneously.

In some embodiments, the anti-RSV immune response inducing composition administered to the female and the anti-RSV immune response inducing composition administered to the infant are not the same. For example, the anti-RSV immune response inducing composition administered to the female may comprise a RSV subunit composition, a nucleic acid or a VRP, and the anti-RSV immune response inducing composition administered to the infant may comprise a RSV subunit composition, a nucleic acid or a VRP, provided that the anti-RSV immune response inducing compositions administered to the female and to the infant are not both a RSV subunit composition, a nucleic acid or a viral replication particle.

The anti-RSV immune response inducing composition administered to the female will most likely be a boost. For example, the female will likely have experienced an RSV infection at some time in her life prior to the pregnancy, so that the anti-RSV immune response inducing composition administered to her during pregnancy will act as a boost. The boost will increase the anti-RSV antibody titer in the mother and enhance maternal immunity that is passed to the fetus and infant.

The pregnant female may be administered the anti-RSV immune response inducing composition at any time during her pregnancy. For example, the anti-RSV immune response inducing composition may be administered to the female during the first, second or third trimester of her pregnancy. In some embodiments, the anti-RSV immune response inducing composition is administered to the female during the last 6-12 weeks of the pregnancy (e.g., 28 weeks gestation, 29 weeks gestation, 30 weeks gestation, 31 weeks gestation, 32 weeks gestation, 33 weeks gestation, 34 weeks gestation, 35 weeks gestation, 36 weeks gestation, 37 weeks gestation, 38 weeks gestation, 39 weeks gestation). Preferably, the anti-RSV immune response inducing composition is administered to the pregnant female at least four weeks before delivery of the infant.

In some embodiments, a one-dose regimen is administered to the pregnant female between weeks 32 and 36 gestation.

In other embodiments, a two-dose regimen is administered to the pregnant female, with the first dose being administered at approximately 32 weeks gestation and the second dose being administered at approximately 36 weeks gestation.

The infant may be administered the anti-RSV immune response inducing composition at any time during the first year of life, and thereafter if desired. Generally the anti-RSV immune response inducing composition will be administered to the infant one, two, three, four or more times during the first year of life, and the compositions can be the same or different. For example, the anti-RSV immune response inducing composition may be administered to the infant one or more times selected from at birth, at 2 weeks old, 4 weeks old, 6 weeks old, 2 months old, 3 months old, 4 months old, 6 months old, 9 months old, and 12 months old. Preferably, the anti-RSV immune response inducing composition is administered to the infant at a time before maternal antibodies have decreased to non-protective titers, for example, the anti-RSV immune response inducing composition is initially administered to the infant at about 4 months old or younger. Subsequent administrations can occur on any desired schedule.

For example, an anti-RSV immune response inducing composition may be administered to the infant as a three-dose regimen. One possible dosing regimen includes administration at birth, 1 month old, and 2 months old. Another possible dosing regimen includes administration at 1 month old, 2 months old and 3 months old. Another exemplary dosing regimen includes administration at 1 month old, 2 months old and 4 months old.

Administration of the anti-RSV immune response inducing composition may be at substantially the same time as other vaccines (e.g., during the same medical consultation or visit to a healthcare professional or vaccination center) or at earlier times given the early onset of RSV disease.

In some embodiments, the anti-RSV immune response inducing composition comprise proteins, DNA molecules, self-replicating RNA molecules or VRPs. The anti-RSV immune response inducing composition may further comprise a pharmaceutically acceptable carrier and, optionally, an adjuvant. See, e.g., U.S. Pat. Nos. 6,299,884; 7,641,911; 7,306,805; and US 2007/0207090. Certain preferred anti-RSV immune response inducing compositions are described further herein.

The immune response can comprise a humoral immune response, a cell-mediated immune response, or both. In some embodiments an immune response is induced against each delivered RSV protein. A cell-mediated immune response can comprise a helper T-cell ($T_h$) response, a CD8+ cytotoxic T-cell (CTL) response, or both. In some embodiments the immune response comprises a humoral immune response, and the antibodies are neutralizing antibodies. Neutralizing antibodies block viral infection of cells. In some embodiments the immune response reduces or prevents infection of cells. Neutralizing antibody responses can be complement-dependent or complement-independent. In some embodiments the neutralizing antibody response is complement-independent. In some embodiments the neutralizing antibody response is cross-neutralizing; i.e., an antibody generated against an administered composition neutralizes a RSV virus of a strain other than the strain used in the composition. In some embodiments, the neutralizing antibody response is characterized by neutralizing IgG antibodies.

A useful measure of antibody potency in the art is "% neutralization titer" (e.g., 50% neutralization titer, 60% neutralization titer). To determine % neutralizing titer, serum from immunized individuals is diluted to assess how dilute serum can be yet retain the ability to block entry of 50% or 60%, respectively, of infectious viruses into cells. For example, a 50% neutralization titer of 20 means that serum retained the ability to neutralize 50% of virus after being diluted 20-fold. Thus, higher titers indicate more potent neutralizing antibody responses. In some embodiments, this titer is in a range having a lower limit of about 20, about 40, about 50, about 60, about 70, about 80, about 90, about 100, or about 200. The 50% neutralization titer range can have an upper limit of about 40, about 40, about 50, about 60, about 70, about 80, about 90 about 100, about 200, about 400, about 800, about 1600, about 3000, about 6000, about 8000, about 10000, or about 20000. For example, the 50% neutralization titer can be about 1:20, 1:40, 1:80, or about 1:100. "About" means within two-fold of the recited value. Neutralization titer can be measured as described herein.

Neutralization titer can be measured by mixing an RSV preparation with an antibody preparation, adding that mixture to cultured mammalian cells and then determining the proportion of the original RSV infectivity that remains in the antibody-virus mixture by assaying the consequences of adding the mixture to the cells. The antibody-containing preparation may include, for example, animal serum, human serum, antibodies purified from serum, or monoclonal antibodies from culture. In some instances complement, for example, guinea pig complement, may be mixed with the antibody and the RSV preparation. In some embodiments, serial dilutions of the antibody-containing preparation are added to virus samples. The mammalian cells used in the neutralization assay may be in a monolayer or in suspension, and may be infected. The inoculum, which may include both virus and antibody, may remain on the cells or may be removed after a brief time period (e.g., 30 minutes, 60 minutes, 90 minutes). The proportion of infected cells may be determined in a variety of means, including, for example, counting plaques that form under a semi-solid overlay, counting syncytia that form under a semi-solid overlay, immunostaining infectious foci after a brief incubation with virus, detection of a recombinant RSV-expressed fluorescent marker, identification of infected cells by observing cytopathic effect, identification of infected cells by immunostaining for an RSV marker, assessing the amount of RSV antigen in the supernatant of intact or lysed cells, detecting the amount of fluorescence from a recombinant RSV expressing a fluorescent antigen, detecting the amount of cell lysis by a biochemical assay (e.g., LDH), and observing the greatest dilution of virus at which any cytopathic effect is observed after a sufficient incubation time. Additional variations in the neutralization assay may include, for example, variations in the buffers, blocking agents, incubation times, controls, type of plate, incubation temperatures, cell culture medium, permeabilizing agent, fixation agent, cell substrate type, overlay composition, cell stain, volume of reagents, number of washes, use of secondary antibodies, counting method, calculation method, and percentage of neutralization used to calculate titer.

An immune response can be stimulated by administering an anti-RSV immune response inducing composition (a composition comprising proteins, DNA molecules, self-replicating RNA molecules or VRPs) to an individual. In some embodiments the immune response induced is a protective immune response, i.e., the response reduces the risk of RSV infection, delays the onset of RSV infection, reduces the risk of RSV-caused disease, reduced the severity of RSV-caused disease, delays the onset of RSV-caused disease, reduces the frequency of RSV-caused disease, reduces the sequelae of RSV infection or RSV-caused disease, or reduces the risk that an RSV-infected individual will spread RSV to another individual.

Any suitable route of administration can be used. For example, a composition can be administered intramuscularly, intraperitoneally, subcutaneously, transdermally, or intradermally. If desired, the composition can be administered through an intra-mucosal route such as intra-orally, intra-nasally, intra-vaginally, and intra-rectally. Administration to the pregnant female and the infant may be through the same route or different routes. Compositions can be administered according to any suitable schedule.

In one embodiment, protective immunity against RSV in an infant is provided comprising the steps of (a) administering a first anti-RSV immune response inducing composition to a female during pregnancy; and (b) administering a second anti-RSV immune response inducing composition to the infant that is born from the pregnancy. As described herein, the first anti-RSV immune response inducing composition and the second anti-RSV immune response inducing composition can be the same or different. This approach preferably induces or boosts neutralizing anti-RSV antibodies in the pregnant female which are passed to the infant through maternal immunity, and induces an active immune response in the infant. Thus, preferably, at the time the of the first administration of the anti-RSV immune response inducing composition to the infant, the infant contains maternal antibodies against RSV, and as a result of the administration will actively develop an immune response to RSV. Preferably, the anti-RSV immune response inducing composition is administered to the infant at a time when maternal antibodies are still at protective levels in the infant.

In a particular embodiment, protective immunity against RSV in an infant is provided by administering an anti-RSV subunit composition to a female during pregnancy; and administering an anti-RSV self replicating RNA composition to an infant that is born from the pregnancy. In a preferred embodiment, protective immunity against RSV in an infant is provided by administering an anti-RSV subunit composition to a female during pregnancy; and administering one or more anti-RSV self replicating RNA composition to an infant that is born from the pregnancy, followed by administering an anti-RSV subunit composition boost to the infant.

In another embodiment, an infant is protected from RSV infection by a method comprising administering to an infant an anti-RSV immune response inducing composition, wherein the infant was born to a female to whom an anti-RSV immune inducing or boosting composition was administered during the time when the female was pregnant with the infant. The anti-RSV immune response inducing composition that was administered to the female and the anti-RSV immune response inducing composition that is administered to the infant can be the same or different. Preferably, at the time of the first administration of the anti-RSV immune response inducing composition to the infant, the infant contains maternal antibodies against RSV, and as a result of the administration will actively develop an immune response to RSV. Preferably, the anti-RSV immune response inducing composition is administered to the infant at a time when maternal antibodies are still at protective titers in the infant.

In a preferred embodiment, an infant is protected from RSV infection by administering an anti-RSV self replicating RNA composition to an infant born to a female who was administered an anti-RSV subunit composition during the time that female was pregnant with the infant.

Anti-RSV Immune Response Inducing Composition

Any desired anti-RSV immune response inducing composition can be used in the invention. For example, RSV proteins or fragments can be delivered directly as components of anti-RSV immune response inducing composition, or nucleic acids that encode one or more RSV proteins or fragments can be administered to produce the RSV protein or fragment in vivo, or live attenuated viruses can be administered, or recombinant viral vectors expressing RSV proteins can be administered, or inactivated RSV viruses can be administered, or virus-like-particles containing RSV antigens can be administered. Certain preferred embodiments, such as protein formulations, recombinant nucleic acids (e.g., self replicating RNA) and alphavirus VRP that contain sequences encoding RSV proteins or fragments are further described herein.

Protein Formulations

Immunogenic proteins or fragments thereof used according to the invention will usually be isolated or purified. Thus, they will be separate and discrete from the whole organism or virion with which the molecule is found in nature or is present in the substantial absence of other biological macromolecules of the same type.

RSV exists as a single serotype but has two antigenic subgroups: A and B. The F glycoproteins of the two groups are about 90% identical. The A subgroup, the B subgroup, or a combination or hybrid of both can be used in the invention. An example sequence for the A subgroup is SEQ ID NO: 1 (A2 strain; GenBank GI: 138251; Swiss Prot P03420), and for the B subgroup is SEQ ID NO: 2 (18537 strain; GI: 138250; Swiss Prot P13843). SEQ ID NO:1 and SEQ ID NO:2 are both 574 amino acid sequences. The signal peptide in A2 strain is a.a. 1-21, but in 18537 strain it is 1-22. In both sequences the TM domain is from about a.a. 530-550, but has alternatively been reported as 525-548.

(i.e., amino acids 109 and 136 of SEQ ID NOS: 1 and 2). These mutations can prevent aggregation of the soluble polypeptides or proteins and thereby facilitate purifications, can prevent cell-cell fusion if the RSV F protein is expressed on the surface of a cell, such as by expression from a viral replicon (e.g., alphavirus replicon particles), or if the RSV F protein is a component of a virus-like particle. These mutations, alone or in combination with other mutations described herein, may also stabilize the protein in the pre-fusion conformation.

Examples of suitable furin cleavage mutations include replacement of amino acid residues 106-109 of SEQ ID NO: 1 or 2 with RARK (SEQ ID NO:3), RARQ (SEQ ID NO:4), QAQN (SEQ ID NO:5), or IEGR (SEQ ID NO:6). Alternatively, or in addition, amino acid residues 133-136 of SEQ ID NO: 1 or 2 can be replaced with RKKK (SEQ ID NO:7), ΔΔΔR, QNQN (SEQ ID NO:8), QQQR (SEQ ID NO:9) or IEGR (SEQ ID NO:10). (Δ indicates that the amino acid residue has been deleted.) These mutations can be combined, if desired, with other mutations described herein, such as mutations in the p27 region (amino acids 110-136 of SEQ ID NOS: 1 or 2), including deletion of the p27 region in whole or in part.

These furin cleavage mutations can be combined, if desired, with other mutations described herein, such as trypsin cleavage mutations and fusion peptide mutations. Examples of suitable trypsin cleavage mutations include deletion of any lysine or arginine residue between about position 101 and position 161 of SEQ ID NO:1 or 2, or

```
                                                            SEQ ID NO: 1
    1   MELLILKANAITTILTAVTFCFASGQNITEEFYQSTCSAVSKGYLSALRTGWYTSVITIE      60

61   LSNIKENKCNGTDAKVKLIKQELDKYKNAVTELQLLMQSTPPTNNRARRELPRFMNYTLN     120

121   NAKKTNVTLSKKRKRRFLGFLLGVGSAIASGVAVSKVLHLEGEVNKIKSALLSTNKAVVS     180

181   LSNGVSVLTSKVLDLKNYIDKQLLPIVNKQSCSISNIETVIEFQQKNNRLLEITREFSVN     240

241   AGVTTPVSTYMLTNSELLSLINDMPITNDQKKLMSNNVQIVRQQSYSIMSIIKEEVLAYV     300

301   VQLPLYGVIDTPCWKLHTSPLCTTNTKEGSNICLTRTDRGWYCDNAGSVSFFPQAETCKV     360

361   QSNRVFCDTMNSLTLPSEINLCNVDIFNPKYDCKIMTSKTDVSSSVITSLGAIVSCYGKT     420

421   KCTASNKNRGIIKTFSNGCDYVSNKGMDTVSVGNTLYYVNKQEGKSLYVKGEPIINFYDP     480

481   LVFPSDEFDASISQVNEKINQSLAFIRKSDELLHNVNAGKSTTNIMITTIIIVIIVILLS     540

541   LIAVGLLLYCKARSTPVTLSKDQLSGINNIAFSN                               574

SEQ ID NO: 2
    1   MELLIHRSSAIFLTLAVNALYLTSSQNITEEFYQSTCSAVSRGYFSALRTGWYTSVITIE      60

61   LSNIKETKCNGTDTKVKLIKQELDKYKNAVTELQLLMQNTPAANNRARREAPQYMNYTIN     120

121   TTKNLNVSISKKRKRRFLGFLLGVGSAIASGIAVSKVLHLEGEVNKIKNALLSTNKAVVS     180

181   LSNGVSVLTSKVLDLKNYINNRLLPIVNQQSCRISNIETVIEFQQMNSRLLEITREFSVN     240

241   AGVTTPLSTYMLTNSELLSLINDMPITNDQKKLMSSNVQIVRQQSYSIMSIIKEEVLAYV     300

301   VQLPIYGVIDTPCWKLHTSPLCTTNIKEGSNICLTRTDRGWYCDNAGSVSFFPQADTCKV     360

361   QSNRVFCDTMNSLTLPSEVSLCNTDIFNSKYDCKIMTSKTDISSSVITSLGAIVSCYGKT     420

421   KCTASNKNRGIIKTFSNGCDYVSNKGVDTVSVGNTLYYVNKLEGKNLYVKGEPIINYYDP     480

481   LVFPSDEFDASISQVNEKINQSLAFIRRSDELLHNVNTGKSTTNIMITTIIIVIIVVLLS     540

541   LIAIGLLLYCKAKNTPVTLSKDQLSGINNIAFSK                               574
```

RSV proteins may contain one or more mutations that prevent cleavage at one or both of the furin cleavage sites replacement of any such lysine or arginine residue with an amino acid other than lysine or arginine. For example, lysine and/or arginine residues in the p27 region (about amino acids 110-136 of SEQ ID NOS: 1 or 2) can be substituted or deleted, including deletion of the p27 region in whole or in part.

Alternatively or in addition to the furin-cleavage mutations, RSV F polypeptides or proteins may contain one or more mutations in the fusion peptide region (amino acids 137 and 153 of SEQ ID NOS: 1 or 2). For example, this region can be deleted in whole or in part.

In particular embodiments, the sequence of amino acid residue 100-150 of the RSV protein, such as SEQ ID NO:1, SEQ ID NO:2, or the soluble ecto domains thereof, is

```
(Fusion peptide deletion 1)
                                              (SEQ ID NO: 11)
TPATNNRARRELPRFMNYTLNNAKKTNVTLSKKRKRR---------SAI AS,
or (Fusion peptide deletion 2)
                                              (SEQ ID NO: 12)
TPATNNRARRELPRFMNYTLNNAKKTNVTLSKKRKRR------GVGSAI

AS.
```

In addition to furin-cleavage and fusion peptide mutations, or alternatively, soluble RSV proteins, such as those that lack the transmembrane region and cytoplasmic tail, RSV proteins may contain one or more oligomerization sequences. When an oligomerization sequence is present, it is preferably a trimerization sequence. Suitable oligomerization sequences are well known in the art and include, for example, the coiled coil of the yeast GCN4 leucine zipper protein, trimerizing sequence from bacteriophage T4 fibritin ("foldon"), and the trimer domain of influenza HA. These and other suitable oligomerization sequences are described in greater detail herein.

Proteins, or fragments thereof, will usually be prepared by expression in a recombinant host system. Generally, they (e.g., RSV proteins) are produced by expression of recombinant constructs that encode the proteins in suitable recombinant host cells, although any suitable methods can be used. Suitable recombinant host cells include, for example, insect cells (e.g., *Aedes aegypti, Autographa californica, Bombyx mori, Drosophila melanogaster, Spodoptera frugiperda*, and *Trichoplusia ni*), mammalian cells (e.g., human, non-human primate, horse, cow, sheep, dog, cat, and rodent (e.g., hamster), avian cells (e.g., chicken, duck, and geese), bacteria (e.g., *E. coli, Bacillus subtilis*, and *Streptococcus* spp.), yeast cells (e.g., *Saccharomyces cerevisiae, Candida albicans, Candida maltosa, Hansenual polymorpha, Kluyveromyces fragilis, Kluyveromyces lactis, Pichia guillerimondii, Pichia pastoris, Schizosaccharomyces pombe* and *Yarrowia lipolytica*), Tetrahymena cells (e.g., *Tetrahymena thermophila*) or combinations thereof. Many suitable insect cells and mammalian cells are well-known in the art. Suitable insect cells include, for example, Sf9 cells, Sf21 cells, Tn5 cells, Schneider S2 cells, and High Five cells (a clonal isolate derived from the parental *Trichoplusia ni* BTI-TN-5B1-4 cell line (Invitrogen)). Suitable mammalian cells include, for example, Chinese hamster ovary (CHO) cells, human embryonic kidney cells (HEK293 cells, typically transformed by sheared adenovirus type 5 DNA), NIH-3T3 cells, 293-T cells, Vero cells, HeLa cells, PERC.6 cells (ECACC deposit number 96022940), Hep G2 cells, MRC-5 (ATCC CCL-171), WI-38 (ATCC CCL-75), fetal rhesus lung cells (ATCC CL-160), Madin-Darby bovine kidney ("MDBK") cells, Madin-Darby canine kidney ("MDCK") cells (e.g., MDCK (NBL2), ATCC CCL34; or MDCK 33016, DSM ACC 2219), baby hamster kidney (BHK) cells, such as BHK21-F, HKCC cells, and the like. Suitable avian cells include, for example, chicken embryonic stem cells (e.g., EBx® cells), chicken embryonic fibroblasts, chicken embryonic germ cells, duck cells (e.g., AGE1.CR and AGE1.CR.pIX cell lines (ProBioGen) which are described, for example, in Vaccine 27:4975-4982 (2009) and WO2005/042728), EB66 cells, and the like.

Suitable insect cell expression systems, such as baculovirus systems, are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. Avian cell expression systems are also known to those of skill in the art and described in, e.g., U.S. Pat. Nos. 5,340,740; 5,656,479; 5,830,510; 6,114,168; and 6,500,668; European Patent No. EP 0787180B; European Patent Application No. EP03291813.8;WO 03/043415; and WO 03/076601. Similarly, bacterial and mammalian cell expression systems are also known in the art and described in, e.g., Yeast Genetic Engineering (Barr et al., eds., 1989) Butterworths, London.

Recombinant constructs encoding RSV proteins can be prepared in suitable vectors using conventional methods. A number of suitable vectors for expression of recombinant proteins in insect or mammalian cells are well-known and conventional in the art. Suitable vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals; and a signal sequence or leader sequence for targeting to the secretory pathway in a selected host cell (e.g., of mammalian origin or from a heterologous mammalian or non-mammalian species). For example, for expression in insect cells a suitable baculovirus expression vector, such as pFastBac (Invitrogen), is used to produce recombinant baculovirus particles. The baculovirus particles are amplified and used to infect insect cells to express recombinant protein. For expression in mammalian cells, a vector that will drive expression of the construct in the desired mammalian host cell (e.g., Chinese hamster ovary cells) is used.

RSV proteins can be purified using any suitable methods. For example, methods for purifying RSV proteins by immunoaffinity chromatography are known in the art. Ruiz-Arguello et al., J. Gen. Virol., 85:3677-3687 (2004). Suitable methods for purifying desired proteins including precipitation and various types of chromatography, such as hydrophobic interaction, ion exchange, affinity, chelating and size exclusion are well-known in the art. Suitable purification schemes can be created using two or more of these or other suitable methods. If desired, the RSV proteins can include a "tag" that facilitates purification, such as an epitope tag or a HIS tag. Such tagged proteins can conveniently be purified, for example from conditioned media, by chelating chromatography or affinity chromatography. Additional purification techniques include diafiltration and tangential flow filtration.

Proteins may include additional sequences in addition to the RSV sequences. For example, a polypeptide may include a sequence to facilitate purification (e.g., a poly-H is sequence with or without a linker). Similarly, for expression purposes, the natural leader peptide may be substituted for a different one.

In some embodiments, RSV proteins are delivered using alphavirus replicon particles (VRP). Any nucleotide sequence encoding a RSV protein can be used to produce the protein. As used herein, the term "alphavirus" has its conventional meaning in the art and includes various species such as Venezuelan equine encephalitis virus (VEE; e.g., Trinidad donkey, TC83CR, V3014 etc.), Semliki Forest virus (SFV), Sindbis virus, Ross River virus, Western equine encephalitis virus, Eastern equine encephalitis virus, Chikungunya virus, S.A. AR86 virus, Everglades virus, Mucambo virus, Barmah Forest virus, Middelburg virus, Pixuna virus, O'nyong-nyong virus, Getah virus, Sagiyama virus, Bebaru virus, Mayaro virus, Una virus, Aura virus, Whataroa virus, Banbanki virus, Kyzylagach virus, Highlands J virus, Fort Morgan virus, Ndumu virus, and Buggy Creek virus.

An "alphavirus replicon particle" (VRP) or "replicon particle" is an alphavirus replicon packaged with alphavirus structural proteins.

An "alphavirus replicon" (or "replicon") is an RNA molecule which can direct its own amplification in vivo in a target cell. The replicon encodes the polymerase(s) which catalyze RNA amplification (nsP1, nsP2, nsP3, nsP4) and contains cis RNA sequences required for replication which are recognized and utilized by the encoded polymerase(s). An alphavirus replicon typically contains the following ordered elements: 5' viral sequences required in cis for replication, sequences which encode biologically active alphavirus nonstructural proteins (nsP1, nsP2, nsP3, nsP4), 3' viral sequences required in cis for replication, and a polyadenylate tract. An alphavirus replicon also may contain one or more viral subgenomic "junction region" promoters directing the expression of heterologous nucleotide sequences, which may, in certain embodiments, be modified in order to increase or reduce viral transcription of the subgenomic fragment and heterologous sequence(s) to be expressed. Other control elements can be used, as described below.

Alphavirus replicons encoding one or more RSV proteins are used to produce VRPs. Such alphavirus replicons comprise sequences encoding one or more RSV proteins or fragments thereof. These sequences are operably linked to one or more suitable control element, such as a subgenomic promoter, an IRES (e.g., EMCV, EV71), and a viral 2A site, which can be the same or different. Any one or combination of suitable control elements can be used in any order.

The use of polycistronic vectors is an efficient way of providing nucleic acid sequences that encode two or more RSV proteins in desired relative amounts. In one example, a single subgenomic promoter is operably linked to two sequences encoding two different RSV proteins, and an IRES is positioned between the two coding sequences. In another example, two sequences that encode two different RSV proteins are operably linked to separate promoters. In still another example, the two sequences that encode two different RSV proteins are operably linked to a single promoter. The two sequences that encode two different RSV proteins are linked to each other through a nucleotide sequence encoding a viral 2A site, and thus encode a single amino acid chain that contain the amino acid sequences of both RSV proteins. The viral 2A site in this context is used to generate two RSV proteins from the original polyprotein.

Subgenomic Promoters

Subgenomic promoters, also known as junction region promoters can be used to regulate protein expression. Alphaviral subgenomic promoters regulate expression of alphaviral structural proteins. See Strauss and Strauss, "The alphaviruses: gene expression, replication, and evolution," Microbiol Rev. 1994 September; 58(3):491-562. A polynucleotide can comprise a subgenomic promoter from any alphavirus. When two or more subgenomic promoters are present, for example in a polycistronic polynucleotide, the promoters can be the same or different. For example, the subgenomic promoter can have the sequence CTCTCTACGGCTAACCTGAATGGA (SEQ ID NO:13). In certain embodiments, subgenomic promoters can be modified in order to increase or reduce viral transcription of the proteins. See U.S. Pat. No. 6,592,874.

Internal Ribosomal Entry Site (IRES)

In some embodiments, one or more control elements is an internal ribosomal entry site (IRES). An IRES allows multiple proteins to be made from a single mRNA transcript as ribosomes bind to each IRES and initiate translation in the absence of a 5"-cap, which is normally required to initiate translation. For example, the IRES can be obtained from the cloned genome of enterovirus 71 (EV71) or encephalomyocarditis virus (EMCV).

Viral 2A Site

The foot and mouth disease virus (FMDV) 2A protein is a short peptide that serves to separate the structural proteins of FMDV from a nonstructural protein (FMDV 2B). Early work on this peptide suggested that it acts as an autocatalytic protease, but other work (e.g., Donnelly et al., (2001), J. Gen. Virol. 82, 1013-1025) suggests that this short sequence and the following single amino acid of FMDV 2B (Gly) acts as a translational stop-start. Regardless of the precise mode of action, the sequence can be inserted between two polypeptides, and effect the production of multiple individual polypeptides from a single open reading frame. FMDV 2A sequences can be inserted between sequences encoding at least two RSV proteins, allowing for their synthesis as part of a single open reading frame. For example, the open reading frame may encode an RL11 protein and a UL119 protein separated by a sequence encoding a viral 2A site. A single mRNA is transcribed then, during the translation step, the RL11 and UL119 peptides are produced separately due to the activity of the viral 2A site. Any suitable viral 2A sequence may be used. Often, a viral 2A site comprises the consensus sequence Asp-Val/Ile-Glu-X-Asn-Pro-Gly-Pro, where X is any amino acid (SEQ ID NO:14). For example, the Foot and Mouth Disease Virus 2A peptide sequence is DVESNPGP (SEQ ID NO:15). See Trichas et al., "Use of the viral 2A peptide for bicistronic expression in transgenic mice," BMC Biol. 2008 Sep. 15; 6:40, and Halpin et al., "Self-processing 2A-polyproteins—a system for co-ordinate expression of multiple proteins in transgenic plants," Plant J. 1999 February; 17(4):453-9.

In some embodiments an alphavirus replicon is a chimeric replicon, such as a VEE-Sindbis chimeric replicon (VCR), a VEE strain TC83 replicon (TC83R), or a TC83—Sindbis chimeric replicon (TC83CR), or a VEE strain V3014 replicon. In some embodiments a VCR contains the packaging signal and 3' UTR from a Sindbis replicon in place of sequences in nsP3 and at the 3' end of the VEE replicon; see Perri et al., *J. Virol.* 77, 10394-403, 2003. In some embodiments, a TC83CR contains the packaging signal and 3' UTR from a Sindbis replicon in place of sequences in nsP3 and at the 3' end of aVEE strain TC83replicon.

Producing VRPs

Methods of preparing VRPs are well known in the art. In some embodiments an alphavirus is assembled into a VRP using a packaging cell. An "alphavirus packaging cell" (or "packaging cell") is a cell that contains one or more alphavirus structural protein expression cassettes and that produces recombinant alphavirus particles after introduction of an alphavirus replicon, eukaryotic layered vector initiation system (e.g., U.S. Pat. No. 5,814,482), or recombinant alphavirus particle. The one or more different alphavirus structural protein cassettes serve as "helpers" by providing the alphavirus structural proteins. An "alphavirus structural protein cassette" is an expression cassette that encodes one or more alphavirus structural proteins and comprises at least one and up to five copies (i.e., 1, 2, 3, 4, or 5) of an alphavirus replicase recognition sequence. Structural protein expression cassettes typically comprise, from 5' to 3', a 5' sequence which initiates transcription of alphavirus RNA, an optional alphavirus subgenomic region promoter, a nucleotide sequence encoding the alphavirus structural protein, a 3' untranslated region (which also directs RNA transcription), and a polyA tract. See, e.g., WO 2010/019437.

In one embodiment, two different alphavirus structural protein cassettes ("split" defective helpers) are used in a packaging cell to minimize recombination events which could produce a replication-competent virus. In some embodiments an alphavirus structural protein cassette encodes the capsid protein (C) but not either of the glycoproteins (E2 and E1). In some embodiments an alphavirus structural protein cassette encodes the capsid protein and either the E1 or E2 glycoproteins (but not both). In some embodiments, an alphavirus structural protein cassette encodes the E2 and E1 glycoproteins but not the capsid protein. In some embodiments an alphavirus structural protein cassette encodes the E1 or E2 glycoprotein (but not both) and not the capsid protein.

In some embodiments, VRPs are produced by the simultaneous introduction of replicons and helper RNAs into cells of various sources. Under these conditions, for example, BHKV or Vero cells ($1\times10^7$) are electroporated at, for example, 220 volts, 1000 µF, 2 manual pulses with 10 µg replicon RNA:6 µg defective helper Cap RNA:10 µg defective helper Gly RNA, VRP-containing supernatant or cells with associated VRPs is collected ~24 hours later. Replicons and/or helpers can also be introduced in DNA forms which launch suitable RNAs within the transfected cells.

A packaging cell may be a mammalian cell or a non-mammalian cell, such as an insect (e.g., SF9) or avian cell (e.g., a primary chick or duck fibroblast or fibroblast cell line). See U.S. Pat. No. 7,445,924. Avian sources of cells include, but are not limited to, avian embryonic stem cells such as EB66® (VIVALIS); chicken cells, including chicken embryonic stem cells such as EBx® cells, chicken embryonic fibroblasts, and chicken embryonic germ cells; duck cells such as the AGE1.CR and AGE1.CR.pIX cell lines (ProBioGen) which are described, for example, in Vaccine 27:4975-4982 (2009) and WO2005/042728; and geese cells. In some embodiments, a packaging cell is a primary duck fibroblast or duck retinal cell line, such as AGE.CR (PROBIOGEN).

Mammalian sources of cells for simultaneous nucleic acid introduction and/or packaging cells include, but are not limited to, human or non-human primate cells, including PerC6 (PER.C6) cells (CRUCELL N.V.), which are described, for example, in WO 01/38362 and WO 02/40665, as well as deposited under ECACC deposit number 96022940; MRC-5 (ATCC CCL-171); WI-38 (ATCC CCL-75); fetal rhesus lung cells (ATCC CL-160); human embryonic kidney cells (e.g., 293 cells, typically transformed by sheared adenovirus type 5 DNA); VERO cells from monkey kidneys; cells of horse, cow (e.g., MDBK cells), sheep, dog (e.g., MDCK cells from dog kidneys, ATCC CCL34 MDCK (NBL2) or MDCK 33016, deposit number DSM ACC 2219 as described in WO 97/37001); cat; and rodent (e.g., hamster cells such as BHK21-F, HKCC cells, or Chinese hamster ovary (CHO) cells), and may be obtained from a wide variety of developmental stages, including for example, adult, neonatal, fetal, and embryo.

In some embodiments a packaging cell is stably transformed with one or more structural protein expression cassette(s). Structural protein expression cassettes can be introduced into cells using standard recombinant DNA techniques, including transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun" methods, and DEAE- or calcium phosphate-mediated transfection. Structural protein expression cassettes typically are introduced into a host cell as DNA molecules, but can also be introduced as in vitro-transcribed RNA. Each expression cassette can be introduced separately or substantially simultaneously.

In some embodiments, stable alphavirus packaging cell lines are used to produce recombinant alphavirus particles. These are alphavirus-permissive cells comprising DNA cassettes expressing the defective helper RNA stably integrated into their genomes. See Polo et al., *Proc. Natl. Acad. Sci. USA* 96, 4598-603, 1999. For example, in one embodiment the helper RNAs are constitutively expressed but the alphavirus structural proteins are not, because the genes are under the control of an alphavirus subgenomic promoter (Polo et al., 1999). In another embodiment, the subgenomic promoter is not used in the helper RNAs to drive structural protein expression. Upon introduction of an alphavirus replicon into the genome of a packaging cell by transfection or VRP infection, replicase enzymes are produced and trigger expression of the capsid and glycoprotein genes on the helper RNAs, and output VRPs are produced. Introduction of the replicon can be accomplished by a variety of methods, including both transfection and infection with a seed stock of alphavirus replicon particles. The packaging cell is then incubated under conditions and for a time sufficient to produce packaged alphavirus replicon particles in the culture supernatant.

Thus, packaging cells allow VRPs to act as self-propagating viruses. This technology allows VRPs to be produced in much the same manner, and using the same equipment, as that used for live attenuated vaccines or other viral vectors that have producer cell lines available, such as replication-incompetent adenovirus vectors grown in cells expressing the adenovirus E1A and E1B genes.

In some embodiments, a two-step process is used: the first step comprises producing a seed stock of alphavirus replicon particles by transfecting a packaging cell with a plasmid DNA-based replicon. A much larger stock of replicon particles is then produced in a second step, by infecting a fresh culture of packaging cells with the seed stock. This infection can be performed using various multiplicities of infection (MOI), including a MOI=0.00001, 0.00005, 0.0001, 0.0005, 0.001, 0.005, 0.01, 0.05, 0.1, 0.5, 1.0, 3, 5, 10 or 20. In some embodiments infection is performed at a low MOI (e.g., less than 1). Over time, replicon particles can be harvested from packaging cells infected with the seed stock. In some embodiments, replicon particles can then be passaged in yet larger cultures of naive packaging cells by repeated low-multiplicity infection, resulting in commercial scale preparations with the same high titer.

Nucleic Acid Compositions

Recombinant nucleic acid molecules that encode one or more RSV proteins or fragments can be administered to induce production of the encoded RSV proteins or fragments and an immune response thereto. The recombinant nucleic acid can be based on any desired nucleic acid such as DNA (e.g., plasmid or viral DNA) or RNA, preferably self replicating RNA, and can be monocistronic or polycistronic. Any suitable DNA or RNA can be used as the nucleic acid vector that carries the open reading frames that encode RSV proteins or fragments thereof. Suitable nucleic acid vectors have the capacity to carry and drive expression of one or more RSV proteins or fragments. Such nucleic acid vectors are known in the art and include, for example, plasmids, DNA obtained from DNA viruses such as vaccinia virus vectors (e.g., NYVAC, see U.S. Pat. No. 5,494,807), adenovirus vectors, and poxvirus vectors (e.g., ALVAC canarypox vector, Sanofi Pasteur), and RNA obtained from suitable RNA viruses such as alphavirus. If desired, the recombinant nucleic acid molecule can be modified, e.g., contain modified nucleobases and or linkages as described further herein.

Recombinant nucleic acid molecules that are polycistronic provide the advantage of delivering sequences that encode two or more RSV proteins to a cell, and for example driving the expression of the RSV proteins at sufficient levels to result in the formation of a protein complex containing the two or more RSV proteins in vivo. Using this approach, two or more encoded RSV proteins that form a complex can be expressed at sufficient intracellular levels for the formation of RSV protein complexes. For example, the encoded RSV proteins or fragments thereof can be expressed at substantially the same level, or if desired, at different levels by selecting appropriate expression control sequences (e.g., promoters, IRES, 2A site etc.). This is a significantly more efficient way to produce protein complexes in vivo than by co-delivering two or more individual DNA molecules that encode different RSV to the same cell, which can be inefficient and highly variable. See, e.g., WO 2004/076645.

The "self-replicating" nucleic acids described herein are also referred to by the inventors and herein as "self-amplifying." It is intended that the terms self-replicating and self-amplifying have the same meaning The self-replicating RNA molecules of the invention are based on the genomic RNA of RNA viruses, but lack the genes encoding one or more structural proteins. The self-replicating RNA molecules are capable of being translated to produce nonstructural proteins of the RNA virus and RSV proteins encoded by the self-replicating RNA.

The self-replicating RNA generally contains at least one or more genes selected from the group consisting of viral replicase, viral proteases, viral helicases and other nonstructural viral proteins, and also comprise 5'- and 3'-end cis-active replication sequences, and a heterologous sequences that encodes one or more desired RSV proteins. A subgenomic promoter that directs expression of the heterologous sequence(s) can be included in the self-replicating RNA. If desired, a heterologous sequence may be fused in frame to other coding regions in the self-replicating RNA and/or may be under the control of an internal ribosome entry site (IRES).

Self-replicating RNA molecules of the invention can be designed so that the self-replicating RNA molecule cannot induce production of infectious viral particles. This can be achieved, for example, by omitting one or more viral genes encoding structural proteins that are necessary for the production of viral particles in the self-replicating RNA. For example, when the self-replicating RNA molecule is based on an alpha virus, such as Sinbis virus (SIN), Semliki forest virus and Venezuelan equine encephalitis virus (VEE), one or more genes encoding viral structural proteins, such as capsid and/or envelope glycoproteins, can be omitted. If desired, self-replicating RNA molecules of the invention can be designed to induce production of infectious viral particles that are attenuated or virulent, or to produce viral particles that are capable of a single round of subsequent infection.

A self-replicating RNA molecule can, when delivered to a vertebrate cell even without any proteins, lead to the production of multiple daughter RNAs by transcription from itself (or from an antisense copy of itself). The self-replicating RNA can be directly translated after delivery to a cell, and this translation provides a RNA-dependent RNA polymerase which then produces transcripts from the delivered RNA. Thus the delivered RNA leads to the production of multiple daughter RNAs. These transcripts are antisense relative to the delivered RNA and may be translated themselves to provide in situ expression of encoded RSV protein, or may be transcribed to provide further transcripts with the same sense as the delivered RNA which are translated to provide in situ expression of the encoded RSV protein(s).

One suitable system for achieving self-replication is to use an alphavirus-based RNA replicon, such as an alphavirus replicon as described herein. These + stranded replicons are translated after delivery to a cell to give off a replicase (or replicase-transcriptase). The replicase is translated as a polyprotein which auto cleaves to provide a replication complex which creates genomic – strand copies of the + strand delivered RNA. These – strand transcripts can themselves be transcribed to give further copies of the + stranded parent RNA and also to give a subgenomic transcript which encodes two or more RSV proteins. Translation of the subgenomic transcript thus leads to in situ expression of the RSV protein(s) by the infected cell. Suitable alphavirus replicons can use a replicase from a sindbis virus, a semliki forest virus, an eastern equine encephalitis virus, a venezuelan equine encephalitis virus, etc.

A preferred self-replicating RNA molecule thus encodes (i) a RNA-dependent RNA polymerase which can transcribe RNA from the self-replicating RNA molecule and (ii) one or more RSV proteins or fragments thereof. The polymerase can be an alphavirus replicase e.g. comprising alphavirus protein nsP4.

Whereas natural alphavirus genomes encode structural virion proteins in addition to the non structural replicase polyprotein, it is preferred that an alphavirus based self-replicating RNA molecule of the invention does not encode all alphavirus structural proteins. Thus the self replicating RNA can lead to the production of genomic RNA copies of itself in a cell, but not to the production of RNA-containing alphavirus virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self replicating RNAs of the invention and their place is taken by gene(s) encoding the desired gene product (RSV protein or fragment thereof), such that the subgenomic transcript encodes the desired gene product rather than the structural alphavirus virion proteins.

Thus a self-replicating RNA molecule useful with the invention has one or more sequences that encode RSV proteins or fragments thereof. The sequences encoding the RSV proteins or fragments can be in any desired orientation, and can be operably linked to the same or separate promoters. If desired, the sequences encoding the RSV proteins or fragments can be part of a single open reading frame. In some embodiments the RNA may have one or more additional (downstream) sequences or open reading frames e.g. that encode other additional RSV proteins or fragments thereof. A self-replicating RNA molecule can have a 5' sequence which is compatible with the encoded replicase.

In one aspect, the self-replicating RNA molecule is derived from or based on an alphavirus, such as an alphavirus replicon as defined herein. In other aspects, the self-replicating RNA molecule is derived from or based on a virus other than an alphavirus, preferably, a positive-stranded RNA virus, and more preferably a picornavirus, flavivirus, rubivirus, pestivirus, hepacivirus, calicivirus, or coronavirus. Suitable wild-type alphavirus sequences are well-known and are available from sequence depositories, such as the American Type Culture Collection, Rockville, Md. Representative examples of suitable alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro virus (ATCC VR-66; ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

The self-replicating RNA molecules of the invention can contain one or more modified nucleotides and therefore have improved stability and be resistant to degradation and clearance in vivo, and other advantages. Without wishing to be bound by any particular theory, it is believed that self-replicating RNA molecules that contain modified nucleotides avoid or reduce stimulation of endosomal and cytoplasmic immune receptors when the self-replicating RNA is delivered into a cell. This permits self-replication, amplification and expression of protein to occur. This also reduces safety concerns relative to self-replicating RNA that does not contain modified nucleotides, because the self-replicating RNA that contains modified nucleotides reduces activation of the innate immune system and subsequent undesired consequences (e.g., inflammation at injection site, irritation at injection site, pain, and the like). It is also believed that the RNA molecules produced as a result of self-replication are recognized as foreign nucleic acids by the cytoplasmic immune receptors. Thus, self-replicating RNA molecules that contain modified nucleotides provide for efficient amplification of the RNA in a host cell and expression of CMV gB proteins, as well as adjuvant effects.

As used herein, "modified nucleotide" refers to a nucleotide that contains one or more chemical modifications (e.g., substitutions) in or on the nitrogenous base of the nucleoside (e.g., cytosine (C), thymine (T) or uracil (U)), adenine (A) or guanine (G)). If desired, a self replicating RNA molecule can contain chemical modifications in or on the sugar moiety of the nucleoside (e.g., ribose, deoxyribose, modified ribose, modified deoxyribose, six-membered sugar analog, or open-chain sugar analog), or the phosphate.

The self-replicating RNA molecules can contain at least one modified nucleotide, that preferably is not part of the 5' cap. Accordingly, the self-replicating RNA molecule can contain a modified nucleotide at a single position, can contain a particular modified nucleotide (e.g., pseudouridine, N6-methyladenosine, 5-methylcytidine, 5-methyluridine) at two or more positions, or can contain two, three, four, five, six, seven, eight, nine, ten or more modified nucleotides (e.g., each at one or more positions). Preferably, the self-replicating RNA molecules comprise modified nucleotides that contain a modification on or in the nitrogenous base, but do not contain modified sugar or phosphate moieties.

In some examples, between 0.001% and 99% or 100% of the nucleotides in a self-replicating RNA molecule are modified nucleotides. For example, 0.001%-25%, 0.01%-25%, 0.1%-25%, or 1%-25% of the nucleotides in a self-replicating RNA molecule are modified nucleotides.

In other examples, between 0.001% and 99% or 100% of a particular unmodified nucleotide in a self-replicating RNA molecule is replaced with a modified nucleotide. For example, about 1% of the nucleotides in the self-replicating RNA molecule that contain uridine can be modified, such as by replacement of uridine with pseudouridine. In other examples, the desired amount (percentage) of two, three, or four particular nucleotides (nucleotides that contain uridine, cytidine, guanosine, or adenine) in a self-replicating RNA molecule are modified nucleotides. For example, 0.001%-25%, 0.01%-25%, 0.1%-25, or 1%-25% of a particular nucleotide in a self-replicating RNA molecule are modified nucleotides. In other examples, 0.001%-20%, 0.001%-15%, 0.001%-10%, 0.01%-20%, 0.01%-15%, 0.1%-25, 0.01%-10%, 1%-20%, 1%-15%, 1%-10%, or about 5%, about 10%, about 15%, about 20% of a particular nucleotide in a self-replicating RNA molecule are modified nucleotides.

It is preferred that less than 100% of the nucleotides in a self-replicating RNA molecule are modified nucleotides. It is also preferred that less than 100% of a particular nucleotide in a self-replicating RNA molecule are modified nucleotides. Thus, preferred self-replicating RNA molecules comprise at least some unmodified nucleotides.

There are more than 96 naturally occurring nucleoside modifications found on mammalian RNA. See, e.g., Limbach et al., Nucleic Acids Research, 22(12):2183-2196 (1994). The preparation of nucleotides and modified nucleotides and nucleosides are well-known in the art, e.g. from U.S. Pat. Nos. 4,373,071, 4,458,066, 4,500,707, 4,668,777, 4,973,679, 5,047,524, 5,132,418, 5,153,319, 5,262,530, 5,700,642 all of which are incorporated herein by reference in their entirety, and many modified nucleosides and modified nucleotides are commercially available.

Modified nucleobases which can be incorporated into modified nucleosides and modified nucleotides and be present in the self-replicating RNA molecules include m5C (5-methylcytidine), m5U (5-methyluridine), m6A (N6-methyladenosine), s2U (2-thiouridine), Um (2'-0-methyluridine), m1A (1-methyl adenosine); m2A (2-methyladenosine); Am (2-1-O-methyladenosine); ms2 m6A (2-methylthio-N6-methyladenosine); i6A (N6-isopentenyladenosine); ms2i6A (2-methylthio-N6 isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6- threonylcarbamoyladenosine); hn6A (N6.-hydroxynorvalylcarbamoyl adenosine); ms2hn6A (2-methylthio-N6-hydroxynorvalyl carbamoyladenosine); Ar(p) (2'-β-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C(N4-acetylcytidine); f5C (5-formylcytidine); m5 Cm (5,2-O-dimethylcytidine); ac4 Cm (N4-acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-β-dimethylguanosine); m22Gm (N2,N2,2'-O-trimethylguanosine); Gr(p) (2'-β-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluricjine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-Omethyluridine); cmnm5s2U (5-carboxymethylaminomethyl-2-thiouridine); m62A (N6, N6-dimethyladenosine); Tm (2'-O-methylinosine); m4C (N4-methylcytidine); m4 Cm (N4,2-O-dimethylcytidine); hm5C (5-hydroxymethylcytidine); m3U (3-methyluridine); cm5U (5-carboxymethyluridine); m6 Am (N6,T-O-dimethyladenosine); rn62 Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5 Cm (5-formyl-2'-O-methylcytidine); m1Gm (1,2'-O-dimethylguanosine); m'Am (1,2-O-dimethyl adenosine)irinomethyluridine); tm5s2U (S-taurinomethyl-2-thiouridine)); imG-14 (4-demethyl guanosine); imG2 (isoguanosine); or ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-($C_1$-$C_6$)-alkyluracil, 5-methyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-methylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 7-deazaguanine, 8-azaguanine, 7-deaza-7-substituted guanine, 7-deaza-7-(C2-C6) alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, and hydrogen (abasic residue). m5C, m5U, m6A, s2U, W, or 2'-O-methyl-U. Any one or any combination of these modified nucleobases may be included in the self-replicating RNA of the invention. Many of these modified nucleobases and their corresponding ribonucleosides are available from commercial suppliers.

If desired, the self-replicating RNA molecule can contain phosphoramidate, phosphorothioate, and/or methylphosphonate linkages.

Self-replicating RNA molecules that comprise at least one modified nucleotide can be prepared using any suitable method. Several suitable methods are known in the art for producing RNA molecules that contain modified nucleotides. For example, a self-replicating RNA molecule that contains modified nucleotides can be prepared by transcribing (e.g., in vitro transcription) a DNA that encodes the self-replicating RNA molecule using a suitable DNA-dependent RNA polymerase, such as T7 phage RNA polymerase, SP6 phage RNA polymerase, T3 phage RNA polymerase, and the like, or mutants of these polymerases which allow efficient incorporation of modified nucleotides into RNA molecules. The transcription reaction will contain nucleotides and modified nucleotides, and other components that support the activity of the selected polymerase, such as a suitable buffer, and suitable salts. The incorporation of nucleotide analogs into a self-replicating RNA may be engineered, for example, to alter the stability of such RNA molecules, to increase resistance against RNases, to establish replication after introduction into appropriate host cells ("infectivity" of the RNA), and/or to induce or reduce innate and adaptive immune responses.

Suitable synthetic methods can be used alone, or in combination with one or more other methods (e.g., recombinant DNA or RNA technology), to produce a self-replicating RNA molecule that contain one or more modified nucleotides. Suitable methods for de novo synthesis are well-known in the art and can be adapted for particular applications. Exemplary methods include, for example, chemical synthesis using suitable protecting groups such as CEM (Masuda et al., (2007) *Nucleic Acids Symposium Series* 51:3-4), the β-cyanoethyl phosphoramidite method (Beaucage S L et al. (1981) *Tetrahedron Lett* 22:1859); nucleoside H-phosphonate method (Garegg P et al. (1986) *Tetrahedron Lett* 27:4051-4; Froehler B C et al. (1986) *Nucl Acid Res* 14:5399-407; Garegg P et al. (1986) *Tetrahedron Lett* 27:4055-8; Gaffney B L et al. (1988) *Tetrahedron Lett* 29:2619-22). These chemistries can be performed or adapted for use with automated nucleic acid synthesizers that are commercially available. Additional suitable synthetic methods are disclosed in Uhlmann et al. (1990) *Chem Rev* 90:544-84, and Goodchild J (1990) *Bioconjugate Chem* 1: 165. Nucleic acid synthesis can also be performed using suitable recombinant methods that are well-known and conventional in the art, including cloning, processing, and/or expression of polynucleotides and gene products encoded by such polynucleotides. DNA shuffling by random fragmentation and PCR reassembly of gene fragments and synthetic polynucleotides are examples of known techniques that can be used to design and engineer polynucleotide sequences. Site-directed mutagenesis can be used to alter nucleic acids and the encoded proteins, for example, to insert new restriction sites, alter glycosylation patterns, change codon preference, produce splice variants, introduce mutations and the like. Suitable methods for transcription, translation and expression of nucleic acid sequences are known and conventional in the art. (See generally, Current Protocols in Molecular Biology, Vol. 2, Ed. Ausubel, et al., Greene Publish. Assoc. & Wiley Interscience, Ch. 13, 1988; Glover, DNA Cloning, Vol. II, IRL Press, Wash., D.C., Ch. 3, 1986; Bitter, et al., in Methods in Enzymology 153:516-544 (1987); The Molecular Biology of the Yeast *Saccharomyces*, Eds. Strathern et al., Cold Spring Harbor Press, Vols. I and II, 1982; and Sambrook et al., Molecular Cloning: A Laboratory Manual, Cold Spring Harbor Press, 1989.)

The presence and/or quantity of one or more modified nucleotides in a self-replicating RNA molecule can be determined using any suitable method. For example, a self-replicating RNA can be digested to monophosphates (e.g., using nuclease P1) and dephosphorylated (e.g., using a suitable phosphatase such as CIAP), and the resulting nucleosides analyzed by reversed phase HPLC (e.g., using a YMC Pack ODS-AQ column (5 micron, 4.6×250 mm) and eluted using a gradient, 30% B (0-5 min) to 100% B (5-13 min) and at 100% B (13-40) min, flow Rate (0.7 ml/min), UV detection (wavelength: 260 nm), column temperature (30° C.). Buffer A (20 mM acetic acid-ammonium acetate pH 3.5), buffer B (20 mM acetic acid-ammonium acetate pH 3.5/methanol [90/10])).

The self-replicating RNA may be associated with a delivery system. The self-replicating RNA may be administered with or without an adjuvant.

RNA Delivery Systems

The self-replicating RNA described herein are suitable for delivery in a variety of modalities, such as naked RNA delivery or in combination with lipids, polymers or other compounds that facilitate entry into the cells. Self-replicating RNA molecules can be introduced into target cells or subjects using any suitable technique, e.g., by direct injection, microinjection, electroporation, lipofection, biolystics, and the like. The self-replicating RNA molecule may also be introduced into cells by way of receptor-mediated endocytosis. See e.g., U.S. Pat. No. 6,090,619; Wu and Wu, J. Biol. Chem., 263:14621 (1988); and Curiel et al., Proc. Natl. Acad. Sci. USA, 88:8850 (1991). For example, U.S. Pat. No. 6,083,741 discloses introducing an exogenous nucleic acid into mammalian cells by associating the nucleic acid to a polycation moiety (e.g., poly-L-lysine having 3-100 lysine residues (SEQ ID NO: 19)), which is itself coupled to an integrin receptor-binding moiety (e.g., a cyclic peptide having the sequence Arg-Gly-Asp (SEQ ID NO:16).

The self-replicating RNA molecules can be delivered into cells via amphiphiles. See e.g., U.S. Pat. No. 6,071,890. Typically, a nucleic acid molecule may form a complex with the cationic amphiphile. Mammalian cells contacted with the complex can readily take it up.

The self-replicating RNA can be delivered as naked RNA (e.g. merely as an aqueous solution of RNA) but, to enhance entry into cells and also subsequent intercellular effects, the self-replicating RNA is preferably administered in combination with a delivery system, such as a particulate or emulsion delivery system. A large number of delivery systems are well known to those of skill in the art. Such delivery systems include, for example liposome-based delivery (Debs and Zhu (1993) WO 93/24640; Mannino and Gould-Fogerite (1988) BioTechniques 6(7): 682-691; Rose U.S. Pat. No. 5,279,833; Brigham (1991) WO 91/06309; and Felgner et al. (1987) Proc. Natl. Acad. Sci. USA 84: 7413-7414), as well as use of viral vectors (e.g., adenoviral (see, e.g., Berns et al. (1995) Ann. NY Acad. Sci. 772: 95-104; Ali et al. (1994) Gene Ther. 1: 367-384; and Haddada et al. (1995) Curr. Top. Microbiol. Immunol. 199 (Pt 3): 297-306 for review), papillomaviral, retroviral (see, e.g., Buchscher et al. (1992) J. Virol. 66(5) 2731-2739; Johann et al. (1992) J. Virol. 66 (5): 1635-1640 (1992); Sommerfelt et al., (1990) Virol. 176:58-59; Wilson et al. (1989) J. Virol. 63:2374-2378; Miller et al., J. Virol. 65:2220-2224 (1991); Wong-Staal et al., PCT/US94/05700, and Rosenburg and Fauci (1993) in Fundamental Immunology, Third Edition Paul (ed) Raven Press, Ltd., New York and the references therein, and Yu et al., Gene Therapy (1994) supra.), and adeno-associated viral vectors (see, West et al. (1987) Virology 160:38-47; Carter et al. (1989) U.S. Pat. No. 4,797,368; Carter et al. WO 93/24641 (1993); Kotin (1994) Human Gene Therapy 5:793-801; Muzyczka (1994) J. Clin. Invst. 94:1351 and Samulski (supra) for an overview of AAV vectors; see also, Lebkowski, U.S. Pat. No. 5,173,414; Tratschin et al. (1985) Mol. Cell. Biol. 5(11):3251-3260; Tratschin, et al. (1984) Mol. Cell. Biol., 4:2072-2081; Hermonat and Muzyczka (1984) Proc. Natl. Acad. Sci. USA, 81:6466-6470; McLaughlin et al. (1988) and Samulski et al. (1989) *J. Virol.*, 63:03822-3828), and the like.

Three particularly useful delivery systems are (i) liposomes, (ii) non-toxic and biodegradable polymer microparticles, and (iii) cationic submicron oil-in-water emulsions.

Liposomes

Various amphiphilic lipids can form bilayers in an aqueous environment to encapsulate a RNA-containing aqueous core as a liposome. These lipids can have an anionic, cationic or zwitterionic hydrophilic head group. Formation of liposomes from anionic phospholipids dates back to the 1960s, and cationic liposome-forming lipids have been studied since the 1990s. Some phospholipids are anionic whereas other are zwitterionic. Suitable classes of phospholipid include, but are not limited to, phosphatidylethanolamines, phosphatidylcholines, phosphatidylserines, and phosphatidylglycerols. Useful cationic lipids include, but are not limited to, dioleoyl trimethylammonium propane (DOTAP), 1,2-distearyloxy-N,N-dimethyl-3-aminopropane (DSDMA), 1,2-dioleyloxy-N,Ndimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA). Zwitterionic lipids include, but are not limited to, acyl zwitterionic lipids and ether zwitterionic lipids. Examples of useful zwitterionic lipids are DPPC, DOPC and dodecylphosphocholine. The lipids can be saturated or unsaturated.

Liposomes can be formed from a single lipid or from a mixture of lipids. A mixture may comprise (i) a mixture of anionic lipids (ii) a mixture of cationic lipids (iii) a mixture of zwitterionic lipids (iv) a mixture of anionic lipids and cationic lipids (v) a mixture of anionic lipids and zwitterionic lipids (vi) a mixture of zwitterionic lipids and cationic lipids or (vii) a mixture of anionic lipids, cationic lipids and zwitterionic lipids. Similarly, a mixture may comprise both saturated and unsaturated lipids. For example, a mixture may comprise DSPC (zwitterionic, saturated), DlinDMA (cationic, unsaturated), and/or DMPG (anionic, saturated). Where a mixture of lipids is used, not all of the component lipids in the mixture need to be amphiphilic e.g. one or more amphiphilic lipids can be mixed with cholesterol.

The hydrophilic portion of a lipid can be PEGylated (i.e. modified by covalent attachment of a polyethylene glycol). This modification can increase stability and prevent non-specific adsorption of the liposomes. For instance, lipids can be conjugated to PEG using techniques such as those disclosed in Heyes et al. (2005) *J Controlled Release* 107: 276-87.

A mixture of DSPC, DlinDMA, PEG-DMPG and cholesterol can be used to form liposomes. A separate aspect of the invention is a liposome comprising DSPC, DlinDMA, PEG- DMG and cholesterol. This liposome preferably encapsulates RNA, such as a self-replicating RNA e.g. encoding an immunogen.

Liposomes are usually divided into three groups: multilamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core; SUVs typically have a diameter ≤50 nm, and LUVs have a diameter >50 nm. Liposomes useful with of the invention are ideally LUVs with a diameter in the range of 50-220 nm. For a composition comprising a population of LUVs with different diameters: (i) at least 80% by number should have diameters in the range of 20-220 nm, (ii) the average diameter (Zav, by intensity) of the population is ideally in the range of 40-200 nm, and/or (iii) the diameters should have a polydispersity index <0.2.

Techniques for preparing suitable liposomes are well known in the art e.g. see Liposomes: Methods and Protocols, Volume 1: Pharmaceutical Nanocarriers: Methods and Protocols. (ed. Weissig). Humana Press, 2009. ISBN 160327359X; Liposome Technology, volumes I, II & III. (ed. Gregoriadis). Informa Healthcare, 2006; and Functional Polymer Colloids and Microparticles volume 4 (Microspheres, microcapsules & liposomes). (eds. Arshady & Guyot). Citus Books, 2002. One useful method involves mixing (i) an ethanolic solution of the lipids (ii) an aqueous solution of the nucleic acid and (iii) buffer, followed by mixing, equilibration, dilution and purification (Heyes et al. (2005) *J Controlled Release* 107:276-87.).

RNA is preferably encapsulated within the liposomes, and so the liposome forms a outer layer around an aqueous RNA-containing core. This encapsulation has been found to protect RNA from RNase digestion. The liposomes can include some external RNA (e.g. on the surface of the liposomes), but preferably, at least half of the RNA (and ideally substantially all of it) is encapsulated.

Polymeric Microparticles

Various polymers can form microparticles to encapsulate or adsorb RNA. The use of a substantially non-toxic polymer means that a recipient can safely receive the particles, and the use of a biodegradable polymer means that the particles can be metabolised after delivery to avoid long-term persistence. Useful polymers are also sterilisable, to assist in preparing pharmaceutical grade formulations.

Suitable non-toxic and biodegradable polymers include, but are not limited to, poly(α-hydroxy acids), polyhydroxy butyric acids, polylactones (including polycaprolactones), polydioxanones, polyvalerolactone, polyorthoesters, polyanhydrides, polycyanoacrylates, tyrosine-derived polycarbonates, polyvinyl-pyrrolidinones or polyester-amides, and combinations thereof.

In some embodiments, the microparticles are formed from poly(α-hydroxy acids), such as a poly(lactides) ("PLA"), copolymers of lactide and glycolide such as a poly(D,L-lactide-co-glycolide) ("PLG"), and copolymers of D,L-lactide and caprolactone. Useful PLG polymers include those having a lactide/glycolide molar ratio ranging, for example, from 20:80 to 80:20 e.g. 25:75, 40:60, 45:55, 55:45, 60:40, 75:25. Useful PLG polymers include those having a molecular weight between, for example, 5,000-200,000 Da e.g. between 10,000-100,000, 20,000-70,000, 40,000-50,000 Da.

The microparticles ideally have a diameter in the range of 0.02 μm to 8 μm. For a composition comprising a population of microparticles with different diameters at least 80% by number should have diameters in the range of 0.03-7 μm.

Techniques for preparing suitable microparticles are well known in the art e.g. see Functional Polymer Colloids and Microparticles volume 4 (Microspheres, microcapsules & liposomes). (eds. Arshady & Guyot). Citus Books, 2002; *Polymers in Drug Delivery*. (eds. Uchegbu & Schatzlein). CRC Press, 2006. (in particular chapter 7) and *Microparticulate Systems for the Delivery of Proteins and Vaccines*. (eds. Cohen & Bernstein). CRC Press, 1996. To facilitate adsorption of RNA, a microparticle may include a cationic surfactant and/or lipid e.g. as disclosed in O'Hagan et al. (2001) *J Virology* 75:9037-9043; and Singh et al. (2003) *Pharmaceutical Research* 20: 247-251. An alternative way of making polymeric microparticles is by molding and curing e.g. as disclosed in WO2009/132206.

Microparticles of the invention can have a zeta potential of between 40-100 mV. RNA can be adsorbed to the microparticles, and adsorption is facilitated by including cationic materials (e.g. cationic lipids) in the microparticle.

Oil-in-Water Cationic Emulsions

Oil-in-water emulsions are known for adjuvanting influenza vaccines e.g. the MF59™ adjuvant in the FLUAD™ product, and the AS03 adjuvant in the PREPANDRIX™ product. RNA delivery can be accomplished with the use of an oil-in-water emulsion, provided that the emulsion includes one or more cationic molecules. For instance, a cationic lipid can be included in the emulsion to provide a positively charged droplet surface to which negatively-charged RNA can attach.

The emulsion comprises one or more oils. Suitable oil(s) include those from, for example, an animal (such as fish) or a vegetable source. The oil is ideally biodegradable (metabolizable) and biocompatible. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and so may be used. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Squalane, the saturated analog to squalene, can also be used. Fish oils, including squalene and squalane, are readily available from commercial sources or may be obtained by methods known in the art.

Other useful oils are the tocopherols, particularly in combination with squalene. Where the oil phase of an emulsion includes a tocopherol, any of the α, β, γ, δ, ε or ξ tocopherols can be used, but α-tocopherols are preferred. D-α-tocopherol and DL-α-tocopherol can both be used. A preferred α-tocopherol is DL-α-tocopherol. An oil combination comprising squalene and a tocopherol (e.g. DL-α-tocopherol) can be used.

Preferred emulsions comprise squalene, a shark liver oil which is a branched, unsaturated terpenoid ($C_{30}H_{50}$; [($CH_3$)$_2$C[=$CHCH_2CH_2C(CH_3)$]$_2$=$CHCH_2$—]$_2$; 2,6,10,15,19,23-hexamethyl-2,6,10,14,18,22-tetracosahexaene; CAS RN 7683-64-9).

The oil in the emulsion may comprise a combination of oils e.g. squalene and at least one further oil.

The aqueous component of the emulsion can be plain water (e.g. w.f.i.) or can include further components e.g. solutes. For instance, it may include salts to form a buffer e.g. citrate or phosphate salts, such as sodium salts. Typical buffers include: a phosphate buffer; a Tris buffer; a borate buffer; a succinate buffer; a histidine buffer; or a citrate buffer. A buffered aqueous phase is preferred, and buffers will typically be included in the 5-20 mM range.

The emulsion also includes a cationic lipid. Preferably this lipid is a surfactant so that it can facilitate formation and stabilization of the emulsion. Useful cationic lipids generally contains a nitrogen atom that is positively charged under physiological conditions e.g. as a tertiary or quaternary amine. This nitrogen can be in the hydrophilic head group of an amphiphilic surfactant. Useful cationic lipids include, but are not limited to: 1,2-dioleoyloxy-3-(trimethylammonio) propane (DOTAP), 3'-[N—(N',N'-Dimethylaminoethane)-carbamoyl]Cholesterol (DC Cholesterol), dimethyldioctadecyl-ammonium (DDA e.g. the bromide), 1,2-Dimyristoyl-3-Trimethyl-AmmoniumPropane (DMTAP), dipalmitoyl (C16:0)trimethyl ammonium propane (DPTAP), distearoyltrimethylammonium propane (DSTAP). Other useful cationic lipids are: benzalkonium chloride (BAK), benzethonium chloride, cetramide (which contains tetradecyltrimethylammonium bromide and possibly small amounts of dedecyltrimethylammonium bromide and hexadecyltrimethyl ammonium bromide), cetylpyridinium chloride (CPC), cetyl trimethylammonium chloride (CTAC), N,N',N'-polyoxyethylene (10) —N-tallow-1,3-diaminopropane, dodecyltrimethylammonium bromide, hexadecyltrimethyl-ammonium bromide, mixed alkyl-trimethyl-ammonium bromide, benzyldimethyldodecylammonium chloride, benzyldimethylhexadecyl-ammonium chloride, benzyltrimethylammonium methoxide, cetyldimethylethylammonium bromide, dimethyldioctadecyl ammonium bromide (DDAB), methylbenzethonium chloride, decamethonium chloride, methyl mixed trialkyl ammonium chloride, methyl trioctylammonium chloride), N,N-dimethyl-N-[2 (2-methyl-4-(1,1,3,3tetramethylbutyl)-phenoxy]-ethoxy)ethyl]-benzenemetha-naminium chloride (DEBDA), dialkyldimethyl-ammonium salts, [1-(2,3-dioleyloxy)-propyl]-N,N,N, trimethylammonium chloride, 1,2-diacyl-3-(trimethylammonio) propane (acyl group=dimyristoyl, dipalmitoyl, distearoyl, dioleoyl), 1,2-diacyl-3 (dimethyl-ammonio)propane (acyl group=dimyristoyl, dipalmitoyl, distearoyl, dioleoyl), 1,2-dioleoyl-3-(4'-trimethyl-ammonio) butanoyl-sn-glycerol, 1,2-dioleoyl 3-succinyl-sn-glycerol choline ester, cholesteryl (4'-trimethylammonio) butanoate), N-alkyl pyridinium salts (e.g. cetylpyridinium bromide and cetylpyridinium chloride), N-alkylpiperidinium salts, dicationic bolaform electrolytes (C12Me6; C12BU6), dialkylglycetylphosphorylcholine, lysolecithin, L-α dioleoylphosphatidylethanolamine, cholesterol hemisuccinate choline ester, lipopolyamines, including but not limited to dioctadecylamidoglycylspermine (DOGS), dipalmitoyl phosphatidylethanol-amidospermine (DPPES), lipopoly-L (or D)-lysine (LPLL, LPDL), poly (L (or D)-lysine conjugated to N-glutarylphosphatidylethanolamine, didodecyl glutamate ester with pendant amino group (C^GluPhCnN), ditetradecyl glutamate ester with pendant amino group (Cl4GIuCnN+), cationic derivatives of cholesterol, including but not limited to cholesteryl-3 β-oxysuccinamidoethylenetrimethylammonium salt, cholesteryl-3 β-oxysuccinamidoethylene-dimethylamine, cholesteryl-3 β-carboxyamidoethylenetrimethylammonium salt, and cholesteryl-3 β-carboxyamidoethylenedimethylamine. Other useful cationic lipids are described in US 2008/0085870 and US 2008/0057080, which are incorporated herein by reference. The cationic lipid is preferably biodegradable (metabolizable) and biocompatible.

In addition to the oil and cationic lipid, an emulsion can include a non-ionic surfactant and/or a zwitterionic surfactant. Such surfactants include, but are not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy(oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether; and sorbitan esters (commonly known as the Spans), such as sorbitan trioleate (Span 85) and sorbitan monolaurate. Preferred surfactants for including in the emulsion are polysorbate 80 (Tween 80; polyoxyethylene sorbitan monooleate), Span 85 (sorbitan trioleate), lecithin and Triton X-100.

Mixtures of these surfactants can be included in the emulsion e.g. Tween 80/Span 85 mixtures, or Tween 80/Triton-X100 mixtures. A combination of a polyoxyethylene sorbitan ester such as polyoxyethylene sorbitan monooleate (Tween 80) and an octoxynol such as t-octylphenoxy-polyethoxyethanol (Triton X-100) is also suitable. Another useful combination comprises laureth 9 plus a polyoxyethylene sorbitan ester and/or an octoxynol. Useful mixtures can comprise a surfactant with a HLB value in the range of 10-20 (e.g. polysorbate 80, with a HLB of 15.0) and a surfactant with a HLB value in the range of 1-10 (e.g. sorbitan trioleate, with a HLB of 1.8).

Preferred amounts of oil (% by volume) in the final emulsion are between 2-20% e.g. 5-15%, 6-14%, 7-13%, 8-12%. A squalene content of about 4-6% or about 9-11% is particularly useful.

Preferred amounts of surfactants (% by weight) in the final emulsion are between 0.001% and 8%. For example: polyoxyethylene sorbitan esters (such as polysorbate 80) 0.2 to 4%, in particular between 0.4-0.6%, between 0.45-0.55%, about 0.5% or between 1.5-2%, between 1.8-2.2%, between 1.9-2.1%, about 2%, or 0.85-0.95%, or about 1%; sorbitan esters (such as sorbitan trioleate) 0.02 to 2%, in particular about 0.5% or about 1%; octyl- or nonylphenoxy polyoxyethanols (such as Triton X-100) 0.001 to 0.1%, in particular 0.005 to 0.02%; polyoxyethylene ethers (such as laureth 9) 0.1 to 8%, preferably 0.1 to 10% and in particular 0.1 to 1% or about 0.5%.

The absolute amounts of oil and surfactant, and their ratio, can be varied within wide limits while still forming an emulsion. A skilled person can easily vary the relative proportions of the components to obtain a desired emulsion, but a weight ratio of between 4:1 and 5:1 for oil and surfactant is typical (excess oil).

An important parameter for ensuring immunostimulatory activity of an emulsion, particularly in large animals, is the oil droplet size (diameter). The most effective emulsions have a droplet size in the submicron range. Suitably the droplet sizes will be in the range 50-750 nm. Most usefully the average droplet size is less than 250 nm e.g. less than 200 nm, less than 150 nm. The average droplet size is usefully in the range of 80-180 nm. Ideally, at least 80% (by number) of the emulsion's oil droplets are less than 250 nm in diameter, and preferably at least 90%. Apparatuses for determining the average droplet size in an emulsion, and the size distribution, are commercially available. These typically use the techniques of dynamic light scattering and/or single-particle optical sensing e.g. the Accusizer™ and Nicomp™ series of instruments available from Particle Sizing Systems (Santa Barbara, USA), or the Zetasizer™ instruments from Malvern Instruments (UK), or the Particle Size Distribution Analyzer instruments from Horiba (Kyoto, Japan).

Ideally, the distribution of droplet sizes (by number) has only one maximum i.e. there is a single population of droplets distributed around an average (mode), rather than having two maxima. Preferred emulsions have a polydispersity of <0.4 e.g. 0.3, 0.2, or less.

Suitable emulsions with submicron droplets and a narrow size distribution can be obtained by the use of microfluidization. This technique reduces average oil droplet size by propelling streams of input components through geometrically fixed channels at high pressure and high velocity. These streams contact channel walls, chamber walls and each other. The results shear, impact and cavitation forces cause a reduction in droplet size. Repeated steps of microfluidization can be performed until an emulsion with a desired droplet size average and distribution are achieved.

As an alternative to microfluidization, thermal methods can be used to cause phase inversion. These methods can also provide a submicron emulsion with a tight particle size distribution.

Preferred emulsions can be filter sterilized i.e. their droplets can pass through a 220 nm filter. As well as providing a sterilization, this procedure also removes any large droplets in the emulsion.

In certain embodiments, the cationic lipid in the emulsion is DOTAP. The cationic oil-in-water emulsion may comprise from about 0.5 mg/ml to about 25 mg/ml DOTAP. For example, the cationic oil-in-water emulsion may comprise DOTAP at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.6 mg/ml, from about 0.7 mg/ml to about 1.6 mg/ml, from about 0.8 mg/ml to about 1.6 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 12 mg/ml, about 18 mg/ml, about 20 mg/ml, about 21.8 mg/ml, about 24 mg/ml, etc. In an exemplary embodiment, the cationic oil-in-water emulsion comprises from about 0.8 mg/ml to about 1.6 mg/ml DOTAP, such as 0.8 mg/ml, 1.2 mg/ml, 1.4 mg/ml or 1.6 mg/ml.

In certain embodiments, the cationic lipid is DC Cholesterol. The cationic oil-in-water emulsion may comprise DC Cholesterol at from about 0.1 mg/ml to about 5 mg/ml DC Cholesterol. For example, the cationic oil-in-water emulsion may comprise DC Cholesterol from about 0.1 mg/ml to about 5 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.62 mg/ml to about 5 mg/ml, from about 1 mg/ml to about 5 mg/ml, from about 1.5 mg/ml to about 5 mg/ml, from about 2 mg/ml to about 5 mg/ml, from about 2.46 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, from about 0.1 mg/ml to about 4.92 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.46 mg/ml, from about 0.1 mg/ml to about 2 mg/ml, from about 0.1 mg/ml to about 1.5 mg/ml, from about 0.1 mg/ml to about 1 mg/ml, from about 0.1 mg/ml to about 0.62 mg/ml, about 0.15 mg/ml, about 0.3 mg/ml, about 0.6 mg/ml, about 0.62 mg/ml, about 0.9 mg/ml, about 1.2 mg/ml, about 2.46 mg/ml, about 4.92 mg/ml, etc. In an exemplary embodiment, the cationic oil-in-water emulsion comprises from about 0.62 mg/ml to about 4.92 mg/ml DC Cholesterol, such as 2.46 mg/ml.

In certain embodiments, the cationic lipid is DDA. The cationic oil-in-water emulsion may comprise from about 0.1 mg/ml to about 5 mg/ml DDA. For example, the cationic oil-in-water emulsion may comprise DDA at from about 0.1 mg/ml to about 5 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.5 mg/ml, from about 0.1 mg/ml to about 2 mg/ml, from about 0.1 mg/ml to about 1.5 mg/ml, from about 0.1 mg/ml to about 1.45 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.6 mg/ml to about 5 mg/ml, from about 0.73 mg/ml to about 5 mg/ml, from about 0.8 mg/ml to about 5 mg/ml, from about 0.9 mg/ml to about 5 mg/ml, from about 1.0 mg/ml to about 5 mg/ml, from about 1.2 mg/ml to about 5 mg/ml, from about 1.45 mg/ml to about 5 mg/ml, from about 2 mg/ml to about 5 mg/ml, from about 2.5 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, about 1.2 mg/ml, about 1.45 mg/ml, etc. Alternatively, the cationic oil-in-water emulsion may comprise DDA at about 20 mg/ml, about 21 mg/ml, about 21.5 mg/ml, about 21.6 mg/ml, about 25 mg/ml. In an exemplary embodiment, the cationic oil-in-water emulsion comprises from about 0.73 mg/ml to about 1.45 mg/ml DDA, such as 1.45 mg/ml.

Catheters or like devices may be used to deliver the self-replicating RNA molecules of the invention, as naked RNA or in combination with a delivery system, into a target organ or tissue. Suitable catheters are disclosed in, e.g., U.S. Pat. Nos. 4,186,745; 5,397,307; 5,547,472; 5,674,192; and 6,129,705, all of which are incorporated herein by reference.

The present invention includes the use of suitable delivery systems, such as liposomes, polymer microparticles or submicron emulsion microparticles with encapsulated or adsorbed self-replicating RNA, to deliver a self-replicating RNA molecule that encodes two or more RSV proteins, for example, to elicit an immune response alone, or in combination with another macromolecule. The invention includes liposomes, microparticles and submicron emulsions with adsorbed and/or encapsulated self-replicating RNA molecules, and combinations thereof.

The self-replicating RNA molecules associated with liposomes and submicron emulsion microparticles can be effectively delivered to a host cell, and can induce an immune response to the protein encoded by the self-replicating RNA.

Polycistronic self replicating RNA molecules that encode RSV proteins, and VRPs produced using polycistronic alphavirus replicons, can be used to form RSV protein complexes in a cell. In some embodiments combinations of VRPs or VRPs that contain sequences encoding two or more RSV proteins or fragments are delivered to a cell. In some embodiments combinations of self-replicating RNA molecules or self replicating RNA molecules that encode two or more RSV proteins or fragments are delivered to a cell.

The Anti-RSV Immune Response Inducing Composition

The anti-RSV immune response inducing compositions may comprise one or more immunoregulatory agents. Preferably, one or more of the immunoregulatory agents include one or more adjuvants, for example two, three, four or more adjuvants. The adjuvants may include a TH1 adjuvant and/or a TH2 adjuvant, further discussed below.

The compositions of the invention may include one or more pharmaceutically acceptable carrier(s) and/or excipient(s), including adjuvants. A thorough discussion of such components is available in Gennaro (2000) *Remington: The Science and Practice of Pharmacy.* 20th edition, ISBN: 0683306472. Compositions will generally be in aqueous form.

The composition may include preservatives such as thiomersal or 2-phenoxyethanol. It is preferred, however, that the vaccine should be substantially free from (i.e., less than 5 μg/ml) mercurial material, e.g., thiomersal-free. Immunogenic compositions containing no mercury are more preferred. Preservative-free immunogenic compositions are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, and the like.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range. The pH of a composition will generally be between 5.0 and 8.1, and more typically between 6.0 and 8.0, e.g., between 6.5 and 7.5, or between 7.0 and 7.8. A process of the invention may therefore include a step of adjusting the pH of the bulk vaccine prior to packaging.

The composition is preferably sterile. The composition is preferably non-pyrogenic, e.g., containing <1 EU (endotoxin unit, a standard measure) per dose, and preferably <0.1 EU per dose. The composition is preferably gluten free. Human vaccines are typically administered in a dosage volume of about 0.5 ml, although a half dose (i.e., about 0.25 ml) may be administered to children.

Compositions of the invention, that contain RSV-F polypeptides, or nucleic acids that encode RSV-F polypeptides, may also include one or more adjuvants, for example two, three, four or more adjuvants, which can function to enhance the immune responses (humoral and/or cellular) elicited in a patient who receives the composition. The adjuvants may include a TH1 adjuvant and/or a TH2 adjuvant. Adjuvants which may be used in compositions of the invention include, but are not limited to:

Mineral-containing compositions. Mineral-containing compositions suitable for use as adjuvants in the invention include mineral salts, such as calcium salts and aluminum salts (or mixtures thereof). The invention includes mineral salts such as hydroxides (e.g. oxyhydroxides), phosphates (e.g. hydroxyphosphates, orthophosphates), sulphates, etc., or mixtures of different mineral compounds, with the compounds taking any suitable form (e.g. gel, crystalline, amorphous, etc.), and with adsorption being preferred. Calcium salts include calcium phosphate (e.g., the "CAP" particles disclosed in U.S. Pat. No. 6,355,271). Aluminum salts include hydroxides, phosphates, sulfates, and the like. The mineral containing compositions may also be formulated as a particle of metal salt (WO00/23105). Aluminum salt adjuvants are described in more detail below.

Oil emulsion compositions (see in more detail below). Oil emulsion compositions suitable for use as adjuvants in the invention include squalene-water emulsions, such as MF59 (5% Squalene, 0.5% Tween 80 and 0.5% Span, formulated into submicron particles using a microfluidizer).

Cytokine-inducing agents (see in more detail below). Cytokine-inducing agents suitable for use in the invention include toll-like receptor 7 (TLR7) agonists (e.g. benzonaphthyridine compounds disclosed in WO 2009/111337.

Saponins (chapter 22 of *Vaccine Design: The Subunit and Adjuvant Approach* (eds. Powell & Newman) Plenum Press 1995 (ISBN 0-306-44867-X)), which are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as STIMULON™. Saponin compositions have been purified using HPLC and RP-HPLC. Specific purified fractions using these techniques have been identified, including QS7, QS 17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (WO96/33739). Combinations of saponins and cholesterols can be used to form unique particles called immunostimulating complexes (ISCOMs) (chapter 23 of *Vaccine Design: The Subunit and Adjuvant Approach* (eds. Powell & Newman) Plenum Press 1995 (ISBN 0-306-44867-X)). ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in WO96/337391, EP-A-0109942, and WO96/11711. Optionally, the ISCOMS may be devoid of additional detergent (WO00/07621). A review of the development of saponin based adjuvants can be found in Barr et al. (1998) *Advanced Drug Delivery Reviews* 32:247-271 and Sjolanderet et al. (1998) *Advanced Drug Delivery Reviews* 32:321-338.

Fatty adjuvants (see in more detail below), including oil-in-water emulsions, modified natural lipid As derived from enterobacterial lipopolysaccharides, phospholipid compounds (such as the synthetic phospholipid dimer, E6020) and the like.

Bacterial ADP-ribosylating toxins (e.g., the *E. coli* heat labile enterotoxin "LT", cholera toxin "CT", or pertussis toxin "PT") and detoxified derivatives thereof, such as the mutant toxins known as LT-K63 and LT-R72 (Pizza et al. (2000) *Int J Med Microbiol* 290:455-461). The use of detoxified ADP-ribosylating toxins as mucosal adjuvants is described in WO95/17211 and as parenteral adjuvants in WO98/42375.

Bioadhesives and mucoadhesives, such as esterified hyaluronic acid microspheres (Singh et at (2001) *J Cont Release* 70:267-276) or chitosan and its derivatives (WO99/27960).

Microparticles (i.e., a particle of ~100 nm to ~150 μm in diameter, more preferably ~200 nm to ~30 μm in diameter, or ~500 nm to ~10 μm in diameter) formed from materials that are biodegradable and non-toxic (e.g., a poly(α-hydroxy acid), a polyhydroxybutyric acid, a polyorthoester, a polyanhydride, a polycaprolactone, and the like), with poly(lactide-co-glycolide) being preferred, optionally treated to have a negatively-charged surface (e.g., with SDS) or a positively-charged surface (e.g., with a cationic detergent, such as CTAB).

Liposomes (Chapters 13 & 14 of *Vaccine Design: The Subunit and Adjuvant Approach* (eds. Powell & Newman) Plenum Press 1995 (ISBN 0-306-44867-X)). Examples of liposome formulations suitable for use as adjuvants are described in U.S. Pat. Nos. 6,090,406, 5,916,588 and EP-A-0626169.

Polyoxyethylene ethers and polyoxyethylene esters (WO99/52549). Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

Muramyl peptides, such as N-acetylmuramyl-L-threonyl-D-isoglutamine ("thr-MDP"), N-acetyl-normuramyl-L-alanyl-D-isoglutamine (nor-MDP), N-acetylglucsaminyl-N-acetylmuramyl-L-Al-D-isoglu-L-Ala-dipalmitoxy propylamide ("DTP-DPP", or "Theramide™"), N-acetylmuramyl-L-alanyl-D-isoglutaminyl-L-alanine-2-(1'-2' dipalmitoyl-sn-glycero-3-hydroxyphosphoryloxy)-ethylamine ("MTP-PE").

An outer membrane protein proteosome preparation prepared from a first Gram-negative bacterium in combination with a liposaccharide preparation derived from a second Gram-negative bacterium, wherein the outer membrane protein proteosome and liposaccharide preparations form a stable non-covalent adjuvant complex. Such complexes include "IVX-908", a complex comprised of *Neisseria meningitidis* outer membrane and lipopolysaccharides.

A polyoxidonium polymer (Dyakonova et al. (2004) *Int Immunopharmacol* 4(13):1615-23, FR-2859633) or other N-oxidized polyethylene-piperazine derivative.

Methyl inosine 5'-monophosphate ("MIMP") (Signorelli & Hadden (2003) *Int Immunopharmacol* 3(8):1177-86).

A polyhydroxlated pyrrolizidine compound (WO2004/064715), such as one having formula:

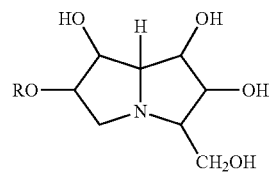

where R is selected from the group comprising hydrogen, straight or branched, unsubstituted or substituted, saturated or unsaturated acyl, alkyl (e.g., cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, and the like A CD1d ligand, such as an α-glycosylceramide (De Libero et al, (2005) *Nature Reviews Immunology* 5:485-496; U.S. Pat. No. 5,936,076; Old et al., *J Clin Investig*, 113:1631-1640; US2005/0192248; Yang et al. (2004) *Angew Chem Int Ed* 43:3818-3822; WO2005/102049; Goffet et at (2004) *Am Chem Soc* 126:13602-13603; WO03/105769) (e.g., α-galactosylceramide), phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-O-sulfo-galactosylceramide, etc.

A gamma inulin (Cooper (1995) *Pharm Biotechnol* 6:559-80) or derivative thereof, such as algammulin.

Virosomes and virus-like particles (VLPs). These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1).

These and other adjuvant-active substances are discussed in more detail in *Vaccine Design: The Subunit and Adjuvant Approach* (eds. Powell & Newman) Plenum Press 1995 (ISBN 0-306-44867-X) and *Vaccine Adjuvants: Preparation Methods and Research Protocols* (Volume 42 of *Methods in Molecular Medicine* series). ISBN: 1-59259-083-7. Ed. O'Hagan.

Compositions may include two, three, four or more adjuvants. For example, compositions of the invention may advantageously include both an oil-in-water emulsion and a cytokine-inducing agent, or both a mineral-containing composition and a cytokine-inducing agent, or two oil-in-water emulsion adjuvants, or two benzonaphthyridine compounds, etc.

Antigens and adjuvants in a composition will typically be in admixture.

Oil Emulsion Adjuvants

Oil emulsion compositions suitable for use as adjuvants in the invention include squalene-water emulsions, such as MF59 (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

Various oil-in-water emulsions are known, and they typically include at least one oil and at least one surfactant, with the oil(s) and surfactant(s) being biodegradable (metabolizable) and biocompatible. The oil droplets in the emulsion are generally less than 5 μm in diameter, and may even have a sub-micron diameter, with these small sizes being achieved with a microfluidizer to provide stable emulsions. Droplets with a size less than 220 nm are preferred as they can be subjected to filter sterilization.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used, e.g., obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoid known as squalene, 2,6,10,15,19,23-hexamethyl-2,6,10,14,18,22-tetracosahexaene, which is particularly preferred herein. Squalane, the saturated analog to squalene, is also preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy(oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the TERGITOL™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are TWEEN 80™ (polyoxyethylene sorbitan monooleate), Span 85 (sorbitan trioleate), lecithin and Triton X-100.

Mixtures of surfactants can be used e.g., TWEEN 80™/Span 85 mixtures. A combination of a polyoxyethylene sorbitan ester such as polyoxyethylene sorbitan monooleate (TWEEN 80™) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as TWEEN 80™) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants useful with the invention include, but are not limited to: A submicron emulsion of squalene, TWEEN 80™, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' (WO90/14837; Podda & Del Giudice (2003) *Expert Rev Vaccines* 2:197-203; Podda (2001) *Vaccine* 19: 2673-2680), as described in more detail in Chapter 10 of *Vaccine Design The Subunit and Adjuvant Approach* (eds. Powell & Newman) Plenum Press 1995 (ISBN 0-306-44867-X) and chapter 12 of *Vaccine Adjuvants: Preparation Methods and Research Protocols* (Volume 42 of *Methods in Molecular Medicine* series). ISBN: 1-59259-083-7. Ed. O'Hagan. The MF59 emulsion advantageously includes citrate ions, e.g., 10 mM sodium citrate buffer.

An emulsion of squalene, a tocopherol, and TWEEN 80™. The emulsion may include phosphate buffered saline. It may also include Span 85 (e.g., at 1%) and/or lecithin. These emulsions may have from 2 to 10% squalene, from 2 to 10% tocopherol and from 0.3 to 3% TWEEN 80™, and the weight ratio of squalene:tocopherol is preferably <1 as this provides a more stable emulsion. Squalene and TWEEN 80™ may be present volume ratio of about 5:2. One such emulsion can be made by dissolving TWEEN 80™ in PBS to give a 2% solution, then mixing 90 ml of this solution with a mixture of (5g of DL-α-tocopherol and 5 ml squalene), then microfluidizing the mixture. The resulting emulsion may have submicron oil droplets, e.g., with an average diameter of between 100 and 250 nm, preferably about 180 nm.

An emulsion of squalene, a tocopherol, and a Triton detergent (e.g., Triton X-100). The emulsion may also include a 3d-MPL (see below). The emulsion may contain a phosphate buffer.

An emulsion comprising a polysorbate (e.g., polysorbate 80), a Triton detergent (e.g., Triton X-100) and a tocopherol (e.g., an α-tocopherol succinate). The emulsion may include these three components at a mass ratio of about 75:11:10 (e.g., 750 µg/ml polysorbate 80, 110 µg/ml Triton X-100 and 100 µg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("PLURONIC™ L121"). The emulsion can be formulated in phosphate buffered saline, pH 7.4. This emulsion is a useful delivery vehicle for muramyl dipeptides, and has been used with threonyl-MDP in the "SAF-1" adjuvant (Allison & Byars (1992) *Res Immunol* 143:519-25) (0.05-1% Thr-MDP, 5% squalane, 2.5% Pluronic L121 and 0.2% polysorbate 80). It can also be used without the Thr-MDP, as in the "AF" adjuvant (Hariharan et al. (1995) *Cancer Res* 55:3486-9) (5% squalane, 1.25% Pluronic L121 and 0.2% polysorbate 80). Microfluidization is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm. The emulsion may also include one or more of: alditol; a cryoprotective agent (e.g. a sugar, such as dodecylmaltoside and/or sucrose); and/or an alkylpolyglycoside. Such emulsions may be lyophilized.

An emulsion having from 0.5-50% of an oil, 0.1-10% of a phospholipid, and 0.05-5% of a non-ionic surfactant. As described in reference WO95/1 1700, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolizable oil (such as light mineral oil) and at least one surfactant (such as lecithin, TWEEN 80™ or Span 80). Additives may be included, such as QuilA saponin, cholesterol, a saponin-lipophile conjugate (such as GPI-0100, described in U.S. Pat. No. 6,080,725, produced by addition of aliphatic amine to desacylsaponin via the carboxyl group of glucuronic acid), dimethyldioctadecylammonium bromide and/or N,N-dioctadecyl-N,N-bis(2-hydroxyethyl)propanediamine.

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer).

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer).

An emulsion in which a saponin (e.g., QuilA or QS21) and a sterol (e.g., a cholesterol) are associated as helical micelles (WO2005/097181).

The emulsions may be mixed with antigen extemporaneously, at the time of delivery. Thus the adjuvant and antigen may be kept separately in a packaged or distributed vaccine, ready for final formulation at the time of use. The antigen will generally be in an aqueous form, such that the vaccine is finally prepared by mixing two liquids. The volume ratio of the two liquids for mixing can vary (e.g., between 5:1 and 1:5) but is generally about 1:1.

Cytokine-Inducing Agents

Cytokine-inducing agents for inclusion in compositions of the invention are able, when administered to a patient, to elicit the immune system to release cytokines, including interferons and interleukins. Preferred agents can elicit the release of one or more of: interferon-γ; interleukin-1; interleukin-2; interleukin-12; TNF-α; TNF-β; and GM-CSF. Preferred agents elicit the release of cytokines associated with a Th1-type immune response, e.g., interferon-γ, TNF-α, interleukin-2 Stimulation of both interferon-γ and interleukin-2 is preferred.

As a result of receiving a composition of the invention, therefore, a patient will have T cells that, when stimulated with a RSV F protein, will release the desired cytokine(s) in an antigen-specific manner. For example, T cells purified from their blood will release γ-interferon when exposed in vitro to F protein. Methods for measuring such responses in peripheral blood mononuclear cells (PBMC) are known in the art, and include ELISA, ELISPOT, flow-cytometry and real-time PCR. For example, Tassignon et al. (2005) *J Immunol Meth* 305:188-98 reports a study in which antigen-specific T cell-mediated immune responses against tetanus toxoid, specifically γ-interferon responses, were monitored, and found that ELISPOT was the most sensitive method to discriminate antigen-specific TT-induced responses from spontaneous responses, but that intracytoplasmic cytokine detection by flow cytometry was the most efficient method to detect re-stimulating effects.

Suitable cytokine-inducing agents include, but are not limited to:

An immunostimulatory oligonucleotide, such as one containing a CpG motif (a dinucleotide sequence containing an unmethylated cytosine linked by a phosphate bond to a guanosine), or a double-stranded RNA, or an oligonucleotide containing a palindromic sequence, or an oligonucleotide containing a poly(dG) sequence.

3-O-deacylated monophosphoryl lipid A ('3dMPL', also known as 'MPL™') (Myers et al. (1990) pages 145-156 of *Cellular and molecular aspects of endotoxin reactions*; Ulrich (2000) *Chapter* 16 (pages 273-282) of *Vaccine Adjuvants: Preparation Methods and Research Protocols* (Volume 42 of *Methods in Molecular Medicine* series). ISBN: 1-59259-083-7. Ed. O'Hagan; Johnson et al. (1999) *J Med Chem* 42:4640-9; Baldrick et al. (2002) *Regulatory Toxicol Pharmacol* 35:398-413).

An imidazoquinoline compound, such as IMIQUIMOD™ ("R-837") (U.S. Pat. Nos. 4,680,338, 4,988,815), RESIQUIMOD™ ("R-848") (WO92/15582), and their analogs; and salts thereof (e.g., the hydrochloride salts). Further details about immunostimulatory imidazoquinolines can be found in Stanley (2002) *Clin Exp Dermatol* 27:57 1-577; Wu et al. (2004) *Antiviral Res.* 64(2):79-83; Vasilakos et al. (2000) *Cell Immunol.* 204(1):64-74; U.S. Pat. Nos. 4,689,338, 4,929,624, 5,238,944, 5,266,575, 5,268,376, 5,346,905, 5,352, 784, 5,389,640, 5,395,937, 5,482,936, 5,494,916, 5,525,612, 6,083,505, 6,440,992, 6,627,640, 6,664, 264, 6,664,265, 6,667,312, 6,677,347, 6,677,348, 6,677,349, 6,683,088, 6,703,402, 6,743,920, 6,800, 624, 6,809,203, 6,888,000, and 6,924,293; and Jones (2003) *Curr Opin Investig Drugs* 4:214-218.

A benzonaphthyridine compound, such as: (a) a compound having the formula:

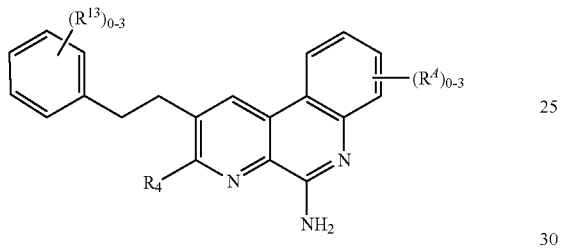

wherein:
R$^4$ is selected from H, halogen, —C(O)OR$^7$, —C(O)R$^7$, —C(O)N(R$^{11}$R$^{12}$), —N(R$^{11}$R$^{12}$), —N(R$^9$)$_2$, —NHN(R$^9$)$_2$, —SR$^7$, —(CH$_2$)$_n$OR$^7$, —(CH$_2$)$_n$R$^7$, -LR$^8$, -LR$^{10}$, —OLR$^8$, —OLR$^{10}$, C$_1$-C$_6$alkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, aryl, heteroaryl, C$_3$-C$_8$cycloalkyl, and C$_3$-C$_8$heterocycloalkyl, wherein the C$_1$-C$_6$alkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, aryl, heteroaryl, C$_3$-C$_8$cycloalkyl, and C$_3$-C$_8$heterocycloalkyl groups of R$^4$ are each optionally substituted with 1 to 3 substituents independently selected from halogen, —CN, —NO$_2$, —R$^7$, —OR$^8$, —C(O)R$^8$, —OC(O)R$^8$, —C(O)OR$^8$, —N(R$^9$)$_2$, —P(O)(OR$^8$)$_2$, —OP(O)(OR$^8$)$_2$, —P(O)(OR$^{10}$)$_2$, —OP(O)(OR$^{10}$)$_2$, —C(O)N(R$^9$)$_2$, —S(O)$_2$R$^8$, —S(O)R$^8$, —S(O)$_2$N(R$^9$)$_2$, and —NR$^9$S(O)$_2$R$^8$;

each L is independently selected from a bond, —(O(CH$_2$)$_m$)$_t$—, C$_1$-C$_6$alkyl, C$_2$-C$_6$alkenylene and C$_2$-C$_6$alkynylene, wherein the C$_1$-C$_6$alkyl, C$_2$-C$_6$alkenylene and C$_2$-C$_6$alkynylene of L are each optionally substituted with 1 to 4 substituents independently selected from halogen, —R$^8$, —OR$^8$, —N(R$^9$)$_2$, —P(O)(OR$^8$)$_2$, —OP(O)(OR$^8$)$_2$, —P(O)(OR$^{10}$)$_2$, and —OP(O)(OR$^{10}$)$_2$;

R$^7$ is selected from H, C$_1$-C$_6$alkyl, aryl, heteroaryl, C$_3$-C$_8$cycloalkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, and C$_3$-C$_8$heterocycloalkyl, wherein the C$_1$-C$_6$alkyl, aryl, heteroaryl, C$_3$-C$_8$cycloalkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, and C$_3$-C$_8$heterocycloalkyl groups of R$^7$ are each optionally substituted with 1 to 3 R$^{13}$ groups;

each R$^8$ is independently selected from H, —CH(R$^{10}$)$_2$, C$_1$-C$_8$alkyl, C$_2$-C$_8$alkene, C$_2$-C$_8$alkyne, C$_1$-C$_6$haloalkyl, C$_1$-C$_6$alkoxy, C$_1$-C$_6$heteroalkyl, C$_3$-C$_8$cycloalkyl, C$_2$-C$_8$heterocycloalkyl, C$_1$-C$_6$hydroxyalkyl and C$_1$-C$_6$haloalkoxy, wherein the C$_1$-C$_8$alkyl, C$_2$-C$_8$alkene, C$_2$-C$_8$alkyne, C$_1$-C$_6$heteroalkyl, C$_1$-C$_6$haloalkyl, C$_1$-C$_6$alkoxy, C$_3$-C$_8$cycloalkyl, C$_2$-C$_8$heterocycloalkyl, C$_1$-C$_6$hydroxyalkyl and C$_1$-C$_6$haloalkoxy groups of R$^8$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)N(R$^9$)$_2$, —C(O)OR$^{11}$, —NR$^9$C(O)R$^{11}$, —NR$^9$R$^{10}$, —NR$^{11}$R$^{12}$, —N(R$^9$)$_2$, —OR$^9$, —OR$^{10}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;

each R$^9$ is independently selected from H, —C(O)R$^8$, —C(O)OR$^8$, —C(O)R$^{10}$, —C(O)OR$^{10}$, —S(O)$_2$R$^{10}$, —C$_1$-C$_6$ alkyl, C$_1$-C$_6$ heteroalkyl and C$_3$-C$_6$ cycloalkyl, or each R$^9$ is independently a C$_1$-C$_6$alkyl that together with N they are attached to form a C$_3$-C$_8$heterocycloalkyl, wherein the C$_3$-C$_8$heterocycloalkyl ring optionally contains an additional heteroatom selected from N, O and S, and wherein the C$_1$-C$_6$ alkyl, C$_1$-C$_6$ heteroalkyl, C$_3$-C$_6$ cycloalkyl, or C$_3$-C$_8$heterocycloalkyl groups of R$^9$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)OR$^{11}$, —NR$^{11}$R$^{12}$, —C(O)NR$^{11}$R$^{12}$, —C(O)NR OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;

each R$^{10}$ is independently selected from aryl, C$_3$-C$_8$cycloalkyl, C$_3$-C$_8$heterocycloalkyl and heteroaryl, wherein the aryl, C$_3$-C$_8$cycloalkyl, C$_3$-C$_8$heterocycloalkyl and heteroaryl groups are optionally substituted with 1 to 3 substituents selected from halogen, —R$^8$, —OR$^8$, -LR$^9$, -LOR$^9$, —N(R$^9$)$_2$, —NR$^9$C(O)R$^8$, —NR$^9$CO$_2$R$^8$, —CO$_2$R$^8$, —C(O)R$^8$ and —C(O)N(R$^9$)$_2$;

R$^{11}$ and R$^{12}$ are independently selected from H, C$_1$-C$_6$alkyl, C$_1$-C$_6$heteroalkyl, C$_1$-C$_6$haloalkyl, aryl, heteroaryl, C$_3$-C$_8$cycloalkyl, and C$_3$-C$_8$heterocycloalkyl, wherein the C$_1$-C$_6$alkyl, C$_1$-C$_6$heteroalkyl, C$_1$-C$_6$haloalkyl, aryl, heteroaryl, C$_3$-C$_8$cycloalkyl, and C$_3$-C$_8$heterocycloalkyl groups of R$^{11}$ and R$^{12}$ are each optionally substituted with 1 to 3 substituents independently selected from halogen, —CN, R$^8$, —OR$^8$, —C(O)R$^8$, ⁻OC(O)R$^8$, —C(O)OR$^8$, —N(R$^9$)$_2$, —NR$^8$C(O)R$^8$, —NR$^8$C(O)OR$^8$, —C(O)N(R$^9$)$_2$, C$_3$-C$_8$heterocycloalkyl, —S(O)$_2$R$^8$, —S(O)$_2$N(R$^9$)$_2$, —NR$^9$S(O)$_2$R$^8$, C$_1$-C$_6$haloalkyl and C$_1$-C$_6$haloalkoxy;

or R$^{11}$ and R$^{12}$ are each independently C$_1$-C$_6$alkyl and taken together with the N atom to which they are attached form an optionally substituted C$_3$-C$_8$heterocycloalkyl ring optionally containing an additional heteroatom selected from N, O and S;

each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -$LC(O)R^8$, —$OLC(O)R^8$, -$LC(O)OR^8$, -$LC(O)R^{10}$, -$LOC(O)OR^8$, -$LC(O)NR^9R^{11}$, -$LC(O)NR^9R^8$, -$LN(R^9)_2$, -$LNR^9R^8$, -$LNR^9R^{10}$, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, -$LS(O)_2N(R^9)_2$, —$OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{10})_2$ and —$OLP(O)(OR^{10})_2$;

each $R^A$ is independently selected from —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)_nCO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, —$C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —CH=$CHCO_2R^8$, —C(=NH)—$N(R^9)_2$, and —$(CH_2)_nNHC(O)R^8$; or two adjacent $R^A$ substituents on Ring A form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8; (b) a compound having the formula:

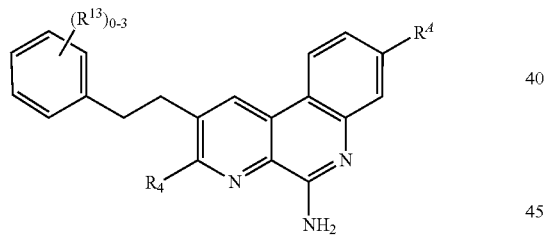

wherein:
$R^4$ is selected from H, halogen, —$C(O)OR^7$, —$C(O)R^7$, —$C(O)N(R^{11}R^{12})$, —$N(R^{11}R^{12})$, —$N(R^9)_2$, —$NHN(R^9)_2$, —$SR^7$, —$(CH_2)_nOR^7$, —$(CH_2)_nR^7$, -$LR^8$, -$LR^{10}$, —$OLR^8$, —$OLR^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ are each optionally substituted with 1 to 3 substituents independently selected from halogen, —CN, —$NO_2$, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$S(O)_2R^8$, —$S(O)R^8$, —$S(O)_2N(R^9)_2$, and —$NR^9S(O)_2R^8$;

each L is independently selected from a bond, —$(O(CH_2)_m)_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —$N(R^9)_2$, —$P(O)(OR^8)_2$, —$OP(O)(OR^8)_2$, —$P(O)(OR^{10})_2$, and —$OP(O)(OR^{10})_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups;

each $R^8$ is independently selected from H, —$CH(R^{10})_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)N(R^9)_2$, —$C(O)OR^{11}$, —$NR^9C(O)R^{11}$, —$NR^9R^{10}$, —$NR^{11}R^{12}$, —$N(R^9)_2$, —$OR^9$, —$OR^{10}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^9$ is independently selected from H, —$C(O)R^8$, —$C(O)OR^8$, —$C(O)R^{10}$, —$C(O)OR^{10}$, —$S(O)_2R^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —$C(O)R^{11}$, $OC(O)R^{11}$, —$C(O)OR^{11}$, —$NR^{11}R^{12}$, —$C(O)NR^{11}R^{12}$, —$C(O)NR^{11}OH$, —$S(O)_2R^{11}$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —$N(R^9)_2$, —$NR^9C(O)R^8$, —$NR^9CO_2R^8$, —$CO_2R^8$, —$C(O)R^8$ and —$C(O)N(R^9)_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, —$C(O)R^8$, $^-OC(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LSR^{10}$, -$LC(O)R^8$, —$OLC(O)R^8$, -$LC(O)OR^8$, -$LC(O)R^{10}$, -$LOC(O)OR^8$, -$LC(O)NR^9R^{11}$, -$LC(O)NR^9R^8$, -$LN(R^9)_2$, -$LNR^9R^8$, -$LNR^9R^{10}$, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, $LS(O)_2N(R^9)_2$, —$OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{10})_2$ and —$OLP(O)(OR^{10})_2$;

each $R^A$ is independently selected from —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)_nCO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, —$C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —CH=$CHCO_2R^8$, —C(=NH)—$N(R^9)_2$, and —$(CH_2)_nNHC(O)R^8$;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8; or (c) a pharmaceutically acceptable salt of any of (a) or (b). Other benzonaphthyridine compounds, and methods of making benzonaphthyridine compounds, are described in WO 2009/111337 and International Patent Application No. PCT/US2010//047587. A benzonaphthyridine compound, or a salt thereof, can be used on its own, or in combination with one or more further compounds. For example, a benzonaphthyridine compound can be used in combination with an oil-in-water emulsion or a mineral-containing composition. In a particular embodiment, a benzonaphthyridine compound is used in combination with an oil-in-water emulsion (e.g. a squalene-water emulsion, such as MF59) or a mineral-containing composition (e.g., a mineral salt such as an aluminum salt or a calcium salt).

A thiosemicarbazone compound, such as those disclosed in WO2004/060308. Methods of formulating, manufacturing, and screening for active compounds are also described in WO2004/060308. The thiosemicarbazones are particularly effective in the stimulation of human peripheral blood mononuclear cells for the production of cytokines, such as TNF-α.

A tryptanthrin compound, such as those disclosed in WO2004/064759. Methods of formulating, manufacturing, and screening for active compounds are also described in WO2004/064759. The thiosemicarbazones are particularly effective in the stimulation of human peripheral blood mononuclear cells for the production of cytokines, such as TNF-α.

A nucleoside analog, such as: (a) Isatorabine (ANA-245; 7-thia-8-oxoguanosine):

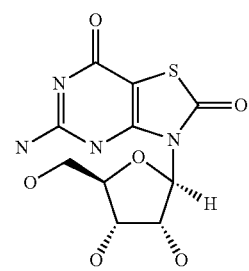 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in U.S. Pat. No. 6,924,271; US2005/0070556 and U.S. Pat. No. 5,658,731; (f) a compound having the formula:

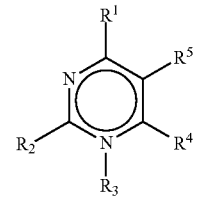

wherein:
$R_1$ and $R_2$ are each independently H, halo, —$NR_aR_b$, —OH, $C_{1-6}$ alkoxy, substituted $C_{1-6}$ alkoxy, heterocyclyl, substituted heterocyclyl, $C_{6-10}$ aryl, substituted $C_{6-10}$ aryl, $C_{1-6}$ alkyl, or substituted $C_{1-6}$ alkyl;

$R_3$ is absent, H, $C_{1-6}$ alkyl, substituted $C_{1-6}$ alkyl, $C_{6-10}$ aryl, substituted $C_{6-10}$ aryl, heterocyclyl, or substituted heterocyclyl;

$R_4$ and $R_5$ are each independently H, halo, heterocyclyl, substituted heterocyclyl, —C(O)—$R_d$, $C_{1-6}$ alkyl, substituted $C_{1-6}$ alkyl, or bound together to form a 5 membered ring as in $R_{4-5}$:

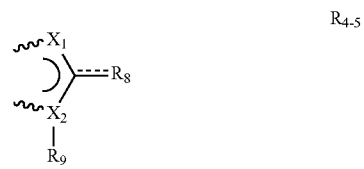

the binding being achieved at the bonds indicated by a ∿∿∿
$X_1$ and $X_2$ are each independently N, C, O, or S;
$R_8$ is H, halo, —OH, $C_{1-6}$ alkyl, $C_{2-6}$ alkenyl, $C_{2-6}$ alkynyl, —OH, —$NR_aR_b$, —$(CH_2)_n$—O—$R_c$, —O—$(C_{1-6}$ alkyl), —$S(O)_pR_e$, or —C(O)—$R_d$;

R$_9$ is H, C$_{1-6}$ alkyl, substituted C$_{1-6}$ alkyl, heterocyclyl, substituted heterocyclyl or R$_{9a}$, wherein R$_{9a}$ is:

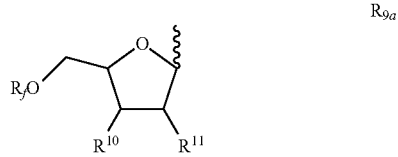

the binding being achieved at the bond indicated by a ⌇

R$_{10}$ and R$_{11}$ are each independently H, halo, C$_{1-6}$ alkoxy, substituted C$_{1-6}$ alkoxy, —NR$_a$R$_b$, or —OH;

each R$_a$ and R$_b$ is independently H, C$_{1-6}$ alkyl, substituted C$_{1-6}$ alkyl, —C(O)R$_d$, C$_{6-10}$ aryl;

each R$_c$ is independently H, phosphate, diphosphate, triphosphate, C$_{1-6}$ alkyl, or substituted C$_{1-6}$ alkyl;

each R$_d$ is independently H, halo, C$_{1-6}$ alkyl, substituted C$_{1-6}$ alkyl, C$_{1-6}$ alkoxy, substituted C$_{1-6}$ alkoxy, —NH$_2$, —NH(C$_{1-6}$ alkyl), —NH(substituted C$_{1-6}$ alkyl), —N(C$_{1-6}$ alkyl)$_2$, —N(substituted C$_{1-6}$ alkyl)$_2$, C$_{6-10}$ aryl, or heterocyclyl;

each R$_e$ is independently H, C$_{1-6}$ alkyl, substituted C$_{1-6}$ alkyl, C$_{6-10}$ aryl, substituted C$_{6-10}$ aryl, heterocyclyl, or substituted heterocyclyl;

each R$_f$ is independently H, C$_{1-6}$ alkyl, substituted C$_{1-6}$ alkyl, —C(O)R$_d$, phosphate, diphosphate, or triphosphate;

each n is independently 0, 1, 2, or 3;

each p is independently 0, 1, or 2; or or (g) a pharmaceutically acceptable salt of any of (a) to (f), a tautomer of any of (a) to (f), or a pharmaceutically acceptable salt of the tautomer.

Loxoribine (7-allyl-8-oxoguanosine) (U.S. Pat. No. 5,011,828).

Compounds disclosed in WO2004/87 153, including: Acylpiperazine compounds, Indoledione compounds, Tetrahydraisoquinoline (THIO) compounds, Benzocyclodione compounds, Aminoazavinyl compounds, Aminobenzimidazole quinolinone (ABIQ) compounds (U.S. Pat. No. 6,605,617, WO02/18383), Hydrapthalamide compounds, Benzophenone compounds, Isoxazole compounds, Sterol compounds, Quinazilinone compounds, Pyrrole compounds (WO2004/018455), Anthraquinone compounds, Quinoxaline compounds, Triazine compounds, Pyrazalopyrimidine compounds, and Benzazole compounds (WO03/082272).

Compounds disclosed in WO2006/002422.

An aminoalkyl glucosaminide phosphate derivative, such as RC-529 (Johnson et al. (1999) *Bioorg Med Chem Lett* 9:2273-2278, Evans et al. (2003) *Expert Rev Vaccines* 2:219-229).

A phosphazene, such as poly[di(carboxylatophenoxy) phosphazene] ("PCPP") as described, for example, in Andrianov et al. (1998) *Biomaterials* 19:109-115 and Payne et al. (1998) *Adv Drug Delivery Review* 31:185-196.

Small molecule immunopotentiators (SMIPs) such as:
N2-methyl-1-(2-methylpropyl)-1H-imidazo[4,5-c]quinoline-2,4-diamine N2,N2-dimethyl-1-(2-methylpropyl)-1H-imidazo[4,5-c]quinoline-2,4-diamine N2-ethyl-N2-methyl-1-(2-methylpropyl)-1H-imidazo[4,5-c]quinoline-2,4-diamine N2-methyl-1-(2-methylpropyl)-N2-propyl-1H-imidazo[4,5-c]quinoline-2,4-diamine
1-(2-methylpropyl)-N2-propyl-1H-imidazo[4,5-c]quinoline-2,4-diamine N2-butyl-1-(2-methylpropyl)-1H-imidazo[4,5-c]quinoline-2,4-diamine N2-butyl-N2-methyl-1-(2-methylpropyl)-1H-imidazo[4,5-c]quinoline-2,4-diamine N2-methyl-1-(2-methylpropyl)-N2-pentyl-1H-imidazo[4,5-c]quinoline-2,4-diamine
N2-methyl-1-(2-methylpropyl)-N2-prop-2-enyl-1H-imidazo[4,5-c]quinoline-2,4-diamine
1-(2-methylpropyl)-2-[(phenylmethyl)thio]-1H-imidazo[4,5-c]quinolin-4-amine 1-(2-methylpropyl)-2-(propylthio)-1H-imidazo[4,5-c]quinolin-4-amine 2-[[4-amino-1-(2-methylpropyl)-1H-imidazo[4,5-c]quinolin-2-yl](methyl)amino]ethanol
2-[[4-amino-1-(2-methylpropyl)-1H-imidazo[4,5-c]quinolin-2-yl](methyl)amino]ethyl acetate
4-amino-1-(2-methylpropyl)-1,3-dihydro-2H-imidazo[4,5-c]quinolin-2-one N2-butyl-1-(2-methylpropyl)-N4,N4-bis(phenylmethyl)-1H-imidazo[4,5-c]quinoline-2,4-diamine
N2-butyl-N2-methyl-1-(2-methylpropyl)-N4,N4-bis(phenylmethyl)-1H-imidazo[4,5-c]quinoline-2,4-diamine
N2-methyl-1-(2-methylpropyl)-N4,N4-bis(phenylmethyl)-1H-imidazo[4,5-c]quinoline-2,4-diamine
N2,N2-dimethyl-1-(2-methylpropyl)-N4,N4-bis(phenylmethyl)-1H-imidazo[4,5-c]quinoline-2,4-diamine
1-[4-amino-2-[methyl(propyl)amino]-1H-imidazo[4,5-c]quinolin-1-yl]-2-methylpropan-2-ol
1-[4-amino-2-(propylamino)-1H-imidazo[4,5-c]quinolin-1-yl]-2-methylpropan-2-ol
N4,N4-dibenzyl-1-(2-methoxy-2-methylpropyl)-N2-propyl-1H-imidazo[4,5-c]quinoline-2,4-diamine.

The cytokine-inducing agents for use in the present invention may be modulators and/or agonists of Toll-Like Receptors (TLR). For example, they may be agonists of one or more of the human TLR1, TLR2, TLR3, TLR4, TLR7, TLR8, and/or TLR9 proteins. Preferred agents are agonists of TLR4 (e.g., modified natural lipid As derived from enterobacterial lipopolysaccharides, phospholipid compounds, such as the synthetic phospholipid dimer, E6020), TLR7 (e.g., benzonaphthyridines, imidazoquinolines) and/or TLR9 (e.g., CpG oligonucleotides). These agents are useful for activating innate immunity pathways.

The cytokine-inducing agent can be added to the composition at various stages during its production. For example, it may be within an antigen composition, and this mixture can then be added to an oil-in-water emulsion. As an alternative, it may be within an oil-in-water emulsion, in which case the agent can either be added to the emulsion components before emulsification, or it can be added to the emulsion after emulsification. Similarly, the agent may be coacervated within the emulsion droplets. The location and distribution of the cytokine-inducing agent within the final composition will depend on its hydrophilic/lipophilic properties, e.g., the agent can be located in the aqueous phase, in the oil phase, and/or at the oil-water interface.

The cytokine-inducing agent can be conjugated to a separate agent, such as an antigen (e.g., CRM197). A general review of conjugation techniques for small molecules is provided in Thompson et al. (2003) *Methods in Molecular Medicine* 94:255-266. As an alternative, the adjuvants may be non-covalently associated with additional agents, such as by way of hydrophobic or ionic interactions.

Preferred cytokine-inducing agents are (a) benzonapthridine compounds; (b) immunostimulatory oligonucleotides and (c) 3dMPL.

Immunostimulatory oligonucleotides can include nucleotide modifications/analogs such as phosphorothioate modifications and can be double-stranded or (except for RNA) single-stranded. Kandimalla et al. (2003) *Nucleic Acids Research* 31:2393-2400, WO02/26757, and WO99/62923 disclose possible analog substitutions, e.g., replacement of guanosine with 2'-deoxy-7-deazaguanosine. The adjuvant effect of CpG oligonucleotides is further discussed in Krieg (2003) *Nature Medicine* 9:831-835; McCluskie et al. (2002) *FEMS Immunology and Medical Microbiology* 32:179-185; WO98/40100; U.S. Pat. Nos. 6,207,646; 6,239,116 and 6,429,199. A CpG sequence may be directed to TLR9, such as the motif GTCGTT or TTCGTT (Kandimalla et al. (2003) *Biochemical Society Transactions* 31 (part 3): 654-658). The CpG sequence may be specific for inducing a Th1 immune response, such as a CpG-A ODN (oligodeoxynucleotide), or it may be more specific for inducing a B cell response, such a CpG-B ODN. CpG-A and CpG-B ODNs are discussed in Blackwell et al. (2003) *J Immunol* 170:4061-4068, Krieg (2002) *Trends Immunol* 23:64-65; and WO01/95935. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers". See, for example, references Kandimalla et al. (2003) *Biochemical Society Transactions* 31 (part 3): 654-658; Kandimalla et al. (2003) *BBRC* 306:948-953; Bhagat et al. (2003) *BBRC* 300:853-861 and WO03/035836. A useful CpG adjuvant is CpG7909, also known as PROMUNE™ (Coley Pharmaceutical Group, Inc.).

As an alternative, or in addition, to using CpG sequences, TpG sequences can be used (WO01/22972). These oligonucleotides may be free from unmethylated CpG motifs.

The immunostimulatory oligonucleotide may be pyrimidine-rich. For example, it may comprise more than one consecutive thymidine nucleotide (e.g., TTTT (SEQ ID NO:17), as disclosed in WO01/22972), and/or it may have a nucleotide composition with >25% thymidine (e.g., >35%, >40%, >50%, >60%, >80%, etc.). For example, it may comprise more than one consecutive cytosine nucleotide (e.g., CCCC (SEQ ID NO:18), as disclosed in WO01/22972), and/or it may have a nucleotide composition with >25% cytosine (e.g., >35%, >40%, >50%, >60%, >80%, etc.). These oligonucleotides may be free from unmethylated CpG motifs.

Immunostimulatory oligonucleotides will typically comprise at least 20 nucleotides. They may comprise fewer than 100 nucleotides.

3dMPL (also known as 3 de-O-acylated monophosphoryl lipid A or 3-O-desacyl-4'-monophosphoryl lipid A) is an adjuvant in which position 3 of the reducing end glucosamine in monophosphoryl lipid A has been de-acylated. 3dMPL has been prepared from a heptoseless mutant of *Salmonella minnesota*, and is chemically similar to lipid A but lacks an acid-labile phosphoryl group and a base-labile acyl group. It activates cells of the monocyte/macrophage lineage and stimulates release of several cytokines, including IL-1, IL-12, TNF-α and GM-CSF (see also Thompson et al. (2005) *J Leukoc Biol* 78: 'The low-toxicity versions of LPS, MPL® adjuvant and RC529, are efficient adjuvants for CD4+ T cells'). Preparation of 3dMPL was originally described in UK patent application GB-A-22202 11.

3dMPL can take the form of a mixture of related molecules, varying by their acylation (e.g., having 3, 4, 5 or 6 acyl chains, which may be of different lengths). The two glucosamine (also known as 2-deoxy-2-amino-glucose) monosaccharides are N-acylated at their 2-position carbons (i.e., at positions 2 and 2'), and there is also O-acylation at the 3' position. The group attached to carbon 2 has formula —NH—CO—CH$_2$—CR$^1$R$^{1'}$. The group attached to carbon 2' has formula —NH—CO—CH$_2$—CR$^2$R$^{2'}$. The group attached to carbon 3' has formula —O—CO—CH$_2$—CR$^3$R$^{3'}$. A representative structure is:

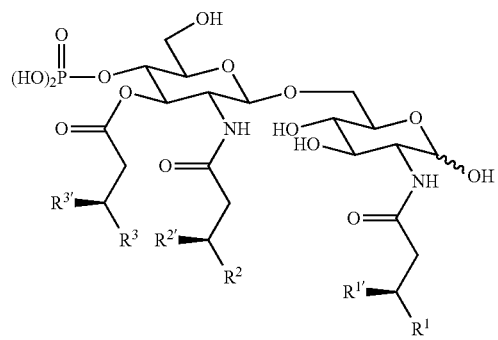

Groups R$^1$, R$^2$ and R$^3$ are each independently —(CH$_2$)$_n$—CH$_3$. The value of n is preferably between 8 and 16, more preferably between 9 and 12, and is most preferably 10.

Groups R$^{1'}$, R$^{2'}$ and R$^{3'}$ can each independently be: (a) —H; (b) —OH; or (c) —O—CO—R$^4$, where R$^4$ is either —H or —(CH$_2$)$_m$—CH$_3$, wherein the value of m is preferably between 8 and 16, and is more preferably 10, 12 or 14. At the 2 position, m is preferably 14. At the 2' position, m is preferably 10. At the 3' position, m is preferably 12. Groups R$^{1'}$, R$^{2'}$ and R$^{3'}$ are thus preferably —O-acyl groups from dodecanoic acid, tetradecanoic acid or hexadecanoic acid.

When all of R$^{1'}$, R$^{2'}$ and R$^{3'}$ are —H then the 3dMPL has only 3 acyl chains (one on each of positions 2, 2' and 3').

When only two of $R^{1'}$, $R^{2'}$ and $R^{3'}$ are —H then the 3dMPL can have 4 acyl chains. When only one of $R^{1'}$, $R^{2'}$ and $R^{3'}$ is —H then the 3dMPL can have 5 acyl chains. When none of $R^{1'}$, $R^{2'}$ and $R^{3'}$ is —H then the 3dMPL can have 6 acyl chains. The 3dMPL adjuvant used according to the invention can be a mixture of these forms, with from 3 to 6 acyl chains, but it is preferred to include 3dMPL with 6 acyl chains in the mixture, and in particular to ensure that the hexaacyl chain form makes up at least 10% by weight of the total 3dMPL e.g., >20%, >30%, >40%, >50% or more. 3dMPL with 6 acyl chains has been found to be the most adjuvant-active form.

Thus the most preferred form of 3dMPL for inclusion in compositions of the invention has formula (IV), shown below.

Where 3dMPL is used in the form of a mixture then references to amounts or concentrations of 3dMPL in compositions of the invention refer to the combined 3dMPL species in the mixture.

In aqueous conditions, 3dMPL can form micellar aggregates or particles with different sizes e.g., with a diameter <150 nm or >500 nm. Either or both of these can be used with the invention, and the better particles can be selected by routine assay. Smaller particles (e.g., small enough to give a clear aqueous suspension of 3dMPL) are preferred for use according to the invention because of their superior activity (WO94/21292). Preferred particles have a mean diameter less than 220 nm, more preferably less than 200 nm or less than 150 nm or less than 120 nm, and can even have a mean diameter less than 100 nm. In most cases, however, the mean diameter will not be lower than 50 nm. These particles are small enough to be suitable for filter sterilization. Particle diameter can be assessed by the routine technique of dynamic light scattering, which reveals a mean particle diameter. Where a particle is said to have a diameter of x nm, there will generally be a distribution of particles about this mean, but at least 50% by number (e.g., >60%, >70%, >80%, >90%, or more) of the particles will have a diameter within the range x+25%.

3dMPL can advantageously be used in combination with an oil-in-water emulsion. Substantially all of the 3dMPL may be located in the aqueous phase of the emulsion. The 3dMPL can be used on its own, or in combination with one or more further compounds. For example, it is known to use 3dMPL in combination with the QS21 saponin (WO94/00153) (including in an oil-in-water emulsion (WO95/17210)), with an immunostimulatory oligonucleotide, with both QS21 and an immunostimulatory oligonucleotide, with aluminum phosphate (WO96/26741), with aluminum hydroxide (WO93/19780), or with both aluminum phosphate and aluminum hydroxide.

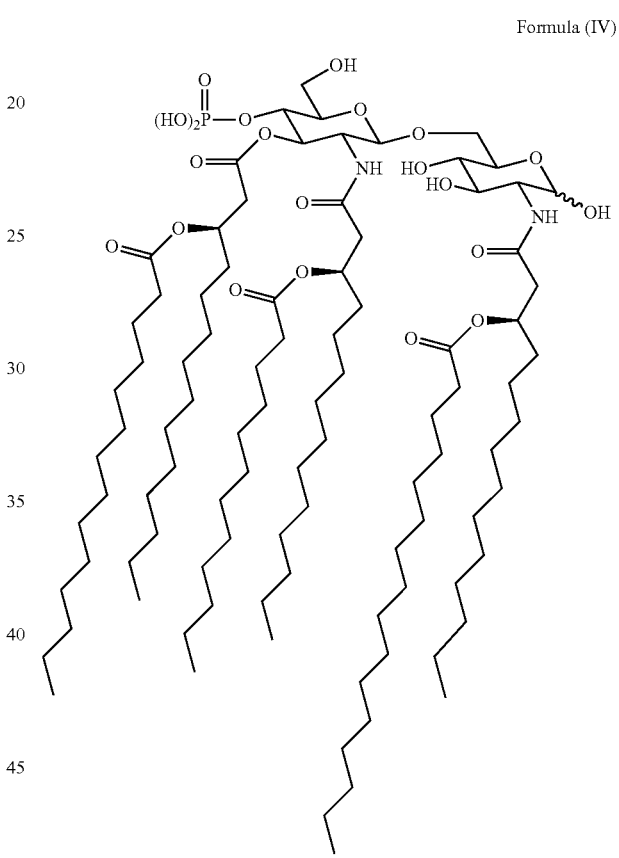

Formula (IV)

Fatty Adjuvants

Fatty adjuvants that can be used with the invention include the oil-in-water emulsions described above, and also include, for example:

A phospholipid compound of formula I, II or III, or a salt thereof:
as defined in WO03/011223, such as 'ER 803058', 'ER 803732', 'ER 804053', ER 804058', 'ER 804059', 'ER 804442', 'ER 804680', 'ER 804764', ER 803022 or 'ER 804057'

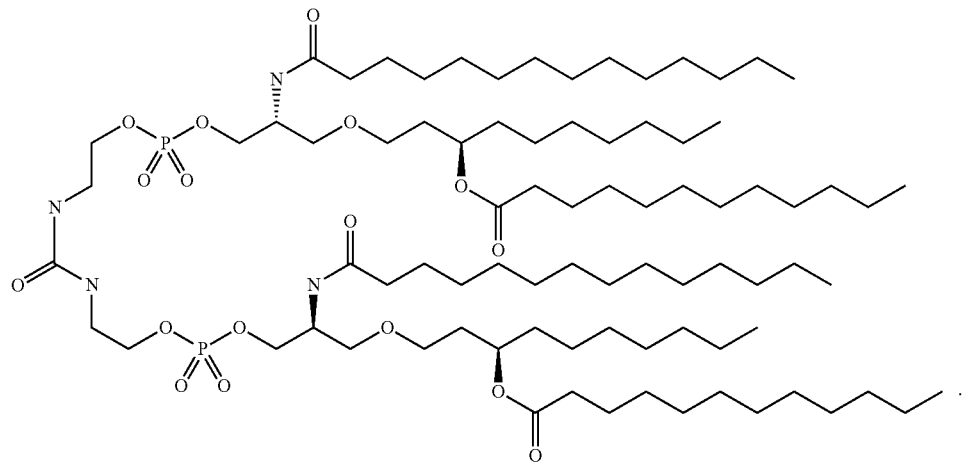

ER804057 is also called E6020. A phospholipid compound of formula I, II or III, or a salt thereof, can be used on its own, or in combination with one or more further compounds. For example, a compound of formula I, II or III, can be used in combination with an oil-in-water emulsion or a mineral-containing composition. In a particular embodiment, E6020 is used in combination with an oil-in-water emulsion (e.g. a squalene-water emulsion, such as MF59) or a mineral-containing composition (e.g., a mineral sald such as an aluminum salt or a calcium salt).

- Derivatives of lipid A from *Escherichia coli* such as OM-174 (described in Meraldi et al. (2003) *Vaccine* 21:2485-249 1 & Pajak et al. (2003) *Vaccine* 21:836-842).
- A formulation of a cationic lipid and a (usually neutral) co-lipid, such as aminopropyl-dimethyl-myristoleyloxy-propanaminium bromide-diphytanoylphosphatidyl-ethanolamine ("VAXFECTIN™") or aminopropyl-dimethyl-bis-dodecyloxy-propanaminium bromide-dioleoylphosphatidyl-ethanolamine ("GAP-DLRIE: DOPE"). Formulations containing (+)—N-(3-aminopropyl)-N,N-dimethyl-2,3-bis(syn-9-tetradeceneyloxy)-1-propanaminium salts are preferred (U.S. Pat. No. 6,586,409).
- 3-O-deacylated monophosphoryl lipid A (see above).
- Compounds containing lipids linked to a phosphate-containing acyclic backbone, such as the TLR4 antagonist E5564 (Wong et al. (2003) *J Clin Pharmacol* 43(7): 735-42, US2005/0215517):
- Lipopeptides (i.e., compounds comprising one or more fatty acid residues and two or more amino acid residues), such as lipopeptides based on glycerylcysteine. Specific examples of such peptides include compounds of the following formula

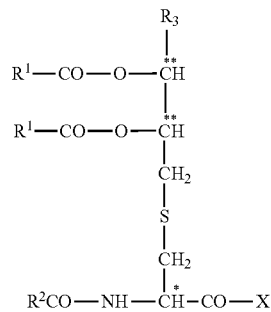

\* = R
\*\* = R or S in which each of $R^1$ and $R^2$ represents a saturated or unsaturated, aliphatic or mixed aliphatic-cycloaliphatic hydrocarbon radical having from 8 to 30, preferably 11 to 21, carbon atoms that is optionally also substituted by oxygen functions, $R^3$ represents hydrogen or the radical $R_1$—CO—O—$CH_2$— in which $R^1$ has the same meaning as above, and X represents an amino acid bonded by a peptide linkage and having a free, esterified or amidated carboxy group, or an amino acid sequence of from 2 to 10 amino acids of which the terminal carboxy group is in free, esterified or amidated form. In certain embodiments, the amino acid sequence comprises a D-amino acid, for example, D-glutamic acid (D-Glu) or D-gamma-carboxy-glutamic acid (D-Gla).

Bacterial lipopeptides generally recognize TLR2, without requiring TLR6 to participate. (TLRs operate cooperatively to provide specific recognition of various triggers, and TLR2 plus TLR6 together recognize peptidoglycans, while TLR2 recognizes lipopeptides without TLR6.) These are sometimes classified as natural lipopeptides and synthetic lipopeptides. Synthetic lipopeptides tend to behave similarly, and are primarily recognized by TLR2.

Lipopeptides suitable for use as adjuvants include compounds have the formula:

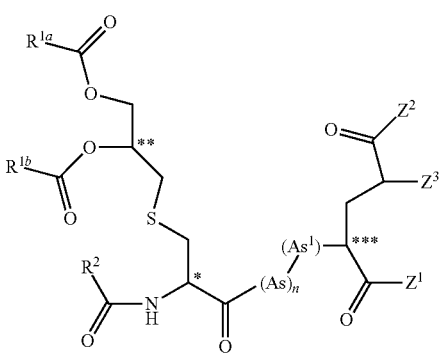

where the chiral center labeled * and the one labeled *** are both in the R configuration;

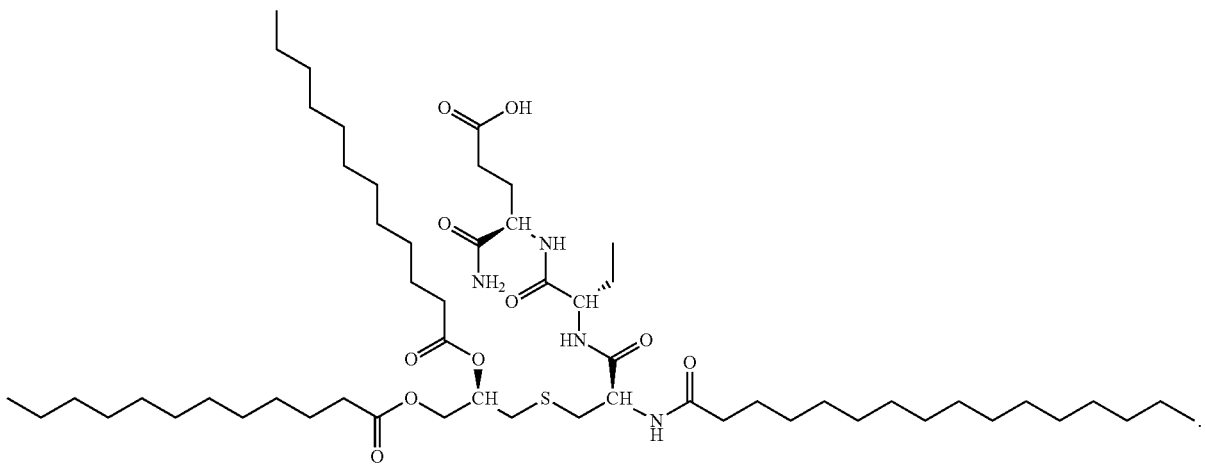 [SMILES: CCCCCCCCCCCCCCCC(=O)N[C@@H](CSC[C@@H](COC(=O)CCCCCCCCCCC)OC(=O)CCCCCCCCCCC)C(=O)N[C@@H](CC)C(=O)N[C@H](CCC(=O)O)C(N)=O]

the chiral center labeled ** is either in the R or S configuration;

each $R^{1a}$ and $R^{1b}$ is independently an aliphatic or cycloaliphatic-aliphatic hydrocarbon group having 7-21 carbon atoms, optionally substituted by oxygen functions, or one of $R^{1a}$ and $R^{1b}$, but not both, is H;

$R^2$ is an aliphatic or cycloaliphatic hydrocarbon group having 1-21 carbon atoms and optionally substituted by oxygen functions;

n is 0 or 1;

As represents either —O-Kw-CO— or —NH-Kw-CO—, where Kw is an aliphatic hydrocarbon group having 1-12 carbon atoms;

$As^1$ is a D- or L-alpha-amino acid;

$Z^1$ and $Z^2$ each independently represent —OH or the N-terminal radical of a D- or L-alpha amino acid of an amino-(lower alkane)-sulfonic acid or of a peptide having up to 6 amino acids selected from the D- and L-alpha aminocarboxylic acids and amino-lower alkyl-sulfonic acids; and $Z^3$ is H or —CO—$Z^4$, where $Z^4$ is —OH or the N-terminal radical of a D- or L-alpha amino acid of an amino-(lower alkane)-sulfonic acid or of a peptide having up to 6 amino acids selected from the D and L-alpha aminocarboxylic acids and amino-lower alkyl-sulfonic acids; or an ester or amide formed from the carboxylic acid of such compounds. Suitable amides include —$NH_2$ and NH(lower alkyl), and suitable esters include C1-C4 alkyl esters. (lower alkyl or lower alkane, as used herein, refers to $C_1$-$C_6$ straight chain or branched alkyls).

Such compounds are described in more detail in U.S. Pat. No. 4,666,886. In one particular embodiment, the lipopeptide has the formula:

Another example of a lipopeptide species is called LP40, and is an agonist of TLR2. Akdis, et al., *Eur. J. Immunology*, 33: 2717-26 (2003).

These are related to a known class of lipopeptides from *E. coli*, referred to as murein lipoproteins. Certain partial degradation products of those proteins called murein lipopetides are described in Hantke, et al., *Eur. J. Biochem.*, 34: 284-296 (1973). These comprise a peptide linked to N-acetyl muramic acid and are thus related to Muramyl peptides, which are described in Baschang, et al., Tetrahedron, 45(20): 6331-6360 (1989).

Aluminum Salt Adjuvants

The adjuvants known as "aluminum hydroxide" and "aluminum phosphate" may be used. These names are conventional, but are used for convenience only, as neither is a precise description of the actual chemical compound which is present (e.g., see chapter 9 of *Vaccine Design: The Subunit and Adjuvant Approach* (eds. Powell & Newman) Plenum Press 1995 (ISBN 0-306-44867-X)). The invention can use any of the "hydroxide" or "phosphate" adjuvants that are in general use as adjuvants.

The adjuvants known as "aluminum hydroxide" are typically aluminum oxyhydroxide salts, which are usually at least partially crystalline. Aluminum oxyhydroxide, which can be represented by the formula AlO(OH), can be distinguished from other aluminum compounds, such as aluminum hydroxide Al(OH)$_3$, by infrared (IR) spectroscopy, in particular by the presence of an adsorption band at 1070 cm$^{-1}$ and a strong shoulder at 3090-3100 cm$^{-1}$ (chapter 9 of *Vaccine Design: The Subunit and Adjuvant Approach* (eds. Powell & Newman) Plenum Press 1995 (ISBN 0-306-44867-X)). The degree of crystallinity of an aluminum hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g., as seen in transmission electron micrographs) is typical for aluminum hydroxide adjuvants. The pI of aluminum hydroxide adjuvants is typically about 11, i.e., the adjuvant itself has a positive surface charge at physiological pH. Adsorptive capacities of between 1.8-2.6 mg protein per mg Al$^{+++}$ at pH 7.4 have been reported for aluminum hydroxide adjuvants.

The adjuvants known as "aluminum phosphate" are typically aluminum hydroxyphosphates, often also containing a small amount of sulfate (i.e., aluminum hydroxyphosphate sulfate). They may be obtained by precipitation, and the reaction conditions and concentrations during precipitation influence the degree of substitution of phosphate for hydroxyl in the salt. Hydroxyphosphates generally have a PO$_4$/Al molar ratio between 0.3 and 1.2. Hydroxyphosphates can be distinguished from strict AlPO$_4$ by the presence of hydroxyl groups. For example, an IR spectrum band at 3164 cm$^{-1}$ (e.g., when heated to 200° C.) indicates the presence of structural hydroxyls (ch. 9 of *Vaccine Design: The Subunit and Adjuvant Approach* (eds. Powell & Newman) Plenum Press 1995 (ISBN 0-306-44867-X)).

The PO$_4$/Al$^{3+}$ molar ratio of an aluminum phosphate adjuvant will generally be between 0.3 and 1.2, preferably between 0.8 and 1.2, and more preferably 0.95+0.1. The aluminum phosphate will generally be amorphous, particularly for hydroxyphosphate salts. A typical adjuvant is amorphous aluminum hydroxyphosphate with PO$_4$/Al molar ratio between 0.84 and 0.92, included at 0.6 mg Al$^{3+}$/ml. The aluminum phosphate will generally be particulate (e.g., plate-like morphology as seen in transmission electron micrographs). Typical diameters of the particles are in the range 0.5-20 μm (e.g., about 5-10 μm) after any antigen adsorption. Adsorptive capacities of between 0.7-1.5 mg protein per mg Al-$^{+++}$ at pH 7.4 have been reported for aluminum phosphate adjuvants.

The point of zero charge (PZC) of aluminum phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminum phosphates used according to the invention will generally have a PZC of between 4.0 and 7.0, more preferably between 5.0 and 6.5, e.g., about 5.7.

Suspensions of aluminum salts used to prepare compositions of the invention may contain a buffer (e.g., a phosphate or a histidine or a Tris buffer), but this is not always necessary. The suspensions are preferably sterile and pyrogen-free. A suspension may include free aqueous phosphate ions e.g., present at a concentration between 1.0 and 20 mM, preferably between 5 and 15 mM, and more preferably about 10 mM. The suspensions may also comprise sodium chloride.

The invention can use a mixture of both an aluminum hydroxide and an aluminum phosphate. In this case there may be more aluminum phosphate than hydroxide e.g., a weight ratio of at least 2:1 e.g., >5:1, >6:1, >7:1, >8:1, >9:1, etc.

The concentration of Al$^{+++}$ in a composition for administration to a patient is preferably less than 10 mg/ml e.g., <5 mg/ml, <4 mg/ml, <3 mg/ml, <2 mg/ml, <1 mg/ml, etc. A preferred range is between 0.3 and 1 mg/ml. A maximum of 0.85 mg/dose is preferred.

As well as including one or more aluminum salt adjuvants, the adjuvant component may include one or more further adjuvant or immunostimulating agents. Such additional components include, but are not limited to: a benzonaphthyridine compound, a 3-O-deacylated monophosphoryl lipid A adjuvant (3d-MPL'); and/or an oil-in-water emulsion. 3d-MPL has also been referred to as 3 de-O-acylated monophosphoryl lipid A or as 3-O-desacyl-4'-monophosphoryl lipid A. The name indicates that position 3 of the reducing end glucosamine in monophosphoryl lipid A is de-acylated. It has been prepared from a heptoseless mutant of S.minnesota, and is chemically similar to lipid A but lacks an acid-labile phosphoryl group and a base-labile acyl group. It activates cells of the monocyte/macrophage lineage and stimulates release of several cytokines, including IL-1, IL-12, TNF-α and GM-CSF. Preparation of 3d-MPL was originally described in UK patent application GB-A-22202 11, and the product has been manufactured and sold by Corixa Corporation under the name MPL™. Further details can be found in Myers et al. (1990) pages 145-156 of *Cellular and molecular aspects of endotoxin reactions*; Ulrich (2000) Chapter 16 (pages 273-282) of *Vaccine Adjuvants: Preparation Methods and Research Protocols* (Volume 42 of *Methods in Molecular Medicine* series). ISBN: 1-59259-083-7. Ed. O'Hagan; Johnson et al. (1999) *J Med Chem* 42:4640-9; and Baldrick et al. (2002) *Regulatory Toxicol Pharmacol* 35:398-413.

The use of an aluminum hydroxide and/or aluminum phosphate adjuvant is useful, particularly in children, and antigens are generally adsorbed to these salts. Squalene-in-water emulsions are also preferred, particularly in the elderly. Useful adjuvant combinations include combinations of Th1 and Th2 adjuvants such as CpG and alum, or resiquimod and alum. A combination of aluminum phosphate and 3dMPL may be used. Other combinations that may be used include: alum and a benzonapthridine compound or a SMIP, a squalene-in-water emulsion (such as MF59) and a benzonapthridine compound or a SMIP, and E6020 and a squalene-in-water emulsion, such as MF59) or alum.

The compositions of the invention may elicit both a cell mediated immune response as well as a humoral immune response.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class 1 molecules.

CD4 T cells can express a CD4 co-receptor and are commonly referred to as T helper cells. CD4 T cells are able to recognize antigenic peptides bound to MHC class I1 molecules. Upon interaction with a MHC class I1 molecule, the CD4 cells can secrete factors such as cytokines These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH 1 cells may secrete one or more of IL-2, IFN-γ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

A TH1 immune response may include one or more of an increase in CTLs, an increase in one or more of the cytokines associated with a TH1 immune response (such as IL-2, IFN-γ, and TNF-β), an increase in activated macrophages, an increase in NK activity, or an increase in the production of IgG2a. Preferably, the enhanced TH1 immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

The enhanced immune response may be one or both of a systemic and a mucosal immune response. Preferably, the immune response provides for one or both of an enhanced systemic and an enhanced mucosal immune response.

Methods of Treatment, Use and Administration

Compositions of the invention are suitable for administration to pregnant females and infants, and the invention provides a method of inducing an immune response in a pregnant female and/or infant, comprising the step of administering a composition (e.g., an anti-RSV immune response inducing composition) of the invention to the pregnant female and/or infant. The compositions (e.g., an anti-RSV immune response inducing composition) can be used to produce a vaccine formulation for immunizing a pregnant female and/or an infant. For example, the immune response may be raised following administration of a purified RSV F protein, an alphavirus replicon particle, or self-replicating RNA.

The invention also provides a composition of the invention for use as a medicament, e.g., for use in immunizing a patient against RSV infection.

In one embodiment, the invention provides an anti-RSV immune response inducing composition for use in providing protective immunity against RSV in an infant by a method comprising (a) administering a first anti-RSV immune response inducing composition to a female during pregnancy; and (b) administering a second anti-RSV immune response inducing composition to the infant that is born from the pregnancy.

In another embodiment, the invention provides an anti-RSV immune response inducing composition for use in raising an immune response in a pregnant female by a method comprising (a) administering a first anti-RSV immune response inducing composition to the female; and (b) administering a second anti-RSV immune response inducing composition to the infant that is born from the pregnancy.

In a further embodiment, the invention provides an anti-RSV immune response inducing composition for use in providing protective immunity against RSV in an infant, wherein the infant was born to a female to whom an anti-RSV immune response inducing composition was administered during the time when the female was pregnant with the infant.

In another embodiment, the invention provides an anti-RSV immune response inducing composition for use in providing protective immunity against RSV in an infant, wherein the infant possesses maternal antibodies against RSV.

The presence of maternal antibodies against RSV in the infant can be assessed using any suitable method. For example, because the infant's immune system is immature, anti-RSV antibodies, especially IgG antibodies, present in the infant during the first weeks and months following birth (e.g. from birth up to about 2 or 3 or 4 months) are maternal antibodies. Many methods to determine whether maternal antibodies that bind pathogen antigens are well known in the art. See, e.g., Pappaioanou M, et al., Accurate Detection of Maternal Antibodies to HIV in Newborn Whole Blood Dried on Filter Paper, AIDS 7(4):483-488 (1993), and Pinon J. M. et al., Strategy for Diagnosis of Congenital Toxoplasmosis: Evaluation of Methods Comparing Mothers and Newborns and Standard Methods for Postnatal Detection of Immunoglobin G, M, and A Antibodies, J. Clin. Microbiol. 39(6): 2267-2271 (2001).

The invention also provides the use of a polypeptide as described above in the manufacture of a medicament for raising an immune response in a patient.

The immune response raised by these methods and uses will generally include an antibody response, preferably a protective antibody response. Methods for assessing antibody responses after RSV vaccination are well known in the art.

Compositions of the invention can be administered in a number of suitable ways, such as intramuscular injection (e.g., into the arm or leg), subcutaneous injection, intranasal administration, oral administration, intradermal administration, transcutaneous administration, transdermal administration, and the like. The appropriate route of administration will be dependent upon the age, health and other characteristics of the pregnant female or infant. A clinician will be able to determine an appropriate route of administration based on these and other factors.

Treatment can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Administration of more than one dose (typically two doses) is particularly useful in immunologically naïve patients. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, and the like.).

Vaccine formulations produced using a composition of the invention may be administered to patients at substantially the same time as (e.g., during the same medical consultation or visit to a healthcare professional or vaccination centre) other vaccines.

EXAMPLES

Example 1

The effectiveness and immunogenicity of the RSV immunization regimen described herein can be assessed, for example, using suitable animal models.

In one example, female cotton rats will be administered an anti-RSV immune response inducing composition before and/or after they are mated to induce the production of anti-RSV antibodies during pregnancy. Alternatively, female cotton rats may be infected with RSV before and/or after they are mated and boosted with an anti-RSV immune response inducing composition before and/or after they are mated to increase the production of anti-RSV antibodies during pregnancy. The presence and titer of anti-RSV antibodies in the pregnant cotton rat can be assessed using any suitable method, such as the neutralizing titer assays described herein or by an ELISA. Antibodies produced by the pregnant cotton rat will cross the placenta and enter the fetal circulation. After birth, the neonatal rats will be nursed by their mother or by a naïve cotton rat (that has not been exposed to RSV or an anti-RSV immune response inducing composition). Additional anti-RSV antibodies may be transferred to the infant cotton rats by nursing on females that were immunized with an anti-RSV immune response inducing composition or infected with RSV and boosted with an anti-RSV inducing composition. Some of the newborn rats will be administered an anti-RSV immune response inducing composition one or more times (e.g., a prime followed by one or more boosts). When an anti-RSV immune response inducing composition is administered to a newborn two or more times, the compositions will be the same or different. The anti-RSV antibody levels in infant cotton rats can be assessed at various time points after birth by any suitable method, such as the neutralizing titer assays described herein or by an ELISA. The level of protection from RSV conferred by the immunization regimens can be assessed by challenging the infant cotton rats with RSV and assessing the titer of virus in the infant cotton rat lungs or nasal washes or by examining the pathology of the infant cotton rat lungs or nasal cavity. Comparing the anti-RSV antibody levels and degrees of protection against RSV at various time points in infant cotton rats who have or have not been actively immunized and who were born to mothers or nursed on females who have had different RSV antigen exposures (for example, none, RSV infection, immunization with an anti-RSV immune response inducing composition, or RSV infection followed by boosting with an anti-RSV immune response inducing composition) will allow assessment of the effectiveness and immunogenicity of the RSV immunization regimen described herein. In another example, the potential for low efficiency transplacental transfer of maternal antibody to the fetus is addressed by manually transferring antibody containing preparations obtained from an adult cotton rat. An adult cotton rat will be administered an anti-RSV immune response inducing composition to induce the production of anti-RSV antibodies or may be infected with RSV and boosted with an anti-RSV immune response inducing composition. Anti-RSV antibodies (or serum containing the antibodies) will be obtained from the cotton rat and administered to naïve cotton rats (newborn or young cotton rats), for example, by intraperitoneal injection. Some of the naïve cotton rats will be administered an anti-RSV immune response inducing composition one or more times (e.g., a prime followed by one or more boosts). When an anti-RSV immune response inducing composition is administered to the naïve rats two or more times, the compositions will be the same or different. The anti-RSV antibody levels in infant cotton rats can be assessed at various time points after birth by any suitable method, such as the neutralizing titer assays described herein or by an ELISA. The level of protection from RSV conferred by the immunization regimens can be assessed by challenging the infant cotton rats with RSV and assessing the titer of virus in the infant cotton rat lungs or nasal washes or by examining the pathology of the infant cotton rat lungs or nasal cavity. Comparing the anti-RSV antibody levels and degrees of protection against RSV at various time points in infant cotton rats who have or have not been actively immunized and who were administered antibody-containing preparations obtained from cotton rats who have had different RSV antigen exposures (for example, none, RSV infection, immunization with an anti-RSV immune response inducing composition, or RSV infection followed by boosting with an anti-RSV immune response inducing composition) will allow assessment of the effectiveness and immunogenicity of the RSV immunization regimen described herein.

RSV Neutralization Assay

HEp-2 cells will be harvested from confluent monolayers by trypsinization, resuspended cell culture medium containing 5% fetal bovine serum (FBS) at a density of $6.5 \times 10^6$ cells/ml, seeded in 96 well plates at 0.1 ml per well, and incubated at 37° C. in 5% $CO_2$ for 3-6 hours.

Test sera and control sera will be heat inactivated at 56° C. for 30 minutes and serially two-fold diluted in phosphate-buffered saline (PBS), 5% bovine serum albumin (BSA).

The serially diluted sera will be mixed with equal volumes of RSV that will have been pre-diluted in PBS 5% FBS to a concentration such that the volume added will yield 80-140 syncytia/well in the absence of test sera. The mixtures of RSV and serially diluted sera will be incubated for 2 hours at 37° C. in 5% CO2.

The medium will be aspirated from the HEp-2 seeded assay plate and the virus-sera mixtures will be added to the wells of the plates. The plate will be incubated for 2 hours at 37° C. in 5% $CO_2$. The virus-sera mixtures will be aspirated from the plate.

A solution of room temperature 0.75% methylcellulose in EMEM (phenol red free), 5% FBS, will be added to the wells. The plate will then be incubated at 37° C. in 5% $CO_2$ for 40-46 hours.

The methylcellulose will be aspirated from the wells and 10% buffered formalin is added to the wells. The plate will be incubated at room temperature for 1 hour. The plates will be washed three times with wash buffer (1×PBS, 0.05% Tween 20). Permeabilization/blocking buffer (D-PBS, 2.5% FBS, 0.5% saponin, 0.1% NaAzide) will be added to the wells, and the plate will be incubated for 1 hour at room temperature.

The permeabilization/blocking buffer will be aspirated from the wells. The wells will then be washed three times with wash buffer. A 1:1000 dilution in permeabilization/blocking buffer of monoclonal antibodies recognizing F and/or NP will be added to the wells. The plate will be incubated for 1 hour at room temperature.

The antibody solution will be aspirated. The wells will be washed three times with wash buffer. A 1:1000 dilution in permeabilization/blocking buffer of a secondary antibody (horse radish peroxidase-conjugated goat anti-mouse IgG heavy and light chain) will be added to the wells. The plate will be incubated for 1 hour at room temperature.

The secondary antibody will be aspirated from the wells. The wells will be washed three times with wash buffer. Trypan blue substrate will be added to the wells. The plate will be incubated for 10 minutes at room temperature. The plate will be washed once with distilled water and aspirated dry.

The stained syncytia will be counted using a UV analyzer with image acquisition and counting software.

Syncytia will be counted in control wells that will have been incubated with virus that was not mixed with serum. The syncytia will be counted in the sample wells. Two replicates of each well will be counted and averaged. The proportion of syncytia in control wells that remain in the sample wells will be calculated. The dilution values of serum that yield 60% neutralization of virus are calculated by linear regression. The inverse of this dilution is the 60% neutralization titer.

Example 2

The RSV F Subunit Vaccine Boosts the RSV-Specific Antibody Response in Previously RSV-Infected Cotton Rats and Mice 1. Methods
RSV F Trimer Subunit Vaccine The RSV F trimer is a recombinant protein comprising the ectodomain of RSV F with a deletion in the fusion peptide region preventing association with other trimers. The resulting construct forms a homogeneous trimer, as observed by size exclusion chromatography, and has an expected phenotype consistent with a postfusion F conformation as observed by electron microscopy. The protein was expressed and purified from CHO cells. The resulting protein sample exhibited greater than 95% purity. For the in vivo evaluation of the F subunit vaccine with aluminum hydroxide (alum), F subunit was adsorbed on 2 mg/ml alum using 10 mM histidine buffer pH 6.3, adjusted for isotonicity with sodium chloride. The F subunit was adsorbed on alum overnight with gentle stirring at 2-8° C. For evaluation of the F subunit vaccine with MF59, the protein was diluted into PBS and mixed with an equal volume of 2×MF59 within 2 hours before immunization and mixed by gentle inversion.
Vaccination and Infection of Cotton Rats and Mice Female cotton rats (*Sigmodon hispidis*) were obtained from Harlan Laboratories and female BALB/c mice were obtained from Charles River Laboratories. All studies were approved and performed according to Novartis Animal Care and Use Committee. Groups of 7 cotton rats were inoculated intranasally (i.n.) with $1\times10^5$ plaque forming units (pfu) RSV in 100 µl and immunized intramuscularly (i.m.) with the RSV F subunit vaccine (100 µl total volume in one hind limb) 7 weeks later. Groups of 7 mice were inoculated i.n. with $1\times10^6$ pfu RSV in 50 µl and immunized i.m. with the RSV F subunit vaccine (100 µl total volume split between two hind limbs) 11 and 15 weeks later. Two untreated naive control animals were included in each study. Serum samples were collected at various time points after the RSV inoculation and 2 weeks after each RSV F subunit immunization.
RSV F-Specific ELISA Individual cotton rat or mouse serum samples were assayed for the presence of RSV F-specific IgG by enzyme-linked immunosorbent assay (ELISA). ELISA plates (Maxi-iSorp 96-well, Nunc) were coated overnight at 4° C. with 1 µg/ml purified RSV F protein in PBS. After washing (PBS with 0.1% Tween-20), plates were blocked with Superblock Blocking Buffer in PBS (Thermo Scientific) for at least 1 hr at 37° C. The plates were then washed, 5-fold serial dilutions of serum in assay diluent (PBS with 0.1% Tween-20 and 5% goat serum) from experimental or control animals were added in duplicate, and plates were incubated for 2 hr at 37° C. After washing, plates were incubated with horse radish peroxidase (HRP)-conjugated anti-IgG detection antibody diluted in assay diluent (1:50,000 dilution of chicken anti-cotton rat IgG [Immunology Consultants Laboratory, Inc,] or 1:30,000 dilution of goat anti-mouse IgG [Southern Biotech]) for 1 hr at 37° C. Finally, plates were washed and 100 µl of TMB peroxidase substrate solution (Kirkegaard & Perry Laboratories, Inc) was added to each well. Reactions were stopped by addition of 100 µl of 1M $H_3PO_4$, and absorbance was read at 450 nm using a plate reader. For each serum sample, a plot of optical density (OD) versus logarithm of the reciprocal serum dilution was generated by nonlinear regression (GraphPad Prism). Titers were defined as the reciprocal serum dilution at an $OD_{450\ nm}$ of approximately 0.6, normalized to a standard serum sample included on every plate (cotton rat standard—pooled sera from RSV-infected cotton rats with a defined titer of 1:2500, mouse standard—pooled sera from adjuvanted RSV F subunit-vaccinated BALB/c mice with a defined titer of 1:269,773). If the titer for an individual sample was below the first serum dilution tested, 1:25, it was assigned a titer of 1:5 for purposes of calculating the group mean.
RSV Neutralization Assay Serum samples were tested for the presence of RSV neutralizing antibodies by a foci-reduction neutralization test. Two-fold serial dilutions of heat inactivated (HI)-serum (in PBS with 5% HI-FBS) were added to an equal volume of RSV Long previously titered to give approximately 115 pfu/25 µl. Serum/virus mixtures were incubated for 2 hours at 37° C. and 5% $CO_2$, to allow virus neutralization to occur, and then 25 µl of this mixture (containing approximately 115 pfu) was inoculated on duplicate wells of HEp-2 cells in 96-well plates. After 2 hr at 37° C. and 5% CO2, the cells were overlaid with 0.75% methylcellulose containing medium with 5% HI-FBS and incubated for 40-46 hours. The number of syncytia were enumerated by immunostaining with monoclonal antibodies specific to the RSV fusion and nucleoproteins (AbD Serotec) followed by automated counting (CTL Immunospot S5 UV Analyzer). The neutralization titer is defined as the reciprocal of the serum dilution producing at least a 60% reduction in number of syncytia per well, relative to controls (no serum). If the titer of a sample was below the first serum dilution tested, 1:20, it was assigned a titer of 1:10 for purposes of calculating the group mean.

2. Results and Conclusions

To model the use of the F subunit vaccine to increase serum neutralizing titers in previously RSV-infected adult humans, groups of 7 adult female cotton rats or mice were inoculated i.n. with RSV and immunized i.m. with unadjuvanted or adjuvanted RSV F subunit vaccine 7 weeks later (cotton rats) or 11 and 15 weeks later (mice). The results of these experiments demonstrate that the RSV F subunit vaccine effectively boosted the serum F-specific IgG and RSV neutralizing responses primed by RSV infection in mice and cotton rats (Tables 1 and 2). The fold boost in RSV-specific antibody response afforded by RSV F subunit vaccination was greater in mice (10 to 50-fold increase in neutralization titer and 9 to 51-fold increase in F-specific IgG titer) than in cotton rats (4 to 6-fold increase in neutralization titer and 7 to 25-fold increase in F-specific IgG titer), but in both species the increase in titer was largely independent of antigen doses and adjuvant evaluated (Tables 1 and 2).

were intraperitoneally (i.p.) inoculated (10 ml/kg) with one of three pools of undiluted cotton rat serum: 1) "normal"—collected from naive cotton rats, 2) "RSV"—cotton rats

TABLE 1

Immunogenicity of RSV F subunit vaccine in RSV-seropositive cotton rats

| | | Serum F-specific IgG titer[c] | | Serum RSV neutralization titer[d] | | |
|---|---|---|---|---|---|---|
| Gr. | Infect[a] (wk 0) | Vaccination[b] (wk 7) | 7 wk post infection | 2 wk post vaccination | 4 wk post infection | 7 wk post infection | 2 wk post vaccination |
| A | RSV | — | 2.90 ± 0.19 | 2.80 ± 0.33 | 2.69 ± 0.03 | 2.44 ± 0.06 | 2.71 ± 0.03 |
| B | RSV | 5 µg F subunit | 2.80 ± 0.35 | 4.16 ± 0.16 | 2.81 ± 0.08 | 2.64 ± 0.22 | 3.36 ± 0.13 |
| C | RSV | 5 µg F subunit/MF59 | 2.93 ± 0.33 | 4.32 ± 0.18 | 2.64 ± 0.13 | 2.65 ± 0.05 | 3.39 ± 0.10 |
| D | RSV | 0.5 µg F subunit/MF59 | 2.92 ± 0.24 | 3.99 ± 0.19 | 2.47 ± 0.02 | 2.67 ± 0.14 | 3.36 ± 0.05 |
| E | RSV | 0.05 µg F subunit/MF59 | 2.90 ± 0.23 | 3.87 ± 0.17 | 2.68 ± 0.07 | 2.47 ± 0.09 | 3.25 ± 0.08 |
| F | RSV | 5 µg F subunit/alum | 3.24 ± 0.52 | 4.07 ± 0.14 | 2.80 ± 0.20 | 2.64 ± 0.13 | 3.24 ± 0.11 |
| G | RSV | 0.5 µg F subunit/alum | 2.79 ± 0.12 | 3.92 ± 0.16 | 2.61 ± 0.09 | 2.39 ± 0.11 | 3.04 ± 0.06 |
| H | RSV | 0.05 µg F subunit/alum | 3.06 ± 0.17 | 4.05 ± 0.22 | 2.80 ± 0.17 | 2.62 ± 0.06 | 3.24 ± 0.22 |
| I | — | — | n.t. | n.t. | 1.00 | 1.32 | 1.00 |

Abbreviations:
Gr—group,
wk—week,
n.t.—not tested
[a] $1 \times 10^5$ pfu RSV i.n.
[b] i.m.
[c] mean $\log_{10}$ titer ± standard deviation of 7 individual animals per group
[d] mean $\log_{10}$ titer ± range of 2 pools of 3-4 animals per group (1 pool of 2 animals in Gr. I)

TABLE 2

Immunogenicity of RSV F subunit vaccine in RSV-seropositive BALB/c mice

| | | Serum F-specific IgG titer[c] | | | Serum RSV neutralization titer[d] | | |
|---|---|---|---|---|---|---|---|
| Gr. | Infect[a] (wk 0) | Vaccination[b] (wk 11 & 15) | 11 wk post infection | 2 wk post 1st vaccination | 2 wk post 2nd vaccination | 11 wk post infection | 2 wk post 1st vaccination | 2 wk post 2nd vaccination |
| A | RSV | — | 4.03 ± 0.11 | 4.09 ± 0.12 | 4.10 ± 0.12 | 2.11 ± 0.10 | 2.18 ± 0.03 | 2.50 ± 0.08 |
| B | RSV | 5 µg F subunit | 4.02 ± 0.10 | 5.36 ± 0.11 | 5.40 ± 0.10 | 2.03 ± 0.14 | 3.24 ± 0.15 | 3.42 ± 0.11 |
| C | RSV | 0.5 µg F subunit | 4.18 ± 0.11 | 5.29 ± 0.06 | 5.43 ± 0.07 | 2.39 ± 0.10 | 3.39 ± 0.03 | 3.54 ± 0.07 |
| D | RSV | 0.05 µg F subunit | 4.07 ± 0.16 | 5.15 ± 0.11 | 5.24 ± 0.08 | 1.98 ± 0.10 | 3.03 ± 0.07 | 3.28 ± 0.08 |
| E | RSV | 5 µg F subunit/MF59 | 3.99 ± 0.16 | 5.59 ± 0.15 | 5.72 ± 0.09 | 1.98 ± 0.26 | 3.34 ± 0.34 | 3.38 ± 0.10 |
| F | RSV | 0.5 µg F subunit/MF59 | 4.00 ± 0.30 | 5.55 ± 0.11 | 5.78 ± 0.12 | 2.04 ± 0.12 | 3.40 ± 0.09 | 3.39 ± 0.20 |
| G | RSV | 0.05 µg F subunit/MF59 | 3.96 ± 0.20 | 5.61 ± 0.09 | 5.68 ± 0.09 | 1.85 ± 0.37 | 3.32 ± 0.08 | 3.64 ± 0.15 |
| H | RSV | 5 µg F subunit/alum | 4.02 ± 0.10 | 5.46 ± 0.14 | 5.63 ± 0.06 | 1.75 ± 0.13 | 3.45 ± 0.09 | 3.31 ± 0.17 |
| I | RSV | 0.5 µg F subunit/alum | 3.91 ± 0.19 | 5.22 ± 0.14 | 5.57 ± 0.14 | 2.05 ± 0.19 | 3.23 ± 0.14 | 3.52 ± 0.02 |
| J | RSV | 0.05 µg F subunit/alum | 4.04 ± 0.11 | 5.06 ± 0.13 | 5.35 ± 0.16 | 2.22 ± 0.15 | 3.16 ± 0.17 | 3.54 ± 0.10 |
| K | — | — | 0.70 | 0.70 | 0.70 | 1.00 | 1.00 | 1.00 |

Abbreviations:
Gr—group,
wk—week
[a] $1 \times 10^6$ pfu RSV i.n.
[b] i.m.
[c] mean $\log_{10}$ titer ± standard deviation of 7 individual animals per group (2 animals in Gr. K)
[d] mean $\log_{10}$ titer ± range of 2 pools of 3-4 animals per group (1 pool of 2 animals in Gr. K)

Example 3

Protection by Passive Transfer of Antibody from RSV-Infected, F Subunit Vaccine-Boosted Cotton Rats and Mice 1. Methods
Serum Transfer and RSV Infection of Cotton Rats and Mice Female cotton rats (*Sigmodon hispidis*) were obtained from Harlan Laboratories and female BALB/c mice were obtained from Charles River Laboratories. All studies were approved and performed according to Novartis Animal Care and Use Committee. Groups of 7-8 female, adult cotton rats were infected with $1 \times 10^5$ pfu RSV and serum was collected 7 weeks later, or 3) "RSV+subunit"—cotton rats were infected with $1 \times 10^5$ pfu RSV and vaccinated 7 weeks later with F subunit. Serum was collected 2 and 4 weeks after F subunit vaccination (pooled from animals vaccinated with 0.05 µg, 0.5 µg, or 5 µg F subunit, either unadjuvanted, or adjuvanted with alum or MF59, similar to the cotton rat experiment described in Example 2). An additional group of animals was injected with 10 ml/kg of a 1:3 dilution of the "RSV+subunit" serum pool.

Groups of 4-8 BALB/c mice were i.p. inoculated (20 ml/kg) with one of two pools of undiluted mouse serum: 1) "normal"—collected from naive BALB/c mice, or 2)

"RSV+subunit"—BALB/c were infected with $1\times10^6$ pfu RSV and vaccinated 7 and 11 weeks later with F subunit. Serum was collected 2 and 4 weeks after the $1^{st}$ vaccination and 2 weeks after the $2^{nd}$ vaccination and pooled (animals were vaccinated with 0.05 µg, 0.5 µg, or 5 µg F subunit, either unadjuvanted, or adjuvanted with alum or MF59, similar to the mouse experiment described in Example 2). An additional group of mice was injected with 20 ml/kg of a 1:3 dilution of the "RSV+subunit" serum pool.

Two days after serum transfer all cotton rats and mice, plus untreated control animals, were infected intranasally with RSV ($1\times10^5$ pfu for cotton rats and $3\times10^6$ pfu for mice).

RSV Plaque Assay

RSV load in the lung after infection was determined by plaque assay. Lungs were harvested and weighed 4 days (mice) or 5 days (cotton rats) post RSV infection and one right lobe was placed into medium with 25% sucrose and disrupted with a tissue homogenizer. Cell-free supernatants from these samples were stored at −80° C. To assay for infectious virus, dilutions of clarified lung homogenate (in PBS with 5% HI-FBS) were inoculated on confluent HEp-2 cell monolayers in a volume of 200 µl/well of a 12-well plate. After 2 hrs with periodic gentle rocking (37° C., 5% $CO_2$), the inoculum was removed, and cells were overlaid with 1.5 ml of 1.25% SeaPlaque agarose in medium supplemented with 5% HI-FBS, glutamine, and antibiotics. After 3-4 days of incubation, cells were again overlaid with 1 ml of 1.25% agarose in medium containing 0.1% neutral red (Sigma). Plaques are counted one day later with the aid of a light box. If the viral load for an individual animal was below than the assay limit of detection (~200 pfu/g lung), it was assigned a titer of 100 pfu/g lung for purposes of calculating the group mean.

RSV Neutralization Assay and F-Specific IgG ELISA

These assays were performed as described in Example 2.

2. Results and Conclusions

To model the protection of human infants by passive transfer of antibodies with increased RSV-neutralizing titers from their previously RSV-infected, subunit F-boosted mothers, we infected adult cotton rats or mice with RSV, boosted some of them with the RSV F subunit vaccine 7 weeks later, harvested serum, and injected the serum i.p. into RSV-uninfected, unimmunized adult cotton rats or mice (4-8 animals per group, cotton rat serum injected into cotton rats, and mouse serum injected into mice). Two days after serum transfer, all animals were challenged with RSV i.n.

Figure 1B:
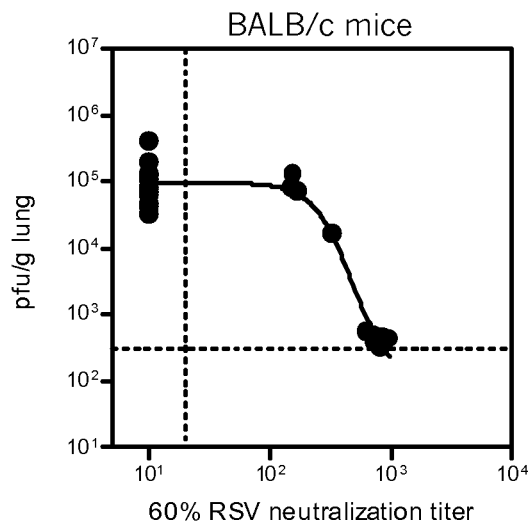

RSV-neutralizing activity could readily be detected in the serum of recipient rodents one day after passive-transfer of donor serum (Tables 3 and 4). Rodents that received serum from RSV-infected, F subunit vaccine-immunized donors had the highest serum RSV neutralization titers after transfer and the lowest lung viral loads after RSV challenge, when compared to rodents that received serum from RSV-infected but unimmunized donors, normal serum, or no serum prior to RSV challenge (Tables 3 and 4). These data illustrate that passively-transferred serum can protect from RSV challenge, and that the higher the neutralization titer of the transferred serum, the greater the protection from RSV (Tables 3 and 4 and FIGS. 1A and 1B). Because recipients of serum transferred from RSV-infected, subunit F vaccine-immunized cotton rats, but not from RSV-infected but unimmunized cotton rats, were protected from RSV challenge, these results support the protection of human infants born to pregnant women (who will inevitably have experienced past RSV infections) immunized with the RSV F subunit vaccine.

To determine the half life of RSV-specific antibody after passive transfer, groups of rodents were injected i.p. with undiluted serum from RSV-infected, F subunit vaccine-immunized rodents, and the RSV neutralization titer in the recipients was measured at various time points post transfer. The results of these studies demonstrate that the half life of passively-transferred antibody was approximately 2 weeks in both cotton rats and mice (Tables 5 and 6). Therefore, every two-fold increase in neutralization titer above the protective threshold by the RSV F subunit vaccine should extent protection in recipients of passive antibody by 2 weeks, in these rodent models.

TABLE 3

Protection by passive transfer of serum from RSV-infected, F subunit vaccine-immunized cotton rats

| | | | 1 day post serum transfer | | 5 days post |
| --- | --- | --- | --- | --- | --- |
| Gr. | Serum transferred[a] (day 0) | Chal.[b] (day 2) | Serum F-specific IgG titer[c] | Serum RSV neutralization titer[d] | RSV challenge Lung viral load[e] |
| A | RSV + subunit | RSV | 2.81 ± 0.09 | 2.52 ± 0.09 | 3.18 ± 0.42 |
| B | 1:3 RSV + subunit | RSV | 2.43 ± 0.30 | 2.16 ± 0.12 | 5.36 ± 0.47 |
| C | RSV | RSV | 1.64 ± 0.05 | 1.92 ± 0.15 | 5.48 ± 0.23 |
| D | normal | RSV | 0.70 ± 0.00 | 1.04 ± 0.12 | 5.82 ± 0.24 |
| E | — | RSV | 0.70 ± 0.00 | 1.00 ± 0.00 | 5.74 ± 0.35 |

Abbreviations:

Gr—group, chal—challenge

[a]pooled serum from RSV-infected, F-subunit vaccine-immunized ("RSV ± subunit"), RSV-infected, unvaccinated ("RSV"), or naive ("normal") cotton rats. 10 ml/kg of undiluted or 1:3 diluted serum, as indicated, was i.p. injected into groups of recipient cotton rats.

[b]$1 \times 10^5$ pfu RSV i.n.

[c-d]mean $\log_{10}$ titer ± standard deviation of 7-8 individual animals per group

[e]mean $\log_{10}$ pfu/g lung ± standard deviation of 7-8 individual animals per group

TABLE 4

Protection by passive transfer of serum from RSV-infected, F subunit vaccine-immunized BALB/c mice

| Gr. | Serum transferred[a] (day 0) | Chal.[b] (day 2) | 1 day post serum transfer | | 4 days post RSV challenge Lung viral load[e] |
|---|---|---|---|---|---|
| | | | Serum F-specific IgG titer[c] | Serum RSV neutralization titer[d] | |
| A | RSV + subunit | RSV | 4.85 ± 0.04 | 2.90 ± 0.06 | 2.65 ± 0.07 |
| B | 1:3 RSV + subunit | RSV | 4.30 ± 0.05 | 2.20 ± 0.20 | 4.78 ± 0.39 |
| D | normal | RSV | 0.70 ± 0.00 | 1.00 ± 0.00 | 4.95 ± 0.37 |
| E | — | RSV | 0.70 ± 0.00 | 1.04 ± 0.11 | 4.96 ± 0.26 |

Abbreviations:
Gr—group,
chal—challenge
[a] pooled serum from RSV-infected, F-subunit vaccine-boosted ("RSV + subunit") or naive ("normal") BALB/c mice. 20 ml/kg of undiluted or 1:3 diluted serum, as indicated, was injected i.p. into groups of recipient mice.
[b] $3 \times 10^6$ pfu RSV i.n.
[c-d] mean $\log_{10}$ titer ± standard deviation of 4-8 individual animals per group
[e] mean $\log_{10}$ pfu/g lung ± standard deviation of 4-8 individual animals per group

TABLE 5

Decay of serum RSV neutralization titers in cotton rat recipients of passive antibody

| Day post transfer[a] | Serum RSV neutralization titer[b] | Half life |
|---|---|---|
| 1 | 2.51 ± 0.00 | |
| 7 | 2.27 ± 0.01 | |
| 14 | 2.24 ± 0.05 | |
| 19 | 2.11 ± 0.14 | |
| 34 | 1.84 ± 0.08 | |
| 48 | 1.47 ± 0.06 | 15 days |

[a] 10 ml/kg of undiluted pooled serum from RSV-infected, F-subunit vaccine-immunized ("RSV ± subunit") cotton rats was injected i.p. into a group of 8 cotton rats
[b] mean $\log_{10}$ titer ± range of 2 pools of 4 animals

TABLE 6

Decay of serum RSV neutralization titers in mouse recipients of passive antibody

| Day post transfer[a] | Serum RSV neutralization titer[b] | Half life |
|---|---|---|
| 1 | 2.87 ± 0.01 | |
| 9 | 2.65 ± 0.04 | |
| 16 | 2.43 ± 0.03 | |
| 23 | 2.26 ± 0.08 | |
| 36 | 2.08 ± 0.02 | |
| 44 | 1.83 ± 0.04 | 14 days |

[a] 20 ml/kg of undiluted pooled serum from RSV-infected, F-subunit vaccine-immunized ("RSV + subunit") BALB/c mice was injected i.p. into a group of 13 BALB/c mice.
[b] mean $\log_{10}$ titer ± SEM of 2-3 pools of 4-5 animals Example 4

Induction of a Protective Immune Response by the RSV SAM™ Vaccine in Rodents in the Presence or Absence of Passively-Transferred RSV-Immune Serum 1. Methods
RSV SAM™ Vaccine An RSV SAM™ (Self Amplifying Message) vaccine (RNA replicon vaccine) that encoded the full length RSV F protein with a deletion in the fusion peptide region was used for these studies. The RNA was formulated with a cationic nanoemulsion (CNE, 4.4 mg/ml DOTAP, 0.5% SPAN 85, 0.5% Tween 80, 4.3% squalene in a 10 mM citrate buffer pH6.5 aqueous phase) prior to injection. CNE was prepared similar to charged MF59 as previously described (Ott et al., Journal of Controlled Release, volume 79, pages 1-5, 2002), with one major modification. DOTAP was dissolved in the squalene directly, and no organic solvent was used.

RNA was diluted to a concentration of 300 µg/ml in a 2 mM citrate buffer containing 20 mM NaCl and 560 mM sucrose. The RNA was added directly into an equal volume of CNE while vortexing lightly. The solution was allowed to sit at room temperature for up to 1 hour. Once complexed the resulting solution was diluted to the appropriate concentration and used within 1 hour.

Serum Transfer, Vaccination, and RSV Infection of Rodents

Neat or a 1:3 dilution of serum from adult female cotton rats that had been infected with RSV and boosted with the RSV SAM vaccine was injected i.p. (10 mg/kg) into groups of 16 RSV-naive, unimmunized adult cotton rats. Groups of control cotton rats were injected i.p. with undiluted normal cotton rat serum or were untreated. Half of the animals in each group were vaccinated i.m. with 15 µg of the RSV SAM vaccine (100 µl total volume in 1 hind limb) on days 2 and 20 of the study. All of the cotton rats were challenged i.n. with $1 \times 10^5$ pfu RSV on day 49, and 5 days later spleens and lungs were harvested for T cell and viral load analyses. A similar study was performed in BALB/c mice with passive transfer of RSV-immune or normal mouse serum followed by vaccination of a subset of each group with 15 µg of the RSV SAM vaccine (100 µA total volume split between 2 hind limbs), except that the serum dose was 20 ml/kg, the RSV SAM vaccines were administered on days 2 and 22, the groups included 5 additional animals from which spleens were harvested on day 36 for F-specific T cell analysis, mice were challenged with $3 \times 10^6$ pfu of RSV on day 45, and lungs and spleens were harvested on day 49. The pools of cotton rat and mouse serum used for transfer in these studies were identical to those used in Example 3.

RSV Neutralization Assay and F-Specific IgG ELISA

These assays were performed as described in Example 2.
RSV Plaque Assay

This assay was performed as described in Example 3.

Cotton Rat Functional T Cell Assay: Cell-Based ELISA for Secreted Cytokines

Antigen-specific secretion of cotton rat IFNγ and IL-4 was measured by ELISA using kits from R&D Systems with the following protocol modifications. Splenocytes ($3$-$4 \times 10^5$ live, nucleated cells) in 200 µL of serum-free T cell medium (RPMI, 10 mM HEPES, 100 µM non-essential amino acids, 50 µM 2-mercaptoethanol, and antibiotics) were added to plates coated with cytokine capture antibody. Cells were stimulated with a cocktail of 5 µM each of three RSV F peptides (F29-43, F49-63, and F247-261). Recombinant cytokine protein standards were diluted in T cell medium +1% FBS. After 24 hours secreted cytokines were detected based on manufacturer's recommendations. Results are reported as net pg/ml (average of triplicate wells with stimulus−average of triplicate wells without stimulus).

Mouse Functional T Cell Assay: Intracellular Cytokine Staining and Flow Cytometry Spleens were harvested at the indicated study days and processed into single cell-suspensions. When splenocytes from individual animals were assayed separately, 1 antigen-stimulated and 1 unstimulated culture was established for each animal, and when splenocytes from all the animals in a group were combined and assayed as a pool, 2 antigen-stimulated cultures and two unstimulated cultures were established for each pool. Antigen-stimulated cultures contained $1 \times 10^6$ splenocytes, RSV F peptides 85-93 and 249-258 (each at 1 mM), RSV F peptides 51-66, 164-178, and 309-323 (each at 5 mM), anti-CD28 mAb (1 µg/mL), and Brefeldin A (1:1000). Unstimulated cultures did not contain RSV F peptides, and were otherwise identical to the stimulated cultures. After culturing for 6 hours at 37° C., cultures were processed for immunofluorescence. Cells were washed and then stained with fluorescently labeled anti-CD4 and anti-CD8 monoclonal antibodies (mAb). Cells were washed again and then fixed with Cytofix/Cytoperm for 20 minutes. The fixed cells were then washed with Perm-wash buffer and then stained with fluorescently-labeled mAbs specific for IFNγ, TNFα, IL-2, and IL-5. Stained cells were washed and then analyzed on an LSR II flow cytometer. FlowJo software was used to analyze the acquired data. The CD4+8- and CD8+4-T cell subsets were analyzed separately. For each subset in a given sample the percent cytokine-positive cells was determined. The percent RSV F antigen-specific T cells was calculated as the difference between the % cytokine-positive cells in the antigen-stimulated cultures and the percent cytokine-positive cells in the unstimulated cultures.

2. Results and Conclusions

To model the use of the RSV SAM vaccine in RSV-naive infants we evaluated the immunogenicity and efficacy of the RSV SAM vaccine in RSV-naive cotton rats and BALB/c mice. The RSV SAM vaccine was immunogenic in both species, eliciting serum RSV neutralization titers of 1:776 in cotton rats and 1:209 in mice when measured 3-4 weeks after the $2^{nd}$ i.m. vaccination of 15 µg of the RSV SAM vaccine (Table 7 and 8, groups H). In mice, the RSV SAM vaccine elicited a robust F-specific CD8+ T cell response and a moderate Th1 CD4+ T cell response, characterized by production of IFNγ, TNFα, and IL-2 with no significant production of IL-5 (Table 9, group H). In both species the RSV SAM RNA vaccine provided almost complete protection from a nasal RSV challenge administered 3-4 weeks after the $2^{nd}$ RNA vaccination, as evidenced by a greater than 99.9% reduction in pulmonary viral loads compared to unimmunized control animals (Tables 7 and 8, group H compared to group D).

RSV-neutralizing antibodies are passively transferred from mother to infant through the placenta and protect infants from severe RSV disease in the first few months of life; however, these same antibodies may also interfere with the active immune response to the RSV SAM vaccine. We therefore also investigated whether immunogenicity and efficacy of the RNA SAM vaccine in rodents was affected by passively-acquired RSV-specific antibody. RSV-neutralizing and F-specific IgG responses could readily be detected in the serum of recipient rodents one day after passive-transfer of neat or a 1:3 dilution of serum from RSV-infected, RSV F subunit vaccine-boosted rodents (Tables 7-8). Forty-eight days after transfer of the RSV-immune serum, the RSV neutralization titers had dropped to very low or undetectable levels in unvaccinated recipient cotton rats, but were >1:50 in those vaccinated with RNA (Table 7, groups A and B compared to groups E and F). These data demonstrate that the RSV SAM vaccine was able to induce a RSV neutralizing response in the presence of passively-transferred immune serum. However, the RSV SAM vaccine-induced neutralizing response was approximately 10-fold lower in the presence of passive RSV-specific antibody than in the absence of this antibody (Table 7, groups E and F compared to groups G and H). In BALB/c mice, RSV neutralizing titers measured after the second RSV SAM vaccination were similar in the presence or absence of passively-transferred RSV-specific antibody (Table 8, groups E and F compared to groups G and H). Although these data suggest that passively-transferred antibody does not inhibit the RSV SAM vaccine-induced antibody response in mice, it should be noted that the neutralizing titer 44 days post serum transfer in RSV SAM-vaccinated mice was a combination of the titer induced by the RSV SAM vaccine and that remaining from the passive transfer (neutralizing antibody was still detected in unvaccinated mice at this time point). Therefore, it is likely that passively-transferred RSV-specific antibody inhibited the RSV SAM vaccine-induced antibody response to some extent in mice as well.

Although passively-transferred RSV-specific antibody partially suppressed the RSV SAM-induced antibody response in rodents, it did not suppress the RSV SAM-induced T cell response. In cotton rats, the magnitude of the splenic F-specific IFNγ response 5 days after RSV infection was equivalent in RSV SAM-vaccinated animals regardless of whether or not the animals had been dosed with serum prior to vaccination (Table 10, group E compared to H). The results were similar in mice, where the splenic F-specific CD4+ T and CD8+ responses measured 14 days after the second RSV SAM vaccination, or 4 days after the RSV infection were equivalent in the presence or absence of passively-transferred serum (Tables 9 and 11, group E compared to G and H).

To determine whether the RSV SAM vaccine was capable of inducing a protective immune response in the presence of passive antibody from RSV-infected, F subunit vaccine-boosted donors, cotton rats or mice were inoculated with RSV-immune serum, vaccinated twice with the RSV SAM vaccine, and then infected with RSV 3-4 weeks later. Four to five days after infection the lung viral load in these animals was at least 1.4 $\log_{10}$ lower than that in control animals not dosed with serum or RNA prior to RSV infection (Tables 7 and 8, groups E and F compared to D). Because the passively-transferred antibody had been metabolized by this time, and therefore did not protect unimmunized animals from RSV challenge (Tables 7 and 8, groups A and B), any protective effect can be attributed to the RSV SAM vaccine. These data therefore demonstrate that the RSV SAM vaccine is able to induce a protective immune response in the presence of passively-transferred RSV-specific antibody. However, the protective efficacy of the RSV SAM vaccine was greater in the absence of passive RSV-specific serum (Tables 7 and 8, groups G and H).

In conclusion, these results support the use of the RSV SAM vaccine in infants born to mothers vaccinated with the RSV F subunit vaccine, as they provide preclinical evidence in two rodent models that the RSV SAM vaccine is able to induce a protective immune response in the presence of passively-transferred, RSV-specific antibody. Although the RSV SAM vaccine-induced RSV neutralization response was somewhat suppressed by the passive antibody, the T cell response was not, and therefore the likely mechanism of protection was cell-mediated immunity.

As summarized in Table 12, the data from Examples 2-4 support the RSV dual vaccination strategy; only those cotton rats dosed with serum from RSV-infected, F subunit vaccine-immunized donors on day 0, and then vaccinated with the RSV SAM vaccine on days 2 and 20, were protected from an early (day 2) and a late (day 49) RSV challenge.

TABLE 7

Immunogenicity and efficacy of the RSV SAM vaccine in cotton rats in the presence or absence of passively-transferred RSV-specific antibody

| Gr. | Serum transfer[a] (d 0) | Vacc.[b] (d 2 & 20) | Chal.[c] (d 49) | Serum F-specific IgG titer[d] | | | |
|---|---|---|---|---|---|---|---|
| | | | | 1 d post serum trans. (d 1) | 17 d post 1st vacc. (d 19) | 28 d post 2nd vacc. (d 48) | 5 d post RSV chal. (d 54) |
| A | RSV + subunit | — | RSV | 2.94 ± 0.07 | 2.23 ± 0.06 | 0.70 ± 0.00 | 0.70 ± 0.00 |
| B | 1:3 RSV + subunit | — | RSV | 2.36 ± 0.06 | 1.67 ± 0.06 | 0.70 ± 0.00 | 0.70 ± 0.00 |
| C | normal | — | RSV | 0.70 ± 0.00 | 0.70 ± 0.00 | 0.70 ± 0.00 | 0.70 ± 0.00 |
| D | — | — | RSV | 0.70 ± 0.00 | 0.70 ± 0.00 | 0.70 ± 0.00 | 0.70 ± 0.00 |
| E | RSV + subunit | RSV SAM | RSV | 2.83 ± 0.09 | 2.14 ± 0.16 | 2.03 ± 0.30 | 2.42 ± 0.30 |
| F | 1:3 RSV + subunit | RSV SAM | RSV | 2.34 ± 0.08 | 2.02 ± 0.22 | 2.75 ± 0.33 | 2.99 ± 0.28 |
| G | normal | RSV SAM | RSV | 0.70 ± 0.00 | 3.14 ± 0.19 | 3.52 ± 0.19 | 3.67 ± 0.14 |
| H | — | RSV SAM | RSV | 0.70 ± 0.00 | 3.32 ± 0.11 | 3.40 ± 0.21 | 3.48 ± 0.27 |

| Gr. | Serum RSV neutralization titer[e] | | | | Lung viral load[f] |
|---|---|---|---|---|---|
| | 1 d post serum trans. (d 1) | 17 d post 1st vacc. (d 19) | 28 d post 2nd vacc. (d 48) | 5 d post RSV chal. (d 54) | 5 d post RSV chal. (d 54) |
| A | 2.51 ± 0.00 | 2.11 ± 0.14 | 1.47 ± 0.06 | 1.73 ± 0.14 | 4.90 ± 0.39 |
| B | 2.09 ± 0.01 | 1.73 ± 0.09 | 1.17 ± 0.17 | 1.72 ± 0.13 | 4.82 ± 0.39 |
| C | 1.17 ± 0.17 | 1.20 ± 0.20 | 1.16 ± 0.16 | 1.93 ± 0.17 | 5.42 ± 0.25 |
| D | 1.00 ± 0.00 | 1.00 ± 0.00 | 1.00 ± 0.00 | 1.69 ± 0.14 | 5.17 ± 0.35 |
| E | 2.44 ± 0.02 | 1.91 ± 0.04 | 1.86 ± 0.10 | 2.23 ± 0.09 | 3.82 ± 0.42 |
| F | 2.09 ± 0.04 | 1.79 ± 0.05 | 1.73 ± 0.15 | 2.37 ± 0.01 | 3.68 ± 0.72 |
| G | 1.00 ± 0.00 | 2.36 ± 0.13 | 3.06 ± 0.02 | 3.18 ± 0.01 | 2.18 ± 0.19 |
| H | 1.00 ± 0.00 | 2.58 ± 0.11 | 2.89 ± 0.15 | 3.00 ± 0.22 | 2.12 ± 0.17 |

Abbreviations:
Gr—group,
d—day,
trans—transfer,
vacc—vaccination,
chal—challenge

[a]pooled serum from RSV-infected, F-subunit vaccine-immunized ("RSV + subunit") or naive ("normal") cotton rats. 10 ml/kg of undiluted or 1:3 diluted serum, as indicated, was injected i.p. into groups of recipient cotton rats
[b]15 μg RSV SAM vaccine i.m. or no vaccination
[c]1 × 10^5 pfu RSV i.n.
[d]mean $\log_{10}$ titer ± standard deviation of 7-8 individual animals per group
[e]mean $\log_{10}$ titer ± range of 2 pools of 3-4 animals per group
[f]mean $\log_{10}$ pfu/g lung ± standard deviation of 7-8 individual animals per group

TABLE 8

Immunogenicity and efficacy of the RSV SAM RNA vaccine in BALB/c mice in the presence or absence of passively-transferred RSV-specific antibody

| | | | | Serum F-specific IgG titer | | | |
|---|---|---|---|---|---|---|---|
| Gr. | Serum transfer[a] (d 0) | Vacc.[b] (d 2 & 22) | Chal.[c] (d 45) | 1 d post serum trans. (d 1) | 1 d post 2$^{nd}$ vacc. (d 23) | 22 d post 2$^{nd}$ vacc. (d 44) | 4 d post RSV chal. (d 49) |
| A | RSV + subunit | — | RSV | 4.88 ± 0.06 | 4.30 ± 0.07 | 3.69 ± 0.32 | 3.98 ± 0.06 |
| B | 1:3 RSV + subunit | — | RSV | 4.28 ± 0.16 | 3.67 ± 0.14 | 3.29 ± 0.19 | 3.18 ± 0.22 |
| C | normal | — | RSV | 0.07 ± 0.00 | n.t. | 0.07 ± 0.00 | 0.07 ± 0.00 |
| D | — | — | RSV | 0.07 ± 0.00 | n.t. | 0.07 ± 0.00 | 0.07 ± 0.00 |
| E | RSV + subunit | RSV SAM | RSV | 4.88 ± 0.05 | 4.16 ± 0.08 | 3.70 ± 0.09 | 3.46 ± 0.12 |
| F | 1:3 RSV + subunit | RSV SAM | RSV | 4.34 ± 0.04 | 3.61 ± 0.05 | 3.20 ± 0.03 | 3.17 ± 0.08 |
| G | normal | RSV SAM | RSV | 0.07 ± 0.00 | 3.55 ± 0.42 | 4.38 ± 0.55 | 4.29 ± 0.53 |
| H | — | RSV SAM | RSV | 0.07 ± 0.00 | 3.35 ± 0.90 | 4.11 ± 0.40 | 3.98 ± 0.37 |

| | Serum RSV neutralization titer[e] | | | | Lung viral load[f] |
|---|---|---|---|---|---|
| Gr. | 1 d post serum trans. (d 1) | 1 d post 2$^{nd}$ vacc. (d 23) | 22 d post 2$^{nd}$ vacc. (d 44) | 4 d post RSV chal. (d 49) | 4 d post RSV chal. (d 49) |
| A | 2.87 ± 0.01 | 2.26 ± 0.08 | 1.83 ± 0.04 | 1.86 ± 0.01 | 4.91 ± 0.24 |
| B | 2.39 ± 0.02 | 1.78 ± 0.04 | 1.44 ± 0.01 | 1.54 ± 0.01 | 5.02 ± 0.31 |
| C | 1.00 ± 0.00 | 1.00 ± 0.00 | 1.00 ± 0.00 | 1.16 ± 0.16 | 5.14 ± 0.40 |
| D | 1.00 ± 0.00 | 1.00 ± 0.00 | 1.00 ± 0.00 | 1.00 ± 0.00 | 5.21 ± 0.42 |
| E | 2.95 ± 0.08 | 2.12 ± 0.11 | 2.47 ± 0.11 | 2.62 ± 0.15 | 3.58 ± 0.46 |
| F | 2.41 ± 0.12 | 1.73 ± 0.11 | 2.01 ± 0.07 | 2.03 ± 0.14 | 3.12 ± 0.47 |
| G | 1.00 ± 0.00 | 1.00 ± 0.00 | 1.85 ± 0.13 | 2.24 ± 0.22 | 2.11 ± 0.22 |
| H | 1.00 ± 0.00 | 1.00 ± 0.00 | 2.32 ± 0.12 | 2.18 ± 0.40 | 2.10 ± 0.18 |

Abbreviations:
Gr—group,
d—day,
trans—transfer,
vacc—vaccination,
chal—challenge,
n.t.—not tested
[a]pooled serum from RSV-infected, F-subunit vaccine-boosted ("RSV + subunit") or naive ("normal") mice. 20 ml/kg of undiluted or 1:3 diluted serum, as indicated, was injected i.p. into groups of recipient mice
[b]15 μg RSV SAM vaccine i.m. or no vaccination
[c]3 × 10$^6$ pfu RSV i.n.
[d]mean log$_{10}$ titer ± standard deviation of 8-13 individual animals per group
[e]mean log$_{10}$ titer ± range of 2 pools of 2-3 pools of 3-4 animals per group
[f]mean log$_{10}$ pfu/g lung ± standard deviation of 8 individual animals per group

TABLE 9

F-specific T cell responses induced by the RSV SAM vaccine in BALB/c mice in the presence or absence of passively-transferred RSV-specific antibody

| | | | | % F-specific cytokine$^+$ per CD4$^{+d}$ 14 days post 2$^{nd}$ vacc. (d 36) | | | |
|---|---|---|---|---|---|---|---|
| Gr. | Serum transfer[a] (d 0) | Vacc.[b] (d 2 & 22) | Chal.[c] (d 45) | IFNγ | TNFα | IL-2 | IL-5 |
| A | RSV ± subunit | — | RSV | 0.00 ± 0.00 | 0.00 ± 0.00 | 0.00 ± 0.00 | 0.00 ± 0.00 |
| B | 1:3 RSV ± subunit | — | RSV | n.t. | n.t. | n.t. | n.t. |
| C | normal | — | RSV | n.t. | n.t. | n.t. | n.t. |
| D | — | — | RSV | 0.00 ± 0.01 | 0.00 ± 0.00 | 0.00 ± 0.00 | 0.00 ± 0.00 |
| E | RSV ± subunit | RSV SAM | RSV | 0.08 ± 0.05 | 0.12 ± 0.08 | 0.12 ± 0.08 | 0.00 ± 0.00 |
| F | 1:3 RSV ± subunit | RSV SAM | RSV | 0.07 ± 0.02 | 0.16 ± 0.04 | 0.15 ± 0.03 | 0.01 ± 0.01 |

TABLE 9-continued

F-specific T cell responses induced by the RSV SAM vaccine in BALB/c mice in the presence or absence of passively-transferred RSV-specific antibody

| | | | | | | |
|---|---|---|---|---|---|---|
| G | normal | RSV SAM | RSV | 0.04 ± 0.02 | 0.09 ± 0.02 | 0.10 ± 0.02 | 0.00 ± 0.01 |
| H | — | RSV SAM | RSV | 0.05 ± 0.03 | 0.12 ± 0.05 | 0.12 ± 0.06 | 0.01 ± 0.01 |

| | % F-specific cytokine+ per CD8+e 14 days post 2nd vacc. (d 36) | | | |
|---|---|---|---|---|
| Gr. | IFNγ | TNFα | IL-2 | IL-5 |
| A | 0.01 ± 0.02 | 0.01 ± 0.01 | 0.00 ± 0.01 | 0.02 ± 0.02 |
| B | n.t. | n.t. | n.t. | n.t. |
| C | n.t. | n.t. | n.t. | n.t. |
| D | 0.00 ± 0.01 | 0.01 ± 0.02 | 0.01 ± 0.01 | 0.02 ± 0.03 |
| E | 0.77 ± 0.50 | 0.69 ± 0.42 | 0.17 ± 0.10 | 0.01 ± 0.02 |
| F | 1.11 ± 0.62 | 1.00 ± 0.64 | 0.27 ± 0.06 | 0.01 ± 0.01 |
| G | 1.16 ± 0.30 | 1.06 ± 0.25 | 0.26 ± 0.09 | 0.03 ± 0.03 |
| H | 2.47 ± 1.55 | 2.24 ± 1.38 | 0.51 ± 0.33 | 0.01 ± 0.02 |

Abbreviations:
Gr—group,
d—day,
vacc—vaccination,
chal—challenge,
n.t.—not tested

[a] pooled serum from RSV-infected, F-subunit vaccine-boosted ("RSV + subunit") or naive ("normal") mice. 20 ml/kg of undiluted or 1:3 diluted serum, as indicated, was injected i.p. into groups of recipient mice
[b] 15 μg RSV SAM vaccine i.m. or no vaccination
[c] 3 × $10^6$ pfu RSV i.n.
[d-e] mean % response ± standard deviation of 4-5 individual animals (spleens) per group

TABLE 10

F-specific T cell responses after RSV challenge of cotton rats vaccinated with the RSV SAM vaccine in the presence or absence of passively-transferred RSV-specific antibody

| | | | | F-specific secreted cytokine 5 d post RSV chal. (d 54)[d] | |
|---|---|---|---|---|---|
| | Serum transfer[a] | Vacc.[b] | Chal.[c] | | |
| Gr. (d 0) | | (d 2 & 20) | (d 49) | IFNγ | IL-4 |
| A | RSV + subunit | — | RSV | 342 ± 138 | 2.6 ± 0.8 |
| B | 1:3 RSV + subunit | — | RSV | 1412 ± 404 | 3.0 ± 0.8 |
| C | normal | — | RSV | 176 ± 45 | 1.0 ± 0.6 |
| D | — | — | RSV | 860 ± 187 | 0.6 ± 0.6 |
| E | RSV + subunit | RSV SAM | RSV | 2941 ± 482 | 5.4 ± 0.2 |
| F | 1:3 RSV + subunit | RSV SAM | RSV | 2505 ± 606 | 3.4 ± 0.7 |
| G | normal | RSV SAM | RSV | 4444 ± 1224 | 5.0 ± 2.8 |
| H | — | RSV SAM | RSV | 3011 ± 461 | 2.8 ± 1.4 |

Abbreviations:
Gr—group,
d—day,
vacc—vaccination,
chal—challenge

[a] pooled serum from RSV-infected, F-subunit vaccine-boosted ("RSV ± subunit") or naive ("normal") cotton rats. 10 ml/kg of undiluted or 1:3 diluted serum, as indicated, was injected i.p. into groups of recipient cotton rats
[b] 15 μg RSV SAM vaccine i.m. or no vaccination
[c] 1 × $10^5$ pfu RSV i.n.
[d] mean net pg/ml ± standard error of the mean of 4-5 individual animals (spleens) per group

TABLE 11

F-specific T cell responses after RSV challenge of BALB/c vaccinated with the RSV SAM vaccine in the presence or absence of passively-transferred RSV-specific antibody

| | Serum transfer[a] | Vacc.[b] (d 2 & 22) | Chal.[c] (d 45) | % F-specific cytokine+ per CD4+d 4 days post 2nd vacc. (d 49) | | | |
|---|---|---|---|---|---|---|---|
| Gr. (d 0) | | | | IFNγ | TNFα | IL-2 | IL-5 |
| A | RSV ± subunit | — | RSV | 0.00 ± 0.00 | 0.00 ± 0.02 | −0.02 ± 0.02 | 0.00 ± 0.01 |
| B | 1:3 RSV ± subunit | — | RSV | 0.00 ± 0.00 | −0.01 ± 0.01 | 0.00 ± 0.01 | 0.00 ± 0.00 |
| C | Normal | — | RSV | 0.01 ± 0.01 | 0.00 ± 0.02 | 0.00 ± 0.01 | 0.00 ± 0.01 |
| D | — | — | RSV | 0.00 ± 0.00 | 0.00 ± 0.01 | 0.00 ± 0.01 | 0.01 ± 0.01 |

TABLE 11-continued

F-specific T cell responses after RSV challenge of BALB/c vaccinated with the RSV SAM vaccine in the presence or absence of passively-transferred RSV-specific antibody

| | | | | | | | |
|---|---|---|---|---|---|---|---|
| E | RSV ± subunit | RSV SAM | RSV | 0.02 ± 0.01 | 0.08 ± 0.03 | 0.16 ± 0.04 | 0.01 ± 0.01 |
| F | 1:3 RSV ± subunit | RSV SAM | RSV | 0.03 ± 0.02 | 0.14 ± 0.03 | 0.20 ± 0.04 | 0.01 ± 0.01 |
| G | Normal | RSV SAM | RSV | 0.04 ± 0.02 | 0.12 ± 0.03 | 0.19 ± 0.04 | 0.00 ± 0.01 |
| H | — | RSV SAM | RSV | 0.01 ± 0.01 | 0.06 ± 0.02 | 0.10 ± 0.03 | 0.00 ± 0.01 |
| I | — | — | — | 0.00 ± 0.00 | 0.00 ± 0.01 | 0.00 ± 0.01 | −0.01 ± 0.01 |

| | % F-specific cytokine$^+$ per CD8$^{+e}$ 4 days post 2$^{nd}$ vacc. (d 49) | | | |
|---|---|---|---|---|
| Gr. | IFNγ | TNFα | IL-2 | IL-5 |
| A | 0.00 ± 0.02 | 0.00 ± 0.03 | 0.01 ± 0.03 | 0.02 ± 0.02 |
| B | 0.02 ± 0.02 | 0.01 ± 0.04 | 0.00 ± 0.03 | 0.02 ± 0.02 |
| C | 0.01 ± 0.03 | 0.00 ± 0.04 | −0.01 ± 0.03 | 0.00 ± 0.02 |
| D | −0.02 ± 0.02 | −0.02 ± 0.04 | 0.01 ± 0.03 | −0.01 ± 0.02 |
| E | 0.42 ± 0.09 | 0.26 ± 0.07 | 0.10 ± 0.05 | 0.01 ± 0.03 |
| F | 0.38 ± 0.09 | 0.25 ± 0.08 | 0.08 ± 0.04 | 0.00 ± 0.02 |
| G | 0.59 ± 0.11 | 0.52 ± 0.10 | 0.16 ± 0.06 | 0.01 ± 0.02 |
| H | 0.27 ± 0.08 | 0.25 ± 0.07 | 0.08 ± 0.04 | 0.00 ± 0.03 |
| I | 0.00 ± 0.01 | −0.04 ± 0.04 | 0.00 ± 0.03 | 0.00 ± 0.03 |

Abbreviations:
Gr—group,
d—day,
vacc—vaccination,
chal—challenge,
n.t.—not tested
$^a$pooled serum from RSV-infected, F-subunit vaccine-boosted ("RSV + subunit") or naive ("normal") mice. 20 ml/kg of undiluted or 1:3 diluted serum, as indicated, was injected i.p. into groups of recipient mice
$^b$15 µg RSV SAM vaccine i.m. or no vaccination
$^c$3 × 10$^6$ pfu RSV i.n.
$^{d-e}$mean % response ± 95% CI of 2 replicates from one pool of 8 animals (spleens) per group (4 animals in group I)

TABLE 12

Summary of results from the cotton rat model

| Cotton rat treatment | | Protection from RSV challenge$^c$ on indicated day, as measured by lung viral load 5 days post challenge | |
|---|---|---|---|
| Type of serum transferred$^a$ i.p. | RNA vaccination$^b$ i.m. | | |
| (day 0) | (days 2 & 20) | Day 2 | Day 49 |
| none | none | no | no |
| RSV only | none | no | not tested |
| RSV + subunit | none | yes | no |
| none | RSV SAM | no | yes |
| RSV + subunit | RSV SAM | yes | yes (but not complete) |

$^a$pooled serum from RSV-infected, F-subunit vaccine-immunized ("RSV ± subunit") or RSV-infected, unvaccinated ("RSV") cotton rats. 10 ml/kg of undiluted serum was i.p. injected into groups of recipient cotton rats.
$^b$15 µg RSV SAM vaccine i.m. or no vaccination
$^c$1 × 10$^5$ pfu RSV i.n.

All patents, patent applications, and references cited in this disclosure, including nucleotide and amino acid sequences referred to by accession number, are expressly incorporated herein by reference. The above disclosure is a general description. A more complete understanding can be obtained by reference to the following specific examples, which are provided for purposes of illustration only.

The invention claimed is:

1. A method for providing protective immunity against RSV in an infant, comprising (a) administering a first anti-RSV immune response inducing composition to a female during pregnancy, wherein the first anti-RSV immune response inducing composition comprises an RSV subunit composition; and (b) administering a second anti-RSV immune response inducing composition to the infant that is born from the pregnancy, wherein the second anti-RSV immune response inducing composition comprises an RSV nucleic acid, a recombinant viral vector, or a viral replication particle.

2. The method of claim 1, wherein the administering in (a) boosts a neutralizing antibody response in said female.

3. The method of claim 2, wherein the neutralizing antibody response in the female is characterized by a 2-fold or greater increase in neutralizing titer.

4. The method of claim 2, wherein the neutralizing antibody response is complement independent.

5. The method of claim 1, wherein administering in (a) is a prime or a boost.

6. The method of claim 1, wherein administering in (a) is during the second or third trimester of pregnancy.

7. The method of claim 1, wherein the administering in (b) occurs at one or more times selected from the group consisting of immediately after birth, about 2 weeks after birth, about 4 weeks after birth, about 6 weeks after birth, about 2 months after birth, about 3 months after birth, about 4 months after birth, about 6 months after birth, about 9 months after birth, and about 12 months after birth.

8. A method for protecting an infant from disease caused by RSV, comprising selecting an infant born to a female to whom an anti-RSV immune response inducing subunit composition was administered during the time when said female was pregnant with said infant and administering to said infant a nucleic acid anti-RSV immune response inducing composition encoding an RSV protein antigen.

9. The method of claim 8, wherein the anti-RSV immune response inducing composition administered to said female boosted a neutralizing antibody response in said female.

10. The method of claim 8, wherein the boost in neutralizing antibody response is characterized by a 2-fold or greater increase in neutralizing titer.

11. The method of claim 8, wherein the neutralizing antibody response is complement independent.

12. The method of claim 8, wherein the anti-RSV immune response inducing composition administered to said infant is a prime or a boost.

13. The method of claim 8, wherein the anti-RSV immune response inducing composition administered to said female was administered during the second or third trimester of pregnancy.

14. The method of claim 8, wherein the administering to said infant occurs at one or more times selected from the group consisting of immediately after birth, about 2 weeks after birth, about 4 weeks after birth, about 6 weeks after birth, about 2 months after birth, about 3 months after birth, about 4 months after birth, about 6 months after birth, about 9 months after birth, and about 12 months after birth.

15. The method of claim 8, wherein said anti-RSV immune response inducing composition administered to said infant is a nucleic acid, and wherein said method further comprises administering a boost of a second RSV nucleic acid composition to said infant.

16. The method of claims 1 or 8, wherein the RSV subunit composition comprises:
   (a) one or more mutations that prevent cleavage at one or both of the furin cleavage sites of an RSV F protein;
   (b) one or more mutations in the fusion peptide region of an RSV F protein;
   (c) lack of the transmembrane region and cytoplasmic tail of an RSV F protein;
   (d) one or more oligomerization sequences; and/or
   (e) RSV glycoprotein in pre-fusion or post-fusion conformation.

17. The method of claims 1 or 8, wherein the nucleic acid comprises:
   (a) DNA; or
   (b) RNA.

18. The method of claim 8, wherein the nucleic acid anti-RSV immune response inducing composition encoding an RSV protein antigen is a self-replicating RNA.

19. The method of claim 18, wherein the RSV protein antigen is an RSV-F polypeptide.

20. The method of claim 8, wherein the RSV protein antigen is an RSV-F polypeptide.

* * * * *

SEQUENCE LISTING

<160> NUMBER OF SEQ ID NOS: 19

<210> SEQ ID NO 1
<211> LENGTH: 574
<212> TYPE: PRT
<213> ORGANISM: Human respiratory syncytial virus

<400> SEQUENCE: 1

Met Glu Leu Leu Ile Leu Lys Ala Asn Ala Ile Thr Thr Ile Leu Thr
1

```
Thr Met Asn Ser Leu Thr Leu Pro Ser Glu Ile Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
        530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570

<210> SEQ ID NO 2
<211> LENGTH: 574
<212> TYPE: PRT
<213> ORGANISM: Human respiratory syncytial virus

<400> SEQUENCE: 2

Met Glu Leu Leu Ile His Arg Ser Ser Ala Ile Phe Leu Thr Leu Ala
1               5                   10                  15

Val Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175
```

```
Ala Val Val Ser Leu Ser Asn Gly Val Ser Val Leu Thr Ser Lys Val
            180                 185                 190

Leu Asp Leu Lys Asn Tyr Ile Asn Asn Arg Leu Leu Pro Ile Val Asn
            195                 200                 205

Gln Gln Ser Cys Arg Ile Ser Asn Ile Glu Thr Val Ile Glu Phe Gln
            210                 215                 220

Gln Met Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
            275                 280                 285

Met Ser Ile Ile Lys Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
            370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                    405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
            450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
            515                 520                 525

Thr Ile Ile Ile Val Ile Ile Val Val Leu Leu Ser Leu Ile Ala Ile
            530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
            565                 570

<210> SEQ ID NO 3
<211> LENGTH: 4
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Arg Ala Arg Lys
1

<210> SEQ ID NO 4
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Arg Ala Arg Gln
1

<210> SEQ ID NO 5
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gln Ala Gln Asn
1

<210> SEQ ID NO 6
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ile Glu Gly Arg
1

<210> SEQ ID NO 7
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Arg Lys Lys Lys
1

<210> SEQ ID NO 8
<211> LENGTH: 4
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 8

Gln Asn Gln Asn
1

<210> SEQ ID NO 9
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gln Gln Gln Arg
1

<210> SEQ ID NO 10
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Ile Glu Gly Arg
1

<210> SEQ ID NO 11
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Thr Pro Ala Thr Asn Asn Arg Ala Arg Arg Glu Leu Pro Arg Phe Met
1               5                   10                  15

Asn Tyr Thr Leu Asn Asn Ala Lys Lys Thr Asn Val Thr Leu Ser Lys
            20                  25                  30

Lys Arg Lys Arg Arg Ser Ala Ile Ala Ser
        35                  40

<210> SEQ ID NO 12
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Thr Pro Ala Thr Asn Asn Arg Ala Arg Arg Glu Leu Pro Arg Phe Met
1               5                   10                  15

Asn Tyr Thr Leu Asn Asn Ala Lys Lys Thr Asn Val Thr Leu Ser Lys
            20                  25                  30

Lys Arg Lys Arg Arg Gly Val Gly Ser Ala Ile Ala Ser
        35                  40                  45
```

```
<210> SEQ ID NO 13
<211> LENGTH: 24
<212> TYPE: DNA
<213> ORGANISM: Unknown
<220> FEATURE:
<221> NAME/KEY: source
<223> OTHER INFORMATION: /note="Description of Unknown: Alphaviral
      subgenomic promoter sequence"

<400> SEQUENCE: 13
ctctctacgg ctaacctgaa tgga                                           24

<210> SEQ ID NO 14
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: VARIANT
<222> LOCATION: (2)..(2)
<223> OTHER INFORMATION: /replace="Ile"
<220> FEATURE:
<221> NAME/KEY: misc_feature
<222> LOCATION: (2)..(2)
<223> OTHER INFORMATION: /note="Residue given in the sequence has no
      preference with respect to the annotation for said position"
<220> FEATURE:
<221> NAME/KEY: MOD_RES
<222> LOCATION: (4)..(4)
<223> OTHER INFORMATION: Any amino acid

<400> SEQUENCE: 14

Asp Val Glu Xaa Asn Pro Gly Pro
1               5

<210> SEQ ID NO 15
<211> LENGTH: 8
<212> TYPE: PRT
<213> ORGANISM: Foot and mouth disease virus

<400> SEQUENCE: 15

Asp Val Glu Ser Asn Pro Gly Pro
1               5

<210> SEQ ID NO 16
<211> LENGTH: 3
<212> TYPE: PRT
<213> ORGANISM: Unknown
<220> FEATURE:
<221> NAME/KEY: source
<223> OTHER INFORMATION: /note="Description of Unknown: Integrin
      receptor-binding moiety peptide"

<400> SEQUENCE: 16

Arg Gly Asp
1

<210> SEQ ID NO 17
<211> LENGTH: 4
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 17 tttt                                                                    4

<210> SEQ ID NO 18
<211> LENGTH: 4
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18 cccc                                                                    4

<210> SEQ ID NO 19
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(100)
<223> OTHER INFORMATION: /note="This sequence may encompass 3-100
      residues"

<400> SEQUENCE: 19

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys Lys
                85                  90                  95

Lys Lys Lys Lys
            100
```